US011981705B2

(12) United States Patent
Bei et al.

(10) Patent No.: US 11,981,705 B2
(45) Date of Patent: May 14, 2024

(54) METHODS AND COMPOSITIONS FOR DELIVERY OF IMMUNOTHERAPY AGENTS ACROSS THE BLOOD-BRAIN BARRIER TO TREAT BRAIN CANCER

(71) Applicant: The Brigham and Women's Hospital, Inc., Boston, MA (US)

(72) Inventors: Fengfeng Bei, West Roxbury, MA (US); E. Antonio Chiocca, Wakefield, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/791,261

(22) PCT Filed: Jan. 8, 2021

(86) PCT No.: PCT/US2021/012746
§ 371 (c)(1),
(2) Date: Jul. 7, 2022

(87) PCT Pub. No.: WO2021/142300
PCT Pub. Date: Jul. 15, 2021

(65) Prior Publication Data

US 2023/0053817 A1 Feb. 23, 2023

Related U.S. Application Data

(60) Provisional application No. 62/959,625, filed on Jan. 10, 2020.

(51) Int. Cl.

| | |
|---|---|
| ***C12N 15/63*** | (2006.01) |
| ***A61K 31/175*** | (2006.01) |
| ***A61K 31/495*** | (2006.01) |
| ***A61K 39/395*** | (2006.01) |
| ***A61P 25/00*** | (2006.01) |
| ***A61P 35/00*** | (2006.01) |
| ***A61P 37/04*** | (2006.01) |
| ***C07K 14/005*** | (2006.01) |
| ***C07K 16/28*** | (2006.01) |
| ***C12N 15/79*** | (2006.01) |
| *A61K 39/00* | (2006.01) |

(52) U.S. Cl.
CPC .......... *C07K 14/005* (2013.01); *A61K 31/175* (2013.01); *A61K 31/495* (2013.01); *A61K 39/3955* (2013.01); *A61P 25/00* (2018.01); *A61P 35/00* (2018.01); *A61P 37/04* (2018.01); *C07K 16/2818* (2013.01); *C07K 16/2827* (2013.01); *A61K 2039/505* (2013.01); *A61K 2039/54* (2013.01); *C12N 2750/14122* (2013.01); *C12N 2750/14143* (2013.01); *C12N 2750/14171* (2013.01)

(58) Field of Classification Search
CPC .. A61K 48/00; A61K 48/005; A61K 48/0075; C12N 15/86; C12N 2750/14122; C12N 2750/14143; C07H 21/04
See application file for complete search history.

(56) References Cited

U.S. PATENT DOCUMENTS

| | | | |
|---|---|---|---|
| 4,522,811 | A | 6/1985 | Eppstein et al. |
| 8,008,449 | B2 | 8/2011 | Korman et al. |
| 8,299,215 | B2 | 10/2012 | Davidson et al. |
| 8,591,900 | B2 | 11/2013 | Barrett et al. |
| 8,927,514 | B2 | 1/2015 | Chatterjee et al. |
| 9,073,994 | B2 | 7/2015 | Honjo et al. |
| 9,102,949 | B2 | 8/2015 | Gao et al. |
| 9,585,971 | B2 | 3/2017 | Deverman et al. |
| 10,370,432 | B2 | 8/2019 | Esteves et al. |
| 10,577,627 | B2 | 3/2020 | Kotin et al. |
| 11,518,787 | B2 | 12/2022 | Bei |
| 2003/0082143 | A1 | 5/2003 | Larocca et al. |
| 2003/0165499 | A1 | 9/2003 | Chu et al. |
| 2004/0120948 | A1 | 6/2004 | Mikayama et al. |
| 2007/0148163 | A1 | 6/2007 | Takahashi et al. |
| 2011/0271358 | A1 | 11/2011 | Freeman et al. |
| 2011/0294218 | A1 | 12/2011 | Chatterjee et al. |
| 2012/0066783 | A1 | 3/2012 | Kay et al. |
| 2013/0011405 | A1 | 1/2013 | Long et al. |
| 2015/0079038 | A1 | 3/2015 | Deverman et al. |
| 2015/0297742 | A1 | 10/2015 | Strieker et al. |
| 2016/0280748 | A1 | 9/2016 | Liu et al. |
| 2016/0376325 | A1 | 12/2016 | McFadden et al. |

(Continued)

FOREIGN PATENT DOCUMENTS

| | | |
|---|---|---|
| JP | 2016145189 | 8/2016 |
| WO | WO 2002/088186 | 11/2002 |

(Continued)

OTHER PUBLICATIONS

Yu et al., 2021 (US 2021/0301024 A1, effective filing date, Jul. 4, 2018).*

(Continued)

*Primary Examiner* — Shin Lin Chen

(74) *Attorney, Agent, or Firm* — Fish & Richardson P.C.

(57) ABSTRACT

The present application relates to sequences that enhance permeation of immunotherapy agents across the blood brain barrier (BBB), compositions comprising the sequences, and methods of use thereof to treat brain cancer, e.g., glioblastoma (GBM). Further disclosed are a number of potential targeting peptide sequences identified that enhance permeation through the BBB, when inserted into the capsid of an adeno-associated virus (AAV).

18 Claims, 40 Drawing Sheets

Specification includes a Sequence Listing.

(56) References Cited

U.S. PATENT DOCUMENTS

| | | | |
|---|---|---|---|
| 2017/0058033 A1 | 3/2017 | Ludwig et al. |
| 2017/0130245 A1 | 5/2017 | Kotin et al. |
| 2017/0166926 A1 | 6/2017 | Deverman et al. |
| 2018/0030429 A1 | 2/2018 | King et al. |
| 2018/0141998 A1 | 5/2018 | Nguyen et al. |
| 2019/0367562 A1 | 12/2019 | Asokan et al. |
| 2020/0325456 A1 | 10/2020 | Li et al. |
| 2021/0163985 A1 | 6/2021 | Sah et al. |
| 2021/0277066 A1 | 9/2021 | Bei et al. |
| 2022/0089650 A1 | 3/2022 | Bei |
| 2023/0048492 A1 | 2/2023 | Bei |
| 2023/0077490 A1 | 3/2023 | Bei |

FOREIGN PATENT DOCUMENTS

| | | |
|---|---|---|
| WO | WO 2005/000220 | 1/2005 |
| WO | WO 2007/124299 | 11/2007 |
| WO | WO 2011/123489 | 10/2011 |
| WO | WO 2012/111762 | 8/2012 |
| WO | WO 2012/145601 | 10/2012 |
| WO | WO 2012/149356 | 11/2012 |
| WO | WO 2013/079174 | 6/2013 |
| WO | WO 2014/052789 | 4/2014 |
| WO | WO 2014/060109 | 4/2014 |
| WO | WO 2014/070934 | 5/2014 |
| WO | WO 2014/086835 | 6/2014 |
| WO | WO 2014/195852 | 12/2014 |
| WO | WO 2015/038958 | 3/2015 |
| WO | WO 2015/127094 | 8/2015 |
| WO | WO 2015/138628 | 9/2015 |
| WO | WO 2015/191508 | 12/2015 |
| WO | WO 2016/007235 | 1/2016 |
| WO | WO 2016/054554 | 4/2016 |
| WO | WO 2016/061142 | 4/2016 |
| WO | WO 2016/138525 | 9/2016 |
| WO | WO 2017/008336 | 1/2017 |
| WO | WO 2017/083368 | 5/2017 |
| WO | WO 2017/100671 | 6/2017 |
| WO | WO 2017/118321 | 7/2017 |
| WO | WO 2017/136536 | 8/2017 |
| WO | WO 2019/012176 | 1/2019 |
| WO | WO 2019/028306 | 2/2019 |
| WO | WO 2019126356 | 6/2019 |
| WO | WO 2019/222329 | 11/2019 |
| WO | WO 2019/222441 | 11/2019 |
| WO | WO 2020/014471 | 1/2020 |
| WO | WO 2020/028751 | 2/2020 |
| WO | WO 2020/068990 | 4/2020 |
| WO | WO 2020/072683 | 4/2020 |
| WO | WO 2020/077165 | 4/2020 |
| WO | WO 2020/160337 | 8/2020 |
| WO | WO 2020/210655 | 10/2020 |
| WO | WO 2020/223279 | 11/2020 |
| WO | WO 2021/025995 | 2/2021 |

OTHER PUBLICATIONS

Kotterman et al., 2014 (Nature Reviews, vol. 15, p. 445-451).*

Shim et al., 2017 (Current Gene Therapy, vol. 17, No. 5, p. 1-18).*

Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16).*

Bulcha et al., 2021 (Signal Transduction and Targeted Therapy, 6:53, p. 1-24).*

Bryan et al., 2013 (http://www.elsevierblogs.com/currentcomments/?p=962, Implications of protein fold switching, p. 1-4).*

Maqbool et al., 2015 (Biochemical Society Transactions, vol. 43, No. 5, p. 1011-1017).*

Cruz et al., 2017 (Methods in Molecular Biology, vol. 1654, Chapter 5, pp. 55-75).*

Alexandrescu et al., "Immunotherapy for melanoma: current status and perspectives," Journal of Immunotherapy (Hagerstown, Md.: 1997), Jul. 2010, 33(6):570.

Avan et al., "Peptidomimetics via modifications of amino acids and peptide bonds," Chemical Society Reviews, Mar. 2014, 43(10):3575, 1 page (abstract only).

Barash et al., "Human secretory signal peptide description by hidden Markov model and generation of a strong artificial signal peptide for secreted protein expression," Biochemical and Biophysical Research Communications, Jun. 21, 2002, 294(4):835, 1 page (abstract only).

Batista et al., "Ly6a differential expression in blood-brain barrier is responsible for strain specific central nervous system transduction profile of AAV-PHP. B," Human Gene Therapy, Jan. 1, 2020, 31(1-2):90-102.

Brennan et al., "The somatic genomic landscape of glioblastoma," Cell, Oct. 10, 2013, 155(2):462-77.

Chen et al., "Molecular signatures of disease brain endothelia provide new sites for CNS-directed enzyme therapy," Nature Medicine, Oct. 2009, 15(10):1215-8.

Cho et al., "Blood-brain-barrier spheroids as an in vitro screening platform for brain-penetrating agents," Nature Communications, Jun. 6, 2017, 8(1):1-4.

Deverman et al., "Cre-dependent selection yields AAV variants for widespread gene transfer to the adult brain," Nature Biotechnology, Feb. 2016, 34(2):204-9.

Deverman et al., "Gene therapy for neurological disorders: progress and prospects," Nature Reviews Drug Discovery, Sep. 2018, 17(9):641-59.

Eggermont et al., "Anti-CTLA-4 antibody adjuvant therapy in melanoma," Seminars in Oncology, Oct. 1, 2010, 37(5):455-59.

Engeland et al., "CTLA-4 and PD-L1 checkpoint blockade enhances oncolytic measles virus therapy," Molecular Therapy, Nov. 1, 2014, 22(11):1949-59.

EP Extended Search Report in European Appln. No. 19833958.2, dated Mar. 21, 2022, 9 pages.

Farhadi et al., "Computer-aided design of amino acid-based therapeutics: A review," Drug Design, Development and Therapy, 2018, 12:1239.

Flotte et al., "Expression of the cystic fibrosis transmembrane conductance regulator from a novel adeno-associated virus promoter," Journal of Biological Chemistry, Feb. 15, 1993, 268(5):3781-90.

Ganesan et al., "Systemic therapy for melanoma," National Medical Journal of India, Jan. 1, 2010, 23(1):21.

Geisler et al., "MicroRNA-regulated viral vectors for gene therapy," World Journal of Experimental Medicine, May 20, 2016, 6(2):37.

Golovina et al., "T cells: overcoming suppression of T-cell immunity," The Cancer Journal, Jul. 1, 2010, 16(4):342, 2 pages (abstract only).

Gomez et al., "Bax-inhibiting peptides derived from Ku70 and cell-penetrating pentapeptides," Biochemical Society Transactions, Aug. 1, 2007, 35(4):797-801.

Gomez et al., "Cell-penetrating penta-peptides (CPP5s): measurement of cell entry and protein-transduction activity," Pharmaceuticals, Dec. 2010, 3(12):3594-613.

Gomez, "Development of Cell Penetrating Bax Inhibiting Peptides (BIP), Doctoral dissertation," Case Western Reserve University, Jan. 2010, 189 pages.

Gray et al., "Vector design and considerations for CNS applications," Gene Vector Design and Application to Treat Nervous System Disorders, Jan. 2011, 1-9.

Hermonat et al., "Use of adeno-associated virus as a mammalian DNA cloning vector: transduction of neomycin resistance into mammalian tissue culture cells," Proceedings of the National Academy of Sciences, Oct. 1984, 81(20):6466-70.

Herrlinger et al., "Lomustine-temozolomide combination therapy versus standard temozolomide therapy in patients with newly diagnosed glioblastoma with methylated MGMT promoter (CeTeG/NOA-09): a randomised, open-label, phase 3 trial," The Lancet, Feb. 16, 2019, 393(10172):678-88.

(56) References Cited

OTHER PUBLICATIONS

Hordeaux et al., "The GPI-linked protein LY6A drives AAV-PHP. B transport across the blood-brain barrier," Molecular Therapy, May 8, 2019, 27(5):912-21.
Hordeaux et al., "The neurotropic properties of AAV-PHP. B are limited to CS7BL/6J mice, " Molecular Therapy, Mar. 7, 2018, 26(3):664-8.
Huang et al., "Delivering genes across the blood-brain barrier: LY6A, a novel cellular receptor for AAV-PHP. B capsids," PloS one, Nov. 14, 2019, 14(11):e0225206.
Hudry et al., "Therapeutic AAV gene transfer to the nervous system: a clinical reality, " Neuron, Mar. 6, 2019, 101(5):839-62.
Jain et al., "Angiogenesis in brain tumours," Nature Reviews Neuroscience, Aug. 2007, 8(8):610-22.
Klinke, "A multiscale systems perspective on cancer, immunotherapy, and Interleukin-12," Molecular Cancer, Dec. 2010, 9(1):1-8.
Kober et al., "Optimized signal peptides for the development of high expressing CHO cell lines," Biotechnology and Bioengineering, Apr. 2013, 110(4):1164-73.
Krüger et al., "Immune based therapies in cancer," Histology and Histopathology, Jun. 2007, 22(6): 687-96.
Li et al., "A mini-review for cancer immunotherapy: molecular understanding of PD-1/PD-L1 pathway & translational blockade of immune checkpoints," International Journal of Molecular Sciences, Jul. 18, 2016, 17(7):1151, 22 pages.
Lim et al., "Current state of immunotherapy for glioblastoma," Nature Reviews Clinical Oncology, Jul. 2018, 15(7):422, 1 page (abstract only).
Matsuzaki et al., "Intravenous administration of the adeno-associated virus-PHP. B capsid fails to upregulate transduction efficiency in the marmoset brain," Neuroscience Letters, Feb. 5, 2018, 665:182-8.
Mayo et al., "Design of a partial peptide mimetic of anginex with antiangiogenic and anticancer activity," Journal of Biological Chemistry, Nov. 14, 2003, 278(46):45746-52.
Milletti, "Cell-penetrating peptides: classes, origin, and current landscape," Drug Discovery Today, Aug. 1, 2012, 17(15-16):850-60.
Moschella et al., "Combination strategies for enhancing the efficacy of immunotherapy in cancer patients," Annals of the New York Academy of Sciences, May 2010, 1194(1):169, 1 page (abstract only).
Nakashima et al., "Modeling tumor immunity of mouse glioblastoma by exhausted CD8+ T cells," Scientific Reports, Jan. 2018, 8(1):1-0.
NCBI Accession No. NP_001241.1, "tumor necrosis factor receptor superfamily member 5 isoform 1 precursor [*Homo sapiens*]," dated Oct. 11, 2019, 4 pages.
NCBI Accession No. NP_001254635.1, "programmed cell death 1 ligand 1 isoform b precursor [*Homo sapiens*]," dated Dec. 8, 2019, 3 pages.
NCBI Accession No. NP_001289682.1, "tumor necrosis factor receptor superfamily member 5 isoform 3 precursor [*Homo sapiens*]," Oct. 11, 2019, 3 pages.
NCBI Accession No. NP_001300958.1, "programmed cell death 1 ligand 1 isoform c [*Homo sapiens*]," dated Dec. 8, 2019, 3 pages.
NCBI Accession No. NP_001309350.1, "tumor necrosis factor receptor superfamily member 5 isoform 4 precursor [*Homo sapiens*]," dated Oct. 10, 2019, 4 pages.
NCBI Accession No. NP_001309351.1, "tumor necrosis factor receptor superfamily member 5 isoform 5 precursor [*Homo sapiens*]," dated Oct. 10, 2019, 3 pages.
NCBI Accession No. NP_005009.2, "programmed cell death protein 1 precursor [*Homo sapiens*]," dated Dec. 4, 2019, 4 pages.
NCBI Accession No. NP_054862.1, "programmed cell death 1 ligand 1 isoform a precursor [*Homo sapiens*]," dated Dec. 8, 2019, 4 pages.
NCBI Accession No. NP_690593.1, "tumor necrosis factor receptor superfamily member 5 isoform 2 precursor [*Homo sapiens*]," dated Oct. 10, 2019, 3 pages.
Ostrom et al., CBTRUS statistical report: primary brain and other central nervous system tumors diagnosed in the United States in 2010-2014, Neuro-oncology, Nov. 6, 2017, 19(suppl 5):v1-88.
Pathak et al., "Review on peptidomimetics: a drug designing tool," American Journal of Pharmaceutical Research, Dec. 2015, 5(12).
PCT International Preliminary Report on Patentability in International Appln. No. PCT/US2019/041386, dated Jan. 12, 2021, 7 pages.
PCT International Preliminary Report on Patentability in International Appln. No. PCT/US2021/012746, dated Jul. 12, 2022, 10 pages.
PCT International Search Report and Written Opinion in International Appln. No. PCT/US2019/041386, dated Oct. 17, 2019, 15 pages.
PCT International Search Report and Written Opinion in International Appln. No. PCT/US2021/012746, dated Jul. 1, 2021, 17 pages.
PCT International Search Report and Written Opinion in International Appln. No. PCT/US2022/073051, dated Dec. 28, 2022, 14 pages.
Perry et al., "Histologic classification of gliomas," Handbook of Clinical Neurology, Jan. 1, 2016, 134:71, 1 pages (abstract only).
Pulicherla et al., "Engineering liver-detargeted AAV9 vectors for cardiac and musculoskeletal gene transfer," Molecular Therapy, Jun. 1, 2011, 19(6):1070-8.
Qvit et al., "Peptidomimetic therapeutics: scientific approaches and opportunities," Drug Discovery Today, Feb. 2017, 22(2):454-62.
Reul et al., "Tumor-specific delivery of immune checkpoint inhibitors by engineered AAV vectors," Frontiers in Oncology, Feb. 14, 2019, 9:52.
Stupp et al., "Radiotherapy plus concomitant and adjuvant temozolomide for glioblastoma," New England Journal of Medicine, Mar. 10, 2005, 352(10):987-96.
Sun et al., "Enhanced efficacy of an AAV vector encoding chimeric, highly secreted acid α-glucosidase in glycogen storage disease type II," Molecular Therapy, Dec. 1, 2006, 14(6):822-30.
Tratschin et al., "A human parvovirus, adeno-associated virus, as a cucaryotic vector: transient expression and encapsidation of the procaryotic gene for chloramphenicol acetyltransferase, " Molecular and Cellular Biology, Oct. 1984, 4(10):2072-81.
Tratschin et al., "Adeno-associated virus vector for high-frequency integration, expression, and rescue of genes in mammalian cells," Molecular and Cellular Biology, Nov. 1985, 5(11):3251-60.
Tratschin et al., "Genetic analysis of adeno-associated virus: properties of deletion mutants constructed in vitro and evidence for an adeno-associated virus replication function," Journal of Virology, Sep. 1984, 51(3):611-9.
Tsuchiya et al., "Gene design of signal sequence for effective secretion of protein, "Nucleic Acids Symposium Series, Sep. 2003, 3(1):261-62.
Von Heijne, "Signal sequences: the limits of variation," Journal of Molecular Biology, Jul. 1985, 184(1):99, 1 page (abstract only).
Wang et al., "A rationally engineered capsid variant of AAV9 for systemic CNS-directed and peripheral tissue-detargeted gene delivery in neonates," Molecular Therapy-Methods & Clinical Development, Jun. 15, 2018, 9:234-46.
Wen et al., "Malignant gliomas in adults," New England Journal of Medicine, Jul. 31, 2008, 359(5):492-507.
Wolfe et al., "Machine learning to predict cell-penetrating peptides for antisense delivery," ACS Central Science, Apr. 5, 2018, 4(4):512-20.
Wondisford et al., "Cloning of the human thyrotropin β-subunit gene and transient expression of biologically active human thyrotropin after gene transfection," Molecular Endocrinology, Jan. 1988, 2(1):32-9.
Xu et al., "A combination of mutations enhances the neurotropism of AAV-2," Virology, Oct. 25, 2005, 341(2):203-14.
EP Supplementary European Search Report in European Appln. No. 21738480.9, dated Oct. 30, 2023, 11 pages.
Gomez et al., "Cell-penetrating penta-peptides and BAX-inhibiting peptides: Protocol for their application," Cell-Penetrating Peptides: Methods and Protocols, Jan. 2011, 683:465, 6 pages.

(56) References Cited

OTHER PUBLICATIONS

Zhang et al., "Blood-brain barrier shuttle peptides enhance AAV transduction in the brain after systemic administration," Biomaterials, Sep. 2018, 176:71, 27 pages.
Chao et al., "Gene therapy for human lung adenocarcinoma using a suicide gene driven by a lung-specific promoter delivered by JC virus-like particles," PLoS One, Jun. 2016, 11(6):e0157865, 12 pages.
Doerfler et al., "Copackaged AAV9 vectors promote simultaneous immune tolerance and phenotypic correction of Pompe disease," Human Gene Therapy, Jan. 2016, 27(1):43-59.
Gam et al., "A mixed antagonistic/synergistic miRNA repression model enables accurate predictions of multi-input miRNA sensor activity," Nature Communications, Jun. 2018, 9(1):2430, 12 pages.
JP Japanese Office Action in Japanese Appln. No. 2021-500538, dated Jun. 6, 2023, 11 pages (with English translation).
Nyon et al., "Engineering a stable CHO cell line for the expression of a MERS-coronavirus vaccine antigen," Vaccine, Mar. 2018, 36(14):1853-62.
snapgene.com, "GAM hsa-mi R-1-5p target sequence," Jun. 3 22, 2018, 1 page.
snapgene.com, "GAM lsb hsa miR-200c-5p target sequence," Jun. 22, 2018, 1 page.
Trepel et al., "Treatment of multifocal breast cancer by systemic delivery of dual-targeted adeno-associated viral vectors," Gene Therapy, Oct. 2015, 22(10):840-7.
Wu et al., "AAV2/S-mediated NGF gene delivery protects septal cholinergic neurons following axotomy," Brain Research, Nov. 2005, 1061(2):107-13.
Xie et al., "MicroRNA-regulated, systemically delivered rAAV9: a step closer to CNS-restricted transgene expression," Molecular Therapy, Mar. 2011, 19(3):526-35.

* cited by examiner

AAV-H2B-RFP, 1 × $10^{10}$ vg

V IV III II I

| | 575 | | | | | | | 582 | |
|---|---|---|---|---|---|---|---|---|---|
| Human Ku70 (609 aa) | ... K | F | T | V | P | M | L | K ... | SEQ ID NO:69 |
| | 573 | | | | | | | 580 | |
| Mouse Ku70 (608 aa) | ... K | L | T | V | P | T | L | K ... | SEQ ID NO:70 |
| | 573 | | | | | | | 580 | |
| Rat Ku70 (608 aa) | ... K | F | T | V | P | A | L | R ... | SEQ ID NO:71 |

| AAV | Insert | |
|---|---|---|
| AAV-CPP.11 | VPALR | SEQ ID NO:1 |
| AAV-CPP.12 | VSALK | SEQ ID NO:2 |
| AAV-CPP.15 | TVPALR | SEQ ID NO:3 |
| AAV-CPP.16 | TVSALK | SEQ ID NO:4 |
| AAV-CPP.17 | FTVSALK | SEQ ID NO:5 |
| AAV-CPP.18 | LTVSALK | SEQ ID NO:6 |
| AAV-CPP.19 | KFTVSALK | SEQ ID NO:72 |
| AAV-CPP.20 | TFVSALK | SEQ ID NO:7 |
| AAV-CPP.21 | TVSALFK | SEQ ID NO:8 |

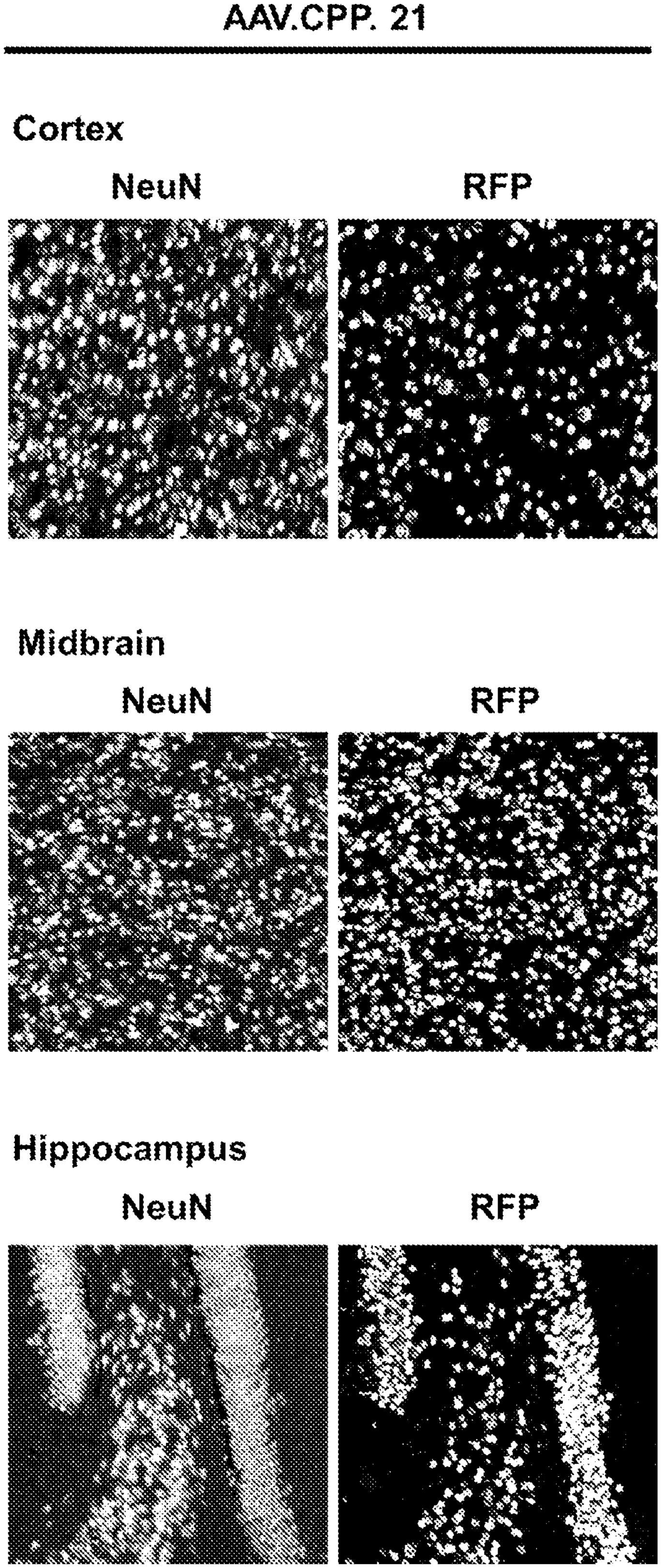
*FIG. 8A, continued*

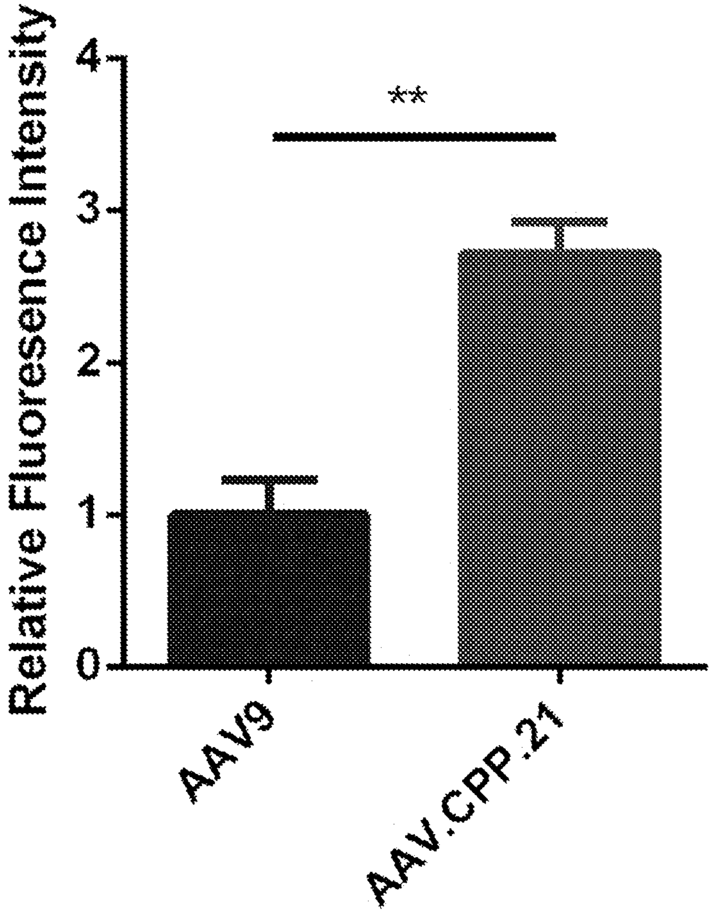
FIG. 13, continued

METHODS AND COMPOSITIONS FOR DELIVERY OF IMMUNOTHERAPY AGENTS ACROSS THE BLOOD-BRAIN BARRIER TO TREAT BRAIN CANCER

CLAIM OF PRIORITY

This application is a U.S. National Phase Application under 35 U.S.C. § 371 of International Patent Application No. PCT/US2021/012746, filed on Jan. 8, 2021, which claims the benefit of U.S. Provisional Application Ser. No. 62/959,625, filed on Jan. 10, 2020. The entire contents of the foregoing are incorporated herein by reference.

SEQUENCE LISTING

This application contains a Sequence Listing that has been submitted electronically as an ASCII text file named 'Sequence_Listing'. The ASCII text file, created on Jul. 6, 2022, is 66.8 kilobytes in size. The material in the ASCII text file is hereby incorporated by reference in its entirety.

TECHNICAL FIELD

Described herein are sequences that enhance permeation of immunotherapy agents across the blood brain barrier, compositions comprising the sequences, and methods of use thereof to treat brain cancer, e.g., glioblastoma (GBM).

BACKGROUND

Glioblastoma multiforme (GBM) is the most common and deadly brain tumor in adults with a median overall survival of only 15 months[1]. Approximately 12,000 new GBM cases are diagnosed every year in the United States with an incidence rate of 3.2 per 100,000 population[2]. Despite significant progress made in understanding the histology, molecular landscape and tumor microenvironment of GBM[3-6], there have been few therapeutic advances since 2005. One critical obstacle in turning our wealth of knowledge on GBM into effective therapy is the inefficient drug delivery to the GBM tumor site. Intravenous administration is a convenient and widely applicable route of drug administration that, in theory, could achieve good tumor coverage as GBM tumor is well vascularized structurally[7]. However, designing drugs that cross the blood-brain barrier (BBB) and/or blood-tumor barrier remains challenging.

SUMMARY

Glioblastoma is an extremely deadly brain cancer that is difficult to treat using conventional methods. Systemically administered cancer gene therapy is a new treatment paradigm for tackling glioblastoma. Described herein are brain-penetrant AAV viral vectors engineered to establish an intravascular gene delivery platform for glioblastoma gene therapy, e.g., to systemically delivers PD-L1 antibodies for the treatment of glioblastoma.

Thus, provided herein are methods for delivering an immunotherapy agent to a cancer in a subject. The methods include administering to the subject an adeno-associated virus (AAV) comprising (i) a capsid protein comprising an amino acid sequence that comprises at least four contiguous amino acids from the sequence TVSALFK (SEQ ID NO:8); TVSALK (SEQ ID NO:4); KLASVT (SEQ ID NO:83); or KFLASVT (SEQ ID NO:84), and (ii) a transgene encoding an immunotherapy agent, optionally wherein the cancer cell is in the brain of a human subject.

In some embodiments, the amino acid sequence comprises at least five contiguous amino acids from the sequence TVSALK (SEQ ID NO:4); TVSALFK (SEQ ID NO:8); KLASVT (SEQ ID NO:83); or KFLASVT (SEQ ID NO:84).

In some embodiments, the amino acid sequence comprises at least six contiguous amino acids from the sequence TVSALK (SEQ ID NO:4); TVSALFK (SEQ ID NO:8); KLASVT (SEQ ID NO:83); or KFLASVT (SEQ ID NO:84).

Also provided herein are methods for delivering an immunotherapy agent to a cancer in a subject. The methods include administering to the subject an adeno-associated virus (AAV) comprising (i) a capsid protein comprising an amino acid sequence that comprises at least four contiguous amino acids from the sequence V[S/p][A/m/t/]L (SEQ ID NO:79), TV[S/p][A/m/t/]L (SEQ ID NO:80), TV[S/p][A/m/t/]LK (SEQ ID NO:81), or TV[S/p][A/m/t/]LFK. (SEQ ID NO:82), and (ii) a transgene encoding an immunotherapy agent, optionally wherein the cancer cell is in the brain of a human subject.

In some embodiments, the targeting sequence comprises VPALR (SEQ ID NO:1); VSALK (SEQ ID NO:2); TVPALR (SEQ ID NO:3); TVSALK (SEQ ID NO:4); TVPMLK (SEQ ID NO:12); TVPTLK (SEQ ID NO:13); FTVSALK (SEQ ID NO:5); LTVSALK (SEQ ID NO:6); TVSALFK (SEQ ID NO:8); TVPALFR (SEQ ID NO:9); TVPMLFK (SEQ ID NO:10) or TVPTLFK (SEQ ID NO:11).

In some embodiments, the transgene encoding an immunotherapy agent encodes an antibody targeting PD-1 or PD-L1.

In some embodiments, the subject is a mammalian subject.

In some embodiments, the AAV is AAV9.

In some embodiments, the AAV9 comprises AAV9 VP1.

In some embodiments, the targeting sequence is inserted in a position corresponding to amino acids 588 and 589 of AAV9 VP1 comprising SEQ ID NO:85.

In some embodiments, the cell is in the brain of the subject, and the AAV is administered by parenteral delivery; intracerebral; or intrathecal delivery.

In some embodiments, the parenteral delivery is via intravenous, intraarterial, subcutaneous, intraperitoneal, or intramuscular delivery.

In some embodiments, the intrathecal delivery is via lumbar injection, cisternal magna injection, or intraparenchymal injection.

In some embodiments, the methods further include administering chemotherapy, radiation, and/or surgical resection to the subject.

In some embodiments, the chemotherapy comprises temozolamide, lomustine, or a combination thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a 3D model of an AAV9 virus. Individual CPP inserted into the capsid between amino acids 588 and 589 (VP1 numbering) will be displayed at the 3-fold axis where receptor binding presumably occurs. FIG. 1B illustrates the method of individual AAV production. Three plasmids including pRC (engineered or not), pHelper and pAAV are co-transfected into HEK 293T cells, with AAVs harvested and purified using iodixanol gradient. FIG. 1C is a vector diagram of an exemplary vector comprising a sequence encoding an anti-PDL1 antibody.

In FIG. 2B, * $P<0.05$, vs. AAV9, ANOVA.

In FIG. 2D, * $P<0.05$, ** $P<0.01$, vs. AAV9, ANOVA.

In FIG. 3C, * $P<0.05$,  $P<0.01$, * $P<0.001$, vs. AAV9, ANOVA.

FIG. 4A illustrates the spheroid comprising human microvascular endothelial cells, which forms a barrier at the surface, and human pericyte and astrocytes inside the spheroid. Candidate AAVs were assessed for their ability to penetrate from the surrounding medium into the inside of the spheroid and to transduce the cells inside. FIG. 4B-4D shows images of AAV9 (FIG. 4B), AAV.CPP.16 (FIG. 4C) and AAV.CPP.21 (FIG. 4D) treated spheroids. FIG. 4E shows relative RFP intensity of different AAV treated spheroids. *** $P<0.001$, vs. AAV9, ANOVA.

In FIG. 5B, * $P<0.05$, *** $P<0.001$, ANOVA.

In FIG. 6B, *** $P<0.001$, ANOVA.

In FIG. 7B, * $P<0.05$, Student test.

In FIG. 11B (images) and FIG. 11C (quantitative analysis), using AAV.CPP.21 to systemically deliver the "suicide gene" HSV.TK1 results in shrinkage of brain tumor mass, when combined with the pro-drug ganciclovir. HSV.TK1 turns the otherwise "dormant" ganciclovir into a tumor-killing drug. * P<0.05, Student test.

FIG. 15A, schematic of experimental protocol. FIG. 15B, survival in animals treated as indicated. FIG. 15C, long term survival in animals treated with AAV.CPP16-anti-PDL1. LTS: long-term survival.

FIG. 16A, H&E staining of brain sections both posterior and anterior to the tumor injection site. No residual GBM in any section. FIG. 16B, Bioluminescent imaging 7 days after tumor implant suggesting success of initial tumor implantation. FIG. 16C, GBM tumor implantation site with scar-like tissues.

DETAILED DESCRIPTION

Figure 1A:
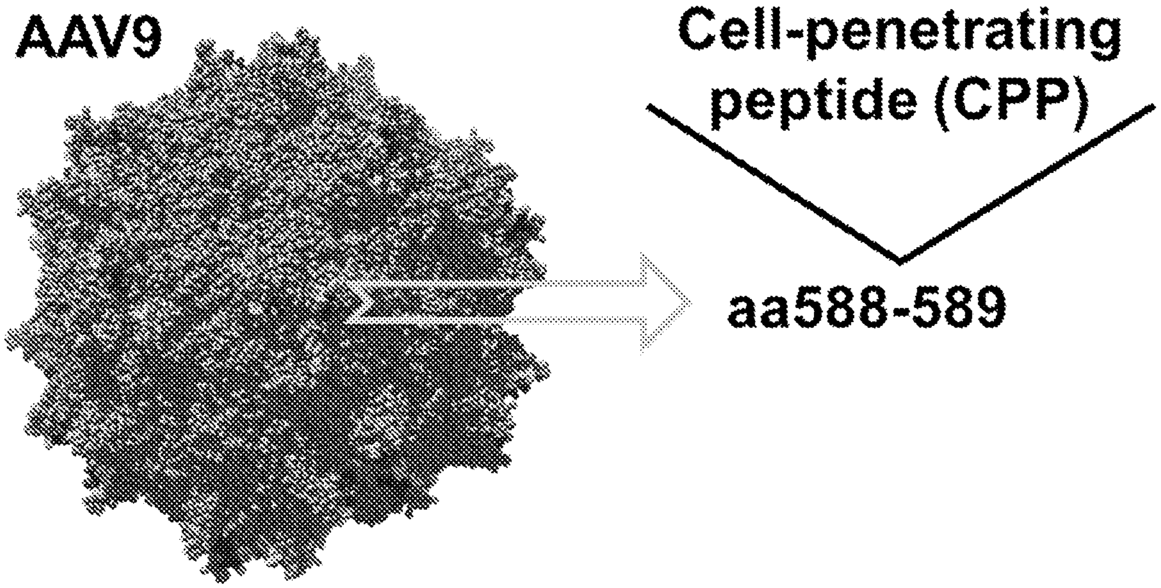
FIGS. 1A-1C depict an exemplary strategy of engineering AAV9 by inserting cell-penetrating peptides (CPPs) into its capsid.

Difficulties associated with delivery across the BBB have hindered development of therapeutic agents to treat brain disorders including cancer. Adeno-associated virus (AAV) has emerged as an important research and clinical tool for delivering therapeutic genes to the brain, spinal cord and the eye; see, e.g., U.S. Pat. Nos. 9,102,949; 9,585,971; and US20170166926. Gene therapy mediated by AAVs has made significant progress with the recent approvals of Luxturna and Zolgensma. The approval of Zolgensma for intravascular treatment of spinal muscular atrophy patients under two years of age is particular encouraging, as it demonstrates the feasibility of using BBB-crossing AAV vectors for systemic gene therapy of the central nervous system (CNS). Despite of its success in young patients, AAV9, which is the AAV serotype used in Zolgensma, suffers from low efficiency of BBB crossing, particularly in adults, which limits its application for other CNS diseases[8,9]. Described herein are next-generation, brain-penetrant AAV vectors (namely, AAV.CPP16) that achieves at least 5-10 fold enhancement over current industrial standard (i.e. AAV9) in both rodents and non-human primates, that can be used for a new BBB-crossing AAV platform for GBM cancer gene therapy.

Through rational design and targeted screening on the basis of known cell-penetrating peptides (CPPs) (see, e.g., Gomez et al., *Bax-inhibiting peptides derived from Ku70 and cell-penetrating pentapeptides*. Biochem. Soc. Trans. 2007; 35(Pt 4):797-801), targeting sequences have been discovered that, when engineered into the capsid of an AAV, improved the efficiency of gene delivery to the brain by up to three orders of magnitude. These methods were used to engineer AAV vectors that dramatically reduce tumor size in an animal model of glioblastoma.

In addition, the brain is "immune privileged", which renders immunotherapy of GBM challenging. "Priming" the immune response is desirable to turn the immunologically "cold" GBM tumor into an immunogenic, "hot" one. The present methods make use of the vectors described herein to deliver immunotherapeutics that may achieve just that, e.g., anti-PD-L1 antibodies. Without wishing to be bound by theory, it is believed that the AAV vector itself "primes" the immune system by increasing tumor infiltration of cytotoxic T cells while the antiPD-L1 antibody expressed at the tumor site, and in the CNS at large, activates the otherwise "exhausted" T cells.

Targeting Sequences

The present methods identified a number of potential targeting peptides that enhance permeation through the BBB, e.g., when inserted into the capsid of an AAV, e.g., AAV1, AAV2, AAV8, or AAV9, or when conjugated to a biological agent, e.g., an antibody or other large biomolecule, either chemically or via expression as a fusion protein.

In some embodiments, the targeting peptides comprise sequences of at least 5 amino acids. In some embodiments, the amino acid sequence comprises at least 4, e.g., 5, contiguous amino acids of the sequences VPALR (SEQ ID NO:1) and VSALK (SEQ ID NO:2).

In some embodiments, the targeting peptides comprise a sequence of $X_1$ $X_2$ $X_3$ $X_4$ $X_5$, wherein:

(i) $X_1$, $X_2$, $X_3$, $X_4$ are any four non-identical amino acids of V, A, L, I, G, P, S, T, or M; and (ii) $X_5$ is K, R, H, D, or E (SEQ ID NO:73).

In some embodiments, the targeting peptides comprise sequences of at least 6 amino acids. In some embodiments, the amino acid sequence comprises at least 4, e.g., 5 or 6 contiguous amino acids of the sequences TVPALR (SEQ ID NO:3), TVSALK (SEQ ID NO:4), TVPMLK (SEQ ID NO:12) and TVPTLK (SEQ ID NO:13).

In some embodiments, the targeting peptides comprise a sequence of $X_1$ $X_2$ $X_3$ $X_4$ $X_5$ $X_6$, wherein:

(i) $X_1$ is T;

(ii) $X_2$, $X_3$, $X_4$, $X_5$ are any four non-identical amino acids of V, A, L, I, G, P, S, T, or M; and (iii) $X_6$ is K, R, H, D, or E (SEQ ID NO:74).

In some embodiments, the targeting peptides comprise a sequence of $X_1$ $X_2$ $X_3$ $X_4$ $X_5$ $X_6$, wherein:

(i) $X_1$, $X_2$, $X_3$, $X_4$ are any four non-identical amino acids from V, A, L, I, G, P, S, T, or M;

(ii) $X_5$ is K, R, H, D, or E; and (iii) $X_6$ is E or D (SEQ ID NO:75).

In some embodiments, the targeting peptides comprise sequences of at least 7 amino acids. In some embodiments, the amino acid sequence comprises at least 4, e.g., 5, 6, or 7 contiguous amino acids of the sequences FTVSALK (SEQ ID NO:5), LTVSALK (SEQ ID NO:6), TVSALFK (SEQ ID NO:8), TVPALFR (SEQ ID NO:9), TVPMLFK (SEQ ID NO:10) and TVPTLFK (SEQ ID NO:11). In some other embodiments, the targeting peptides comprise a sequence of $X_1$ $X_2$ $X_3$ $X_4$ $X_5$ $X_6$ $X_7$, wherein:

(i) $X_1$ is F, L, W, or Y;

(ii) $X_2$ is T;

(iii) $X_3$, $X_4$, $X_5$, $X_6$ are any four non-identical amino acids of V, A, L, I, G, P, S, T, or M; and (iv) $X_7$ is K, R, H, D, or E (SEQ ID NO:76).

In some embodiments, the targeting peptides comprise a sequence of $X_1$ $X_2$ $X_3$ $X_4$ $X_5$ $X_6$ $X_7$, wherein:

(i) $X_1$ is T;

(ii) $X_2$, $X_3$, $X_4$, $X_5$ are any four non-identical amino acids of V, A, L, I, G, P, S, T, or M;

(iii) $X_6$ is K, R, H, D, or E; and (iv) $X_7$ is E or D (SEQ ID NO:77).

In some embodiments, the targeting peptides comprise a sequence of $X_1$ $X_2$ $X_3$ $X_4$ $X_5$ $X_6$ $X_7$, wherein:

(i) $X_1$, $X_2$, $X_3$, $X_4$ are any four non-identical amino acids of V, A, L, I, G, P, S, T, or M;

(ii) $X_5$ is K, R, H, D, or E;

(iii) $X_6$ is E or D; and (iv) $X_7$ is A or I (SEQ ID NO:78).

In some embodiments, the targeting peptides comprise a sequence of V[S/p][A/m/t/]L (SEQ ID NO:79), wherein the upper case letters are preferred at that position. In some embodiments, the targeting peptides comprise a sequence of TV[S/p][A/m/t/]L (SEQ ID NO:80). In some embodiments, the targeting peptides comprise a sequence of TV[S/p][A/m/t/]LK (SEQ ID NO:81). In some embodiments, the targeting peptides comprise a sequence of TV[S/p][A/m/t/]LFK. (SEQ ID NO:82).

In some embodiments, the targeting peptide does not consist of VPALR (SEQ ID NO:1) or VSALK (SEQ ID NO:2).

Specific exemplary amino acid sequences that include the above mentioned 5, 6, or 7-amino acid sequences are listed in Table 1.

TABLE 1

Targeting Sequences

| SEQ ID NO: | Targeting Peptide Sequence |
|---|---|
| 1. | VPALR |
| 2. | VSALK |
| 3. | TVPALR |
| 4. | **TVSALK** |
| 5. | FTVSALK |
| 6. | LTVSALK |
| 7. | TFVSALK |
| 8. | **TVSALFK** |
| 9. | TVPALFR |
| 10. | **TVPMLFK** |
| 11. | TVPTLFK |
| 12. | TVPMLK |
| 13. | TVPTLK |
| 14. | VPMLK |
| 15. | VPTLK |
| 16. | **VPMLKE** |

TABLE 1-continued

| Targeting Sequences | |
|---|---|
| SEQ ID NO: | Targeting Peptide Sequence |
| 17. | VPTLKD |
| 18. | VPALRD |
| 19. | **VSALKE** |
| 20. | **VSALKD** |
| 21. | TAVSLK |
| 22. | TALVSK |
| 23. | TVLSAK |
| 24. | TLVSAK |
| 25. | TMVPLK |
| 26. | TMLVPK |
| 27. | TVLPMK |
| 28. | TLVPMK |
| 29. | TTVPLK |
| 30. | TTLVPK |
| 31. | TVLPTK |
| 32. | TLVPTK |
| 33. | TAVPLR |
| 34. | TALVPR |
| 35. | TVLPAR |
| 36. | TLVPAR |
| 37. | TAVSLKE |
| 38. | TALVSKE |
| 39. | TVLSAKE |
| 40. | TLVSAKE |
| 41. | TMVPLKE |
| 42. | TMLVPKE |
| 43. | TVLPMKE |
| 44. | TLVPMKE |
| 45. | TTVPLKD |
| 46. | TTLVPKD |
| 47. | TVLPTKD |
| 48. | TLVPTKD |
| 49. | TAVPLRD |
| 50. | TALVPRD |
| 51. | TVLPARD |
| 52. | TLVPARD |
| 53. | TAVSLFK |
| 54. | TALVSFK |

TABLE 1-continued

| Targeting Sequences | |
|---|---|
| SEQ ID NO: | Targeting Peptide Sequence |
| 55. | TVLSAFK |
| 56. | TLVSAFK |
| 57. | TMVPLFK |
| 58. | TMLVPFK |
| 59. | TVLPMFK |
| 60. | TLVPMFK |
| 61. | TTVPLFK |
| 62. | TTLVPFK |
| 63. | TVLPTFK |
| 64. | TLVPTFK |
| 65. | TAVPLFR |
| 66. | TALVPFR |
| 67. | TVLPAFR |
| 68. | TLVPAFR |

Targeting peptides including reversed sequences can also be used, e.g., KLASVT (SEQ ID NO:83) and KFLASVT (SEQ ID NO:84).

Targeting peptides disclosed herein can be modified according to the methods known in the art for producing peptidomimetics. See, e.g., Qvit et al., Drug Discov Today. 2017 February; 22(2): 454-462; Farhadi and Hashemian, Drug Des Devel Ther. 2018; 12: 1239-1254; Avan et al., Chem. Soc. Rev., 2014,43, 3575-3594; Pathak, et al., Indo American Journal of Pharmaceutical Research, 2015. 8; Kazmierski, W. M., ed., Peptidomimetics Protocols, Human Press (Totowa NJ 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetic include replacing one or more amino acid residues in a peptide with a chemically distinct but recognized functional analog of the amino acid, i.e., an artificial amino acid analog. Artificial amino acid analogs include β-amino acids, β-substituted β-amino acids ("$\beta^3$-amino acids"), phosphorous analogs of amino acids, such as ∀-amino phosphonic acids and ∀-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules. Exemplary retro-inverso targeting peptidomimetics include KLASVT and KFLASVT, wherein the sequences include all D-amino acids. These sequences can be modified, e.g., by biotinylation of the amino terminus and amidation of the carboxy terminus.

AAVs

Viral vectors for use in the present methods and compositions include recombinant retroviruses, adenovirus, adeno-associated virus, alphavirus, and lentivirus, comprising the targeting peptides described herein and optionally a transgene for expression in a target tissue.

A preferred viral vector system useful for delivery of nucleic acids in the present methods is the adeno-associated virus (AAV). AAV is a tiny non-enveloped virus having a 25 nm capsid. No disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Vectors containing as little as 300 base pairs of AAV can be packaged and can integrate. Space for exogenous DNA is limited to about 4.7 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993). There are numerous alternative AAV variants (over 100 have been cloned), and AAV variants have been identified based on desirable characteristics. In some embodiments, the AAV is AAV1, AAV2, AAV4, AAV5, AAV6, AV6.2, AAV7, AAV8, AAV9, rh. 10, rh. 39, rh. 43 or CSp3; for CNS use, in some embodiments the AAV is AAV1, AAV2, AAV4, AAV5, AAV6, AAV8, or AAV9. As one example, AAV9 has been shown to somewhat efficiently cross the blood-brain barrier. Using the present methods, the AAV capsid can be genetically engineered to increase permeation across the BBB, or into a specific tissue, by insertion of a targeting sequence as described herein into the capsid protein, e.g., into the AAV9 capsid protein VP1 between amino acids 588 and 589.

An exemplary wild type AAV9 capsid protein VP1 (Q6JC40-1) sequence is as follows:

```
                                      (SEQ ID NO: 85)
         10         20         30         40
MAADGYLPDW LEDNLSEGIR EWWALKPGAP QPKANQQHQD
         50         60         70         80

NARGLVLPGY KYLGPGNGLD KGEPVNAADA AALEHDKAYD
         90        100        110        120
```

-continued

```
QQLKAGDNPY LKYNHADAEF QERLKEDTSF GGNLGRAVFQ
       130        140        150        160

AKKRLLEPLG LVEEAAKTAP GKKRPVEQSP QEPDSSAGIG
       170        180        190        200

KSGAQPAKKR LNFGQTGDTE SVPDPQPIGE PPAAPSGVGS
       210        220        230        240

LTMASGGGAP VADNNEGADG VGSSSGNWHC DSQWLGDRVI
       250        260        270        280

TTSTRTWALP TYNNHLYKQI SNSTSGGSSN DNAYFGYSTP
       290        300        310        320

WGYFDFNRFH CHFSPRDWQR LINNNWGFRP KRLNFKLFNI
       330        340        350        360

QVKEVTDNNG VKTIANNLTS TVQVFTDSDY QLPYVLGSAH
       370        380        390        400

EGCLPPFPAD VFMIPQYGYL TLNDGSQAVG RSSFYCLEYF
       410        420        430        440

PSQMLRTGNN FQFSYEFENV PFHSSYAHSQ SLDRLMNPLI
       450        460        470        480

DQYLYYLSKT INGSGQNQQT LKFSVAGPSN MAVQGRNYIP
       490        500        510        520

GPSYRQQRVS TTVTQNNNSE FAWPGASSWA LNGRNSLMNP
       530        540        550        560

GPAMASHKEG EDRFFPLSGS LIFGKQGTGR DNVDADKVMI
       570        580        590        600

TNEEEIKTTN PVATESYGQV ATNHQSAQAQ AQTGWVQNQG
       610        620        630        640

ILPGMVWQDR DVYLQGPIWA KIPHTDGNFH PSPLMGGFGM
       650        660        670        680

KHPPPQILIK NTPVPADPPT AFNKDKLNSF ITQYSTGQVS
       690        700        710        720

VEIEWELQKE NSKRWNPEIQ YTSNYYKSNN VEFAVNTEGV
       730

YSEPRPIGTR YLTRNL
```

Thus provided herein are AAV that include one or more of the targeting peptide sequences described herein, e.g., an AAV comprising a capsid protein comprising a targeting sequence described herein, e.g., a capsid protein comprising SEQ ID NO:1 wherein a targeting peptide sequence has been inserted into the sequence, e.g., between amino acids 588 and 589.

Immunotherapeutic Transgenes

In some embodiments, the AAV also includes a transgene sequence (i.e., a heterologous sequence) encoding an immunotherapeutic agent, e.g., as described herein or as known in the art. The transgene is preferably linked to sequences that promote/drive expression of the transgene in the target tissue.

Exemplary transgenes for use as immunotherapeutics include those encoding an immune checkpoint inhibitory antibody or antigen-binding fragment thereof, e.g., single-chain variable fragment (scFv) antibodies that act as checkpoint inhibitors.

Examples of immunotherapies include, but are not limited to, adoptive T cell therapies or cancer vaccine preparations designed to induce T lymphocytes to recognize cancer cells, as well as checkpoint inhibitors such as anti-CD137 antibodies (e.g., BMS-663513), anti-PD1 antibodies (e.g., Nivolumab, pembrolizumab/MK-3475, Pidilizumab (CT-011)), anti-PDL1 antibodies (e.g., BMS-936559, MPDL3280A), or anti-CTLA-4 antibodies (e.g., ipilumimab; see, e.g., Krüger et al. (2007) *Histol Histopathol.* 22(6): 687-96; Eggermont et al. (2010) *Semin Oncol.* 37(5): 455-9; Klinke (2010) *Mol. Cancer.* 9: 242; Alexandrescu et al. (2010) *J. Immunother.* 33(6): 570-90; Moschella et al. (2010) *Ann N Y Acad Sci.* 1194: 169-78; Ganesan and Bakhshi (2010) *Natl. Med. J. India* 23(1): 21-7; and Golovina and Vonderheide (2010) *Cancer J.* 16(4): 342-7.

Exemplary anti-PD-1 antibodies that can be used in the methods described herein include those that bind to human PD-1; an exemplary PD-1 protein sequence is provided at NCBI Accession No. NP 005009.2. Exemplary antibodies are described in U.S. Pat. Nos. 8,008,449; 9,073,994; and U.S. Publication No. 2011/0271358, including, e.g., PF-06801591, AMP-224, BGB-A317, BI 754091, JS001, MEDI0680, PDR001, REGN2810, SHR-1210, TSR-042, pembrolizumab, nivolumab, avelumab, Cemiplimab, Spartalizumab, Camrelizumab, Sintilimab, pidilizumab, Tislelizumab, Toripalimab, AMP-224, AMP-514, and atezolizumab.

Exemplary anti-CD40 antibodies that can be used in the methods described herein include those that bind to human CD40; exemplary CD40 protein precursor sequences are provided at NCBI Accession No. NP_001241.1, NP_690593.1, NP_001309351.1, NP_001309350.1 and NP_001289682.1. Exemplary antibodies include those described in International Publication Nos. WO 2002/088186; WO 2007/124299; WO 2011/123489; WO 2012/149356; WO 2012/111762; WO 2014/070934; U.S. Publication Nos. 2013/0011405; 2007/0148163; 2004/0120948; 2003/0165499; and U.S. Pat. No. 8,591,900; including, e.g., dacetuzumab, lucatumumab, bleselumab, teneliximab, ADC-1013, CP-870,893, Chi Lob 7/4, HCD122, SGN-4, SEA-CD40, BMS-986004, and APX005M. In some embodiments, the anti-CD40 antibody is a CD40 agonist, and not a CD40 antagonist.

Exemplary anti-PD-L1 antibodies that can be used in the methods described herein include those that bind to human PD-L1; exemplary PD-L1 protein sequences are provided at NCBI Accession No. NP_001254635.1, NP_001300958.1, and NP_054862.1. Exemplary antibodies are described in U.S. Publication No. 2017/0058033; International Publication Nos. WO 2017/118321A1; WO 2016/061142A1; WO 2016/007235A1; WO 2014/195852A1; and WO 2013/079174A1, including, e.g., BMS-936559 (MDX-1105), FAZ053, KN035, Atezolizumab (Tecentriq, MPDL3280A), Avelumab (Bavencio), Durvalumab (Imfinzi, MEDI-4736), Envafolimab (KN035), CK-301, CS-1001, SHR-1316 (HTI-1088), CBT-502 (TQB-2450), BGB-A333, and BMS-986189. Non antibody peptide inhibitors can also be used, e.g., AUNP12, CA-170. See also Akinleye & Rasool, Journal of Hematology & Oncology 12:92 (2019) doi:10.1186/s13045-019-0779-5.

In some embodiments, the immunotherapeutic is or comprises an antigen binding portion of anti-PD-L1 antibody, e.g., single-chain variable fragment (scFv) antibodies against human PD-L1 protein (PD-L1.Hu); an exemplary sequence encoding an anti-PDL1 antibody scFv is shown in SEQ ID NO:105, or a portion thereof, e.g., lacking one, two or more of the signal peptide, HA-tag, and Myc-tag, e.g., comprising amino acids (aa) 31-513 of SEQ ID NO:105:

Exemplary anti-PDL1 scFv sequence (Signal peptide (aa 1-21); HA-tag, aa 21-30; Myc-tag, aa 514-523)

(SEQ ID NO: 105)

METDTLLLWVLLLWVPGSTGD*YPYDVPDYA*GAQPADDIQMTQSPSSLS

ASVGDRVTITCRASQDVSTAVAWYQQKPGKAPKLLIYSASFLYSGVPS

RFSGSGSGTDFTLTISSLQPEDFATYYCQQYLYHPATFGQGTKVEIKR

-continued

GGGGSGGGGSGGGGSEVQLVESGGGLVQPGGSLRLSCAASGFTFSDSW

IHWVRQAPGKGLEWVAWISPYGGSTYYADSVKGRFTISADTSKNTAYL

QMNSLRAEDTAVYYCARRHWPGGFDYWGQGTLVTVSAVDEAKSCDKTH

TCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCL

VKGFYPSDIAVEWESNGQPENNYKTTPPVLDSDGSFFLYSKLTVDKSR

WQQGNVFSCSVMHEALHNHYTQKSLSLSPGKVDEQKLISEEDLN.

The following is an exemplary antiPD-L1 nucleic acid sequence (Signal peptide (nt 1-63); HA-tag, nt 64-90; Myc-tag, nt 1540-1569

(SEQ ID NO: 106)

ATGGAGACAGACACACTCCTGCTATGGGTACTGCTGCTCTGGGTTCCA

GGTTCCACTGGTGAC*TATCCATATGATGTTCCAGATTATGCT*GGGGCC

CAGCCGGCCGACGACATCCAAATGACCCAGAGTCCATCTAGTCTGTCT

GCTTCGGTAGGTGATAGGGTCACTATTACTTGCAGGGCCTCCCAGGAC

GTGTCAACTGCAGTGGCTTGGTACCAACAGAAGCCCGGGAAAGCTCCC

AAACTGCTGATCTACTCCGCCAGCTTTCTGTATTCCGGAGTTCCGTCT

AGATTTTCCGGATCAGGAAGCGGCACGGATTTCACACTCACAATAAGC

AGCCTACAACCAGAGGACTTCGCAACCTACTATTGTCAACAGTACCTG

TACCATCCAGCCACCTTTGGGCAGGGCACCAAGGTGGAAATCAAGCGC

GGTGGTGGTGGATCAGGTGGAGGCGGAAGTGGAGGTGGCGGATCCGAA

GTTCAGCTTGTCGAGTCCGGTGGCGGCCTGGTTCAGCCTGGTGGGTCT

TTGCGTCTGTCATGCGCCGCCTCTGGTTTCACCTTTTCAGACTCTTGG

ATCCACTGGGTGAGACAGGCCCCAGGAAAGGGTCTTGAGTGGGTTGCA

TGGATTAGCCCCTACGGCGGCAGTACATATTACGCGGATAGCGTGAAA

GGGAGGTTTACCATCAGCGCAGACACGTCGAAGAACACCGCATACCTC

CAGATGAATTCCCTCCGAGCCGAAGATACCGCCGTGTACTATTGTGCT

CGCCGGCATTGGCCTGGCGGCTTCGATTATTGGGGACAGGGAACTCTA

GTAACAGTGTCGGCTGTCGACGAGGCCAAATCTTGTGACAAAACTCAC

ACATGCCCACCGTGCCCAGCACCCGAACTCCTGGGGGGACCGTCAGTC

TTCCTCTTCCCCCCAAAACCCAAGGACACCCTCATGATCTCCCGGACC

CCTGAGGTCACATGCGTGGTGGTGGACGTGAGCCACGAAGACCCTGAG

GTCAAGTTCAACTGGTACGTGGACGGCGTGGAGGTGCATAATGCCAAG

ACAAAGCCGCGGGAGGAGCAGTACAACAGCACGTACCGTGTGGTCAGC

GTCCTCACCGTCCTGCACCAGGACTGGCTGAATGGCAAGGAGTACAAG

TGCAAGGTCTCCAACAAAGCCCTCCCAGCCCCCATCGAGAAAACCATC

TCCAAAGCCAAGGGGCAGCCCCGAGAACCACAGGTGTACACCCTGCCC

CCATCCCGGGATGAGCTGACCAAGAACCAGGTCAGCCTGACCTGCCTG

GTCAAAGGCTTCTATCCCAGCGACATCGCCGTGGAGTGGGAGAGCAAT

-continued

GGGCAGCCGGAGAACAACTACAAGACCACGCCTCCCGTGCTGGACTCC

GACGGCTCCTTCTTCCTCTACAGCAAGCTCACCGTGGACAAGAGCAGG

TGGCAGCAGGGGAACGTCTTCTCATGCTCCGTGATGCATGAGGCTCTG

CACAACCACTACACGCAGAAGAGCCTCTCCCTGTCTCCGGGTAAAGTC

GACGAACAAAAATCATCTCAGAAGAAGATCTGAATTGA.

Other antibodies, as well as methods for generating a nucleic acid encoding such antibodies are known in the art; see, e.g., Li et al., Int J Mol Sci. 2016 July; 17(7): 1151; Engeland et al., Mol Ther. 2014 November; 22(11): 1949-1959 and the references above.

The virus can also include one or more sequences that promote expression of a transgene, e.g., one or more promoter sequences; enhancer sequences, e.g., 5' untranslated region (UTR) or a 3' UTR; a polyadenylation site; and/or insulator sequences. In some embodiments, the promoter is a brain tissue specific promoter, e.g., a neuron-specific or glia-specific promoter. In certain embodiments, the promoter is a promoter of a gene selected to from: neuronal nuclei (NeuN), glial fibrillary acidic protein (GFAP), MeCP2, adenomatous polyposis coli (APC), ionized calcium-binding adapter molecule 1 (Iba-1), synapsin I (SYN), calcium/calmodulin-dependent protein kinase II, tubulin alpha I, neuron-specific enolase and platelet-derived growth factor beta chain. In some embodiments, the promoter is a pan-cell type promoter, e.g., cytomegalovirus (CMV), beta glucuronidase, (GUSB), ubiquitin C (UBC), or rous sarcoma virus (RSV) promoter. The woodchuck hepatitis virus post-transcriptional response element (WPRE) can also be used. In some embodiments, a human signal or leader sequence, e.g., an IgK leader sequence is used. In some embodiments, a human signal sequence is used instead, as shown in the following table (Table adapted from novoprolabs.com/support/articles/commonly-used-leader-peptide-sequences-for-efficient-secretion-of-a-recombinant-protein-expressed-in-mammalian-cells-201804211337.html):

| Human Signal sequence | Sequence | SEQ ID NO: |
|---|---|---|
| Oncostatin M | MGVLLTQRTLLSLVLAL LFPSMASM | 107 |
| IgG2H | MGWSCIILFLVATATGVHS | 108 |
| Secrecon | MWWRLWWLLLLLLLLWPMVWA | 109* |
| IgKVIII | MDMRVPAQLLGLLLLWLRGARC | 110 |
| CD33 | MPLLLLLPLLWAGALA | 111 |
| tPA | MDAMKRGLCCVLLLCGA VFVSPS | 112 |
| Human Chymotrypsinogen | MAFLWLLSCWALLGTTFG | 113 |
| Human trypsinogen-2 | MNLLLILTFVAAAVA | 114 |
| Human IL-2 | MYRMQLLSCIALSLALVTNS | 115 |
| Albumin (HSA) | MKWVTFISLLFSSAYS | 116 |

-continued

| Human Signal sequence | Sequence | SEQ ID NO: |
|---|---|---|
| Human insulin | MALWMRLLPLLALLALW GPDPAAA | 117 |

*, Barash et al., Biochem Biophys Res Commun. 2002 Jun 21;294(4):835-42.

In some embodiments, a secretory sequence that promotes secretion of the antibody is used, e.g., as described in von Heijne, J Mol Biol. 1985 Jul. 5; 184(1):99-105; Kober et al., Biotechnol. Bioeng. 2013; 110: 1164-1173; Tsuchiya et al., Nucleic Acids Research Supplenzent No. 3 261-262 (2003).

In some embodiments, the AAV also has one or more additional mutations that increase delivery to the target tissue, e.g., the CNS, or that reduce off-tissue targeting, e.g., mutations that decrease liver delivery when CNS, heart, or muscle delivery is intended (e.g., as described in Pulicherla et al. (2011) Mol Ther 19:1070-1078); or the addition of other targeting peptides, e.g., as described in Chen et al. (2008) Nat Med 15:1215-1218 or Xu et al., (2005) Virology 341:203-214 or U.S. Pat. Nos. 9,102,949; 9,585,971; and US20170166926. See also Gray and Samulski (2011) "Vector design and considerations for CNS applications," in Gene Vector Design and Application to Treat Nervous System Disorders ed. Glorioso J., editor. (Washington, DC: Society for Neuroscience) 1-9, available at sfn.org/~/media/SfN/Documents/Short %20Courses/2011%20Short %20 Course %20I/2011_SC1_Gray.ashx.

Methods of Use

The methods and compositions described herein can be used to deliver an immunotherapeutic composition to a tissue, e.g., to the central nervous system (brain), heart, muscle, or dorsal root ganglion or spinal cord (peripheral nervous system). In some embodiments, the methods include delivery to specific brain regions, e.g., cortex, cerebellum, hippocampus, substantia nigra, or amygdala. In some embodiments, the methods include delivery to neurons, astrocytes, and/or glial cells.

In some embodiments, the methods and compositions, e.g., AAVs, are used to deliver a nucleic acid sequence encoding an immunotherapeutic to a subject who has brain cancer. Brain cancers include gliomas (e.g., glioblastoma multiforme (GBM)), metastases (e.g., from lung, breast, melanoma, or colon cancer), meningiomas, pituitary adenomas, and acoustic neuromas. Thus the methods can include systemically, e.g., intravenously, administering an AAV (e.g., AAV9) comprising a targeting peptide as described herein (e.g., AAV9 with a CPP 16 inserted therein, also referred to herein as AAV.CPP16) and encoding an immunotherapeutic to a subject who has been diagnosed with brain cancer.

In some embodiments, the methods also include co-administering a chemotherapeutic agent. In some embodiments, the chemotherapeutic agent is a toxin or cytotoxic drug, including but not limited to temozolamide, lomustine, or a combination thereof. See, e.g., Herrlinger et al., Lancet. 2019 Feb. 16; 393(10172):678-688. The methods can also include administering radiation, surgical resection, or both.

Pharmaceutical Compositions and Methods of Administration

The methods described herein include the use of pharmaceutical compositions comprising AAVs comprising (i) the targeting peptides and (ii) sequences encoding an immunotherapeutic as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intraarterial, subcutaneous, intraperitoneal intramuscular or injection or infusion administration. Delivery can thus be systemic or localized.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a kit, container, pack, or dispenser together with instructions for administration.

EXAMPLES

The invention is further described in the following examples, which do not limit the scope of the invention described in the claims.

Materials and Methods

The following materials and methods were used in the Examples below.

1. Generation of Capsid Variants

To generate the capsid variant plasmids, DNA fragments that encode the cell-penetrating peptides (Table 3) were synthesized (GenScript), and inserted into the backbone of the AAV9 Rep-cap plasmid (pRC9) between amino acid position 588 and 589 (VP1 amino acid numbering), using CloneEZ seamless cloning technology (GenScript). CPPs BIP1(VPALR, SEQ ID NO:1) and BIP2 (VSALK, SEQ ID NO:2), as well as their derivatives such as TVSALK (SEQ ID NO:4) in AAV.CPP.16 and TVSALFK (SEQ ID NO:8) in AAV.CPP.21, are derived from the Ku70 proteins, of which the sequences are provided as below:

```
Human Ku70 MSGWESYYKTEGDEEAEEEQEENLEASGDYKYSGRDSLIFLVDASKAMFESQSEDELTPE  60

Mouse Ku70 MSEWESYYKTEGEEEEEE--EESPDTGGEYKYSGRDSLIFLVDASRAMFESQGEDELTPF  58

Rat Ku70   MSEWESYYKTEGEEEEEE--EQSPDTNGEYKYSGRDSLIFLVDASRAMFESQGEDELTPF  58

Human Ku70 DMSIQCIQSVYISKIISSDRDLLAVVFYGTEKDKNSVNFKNIYVLQELDNPGAKRILELD 120

Mouse Ku70 DMSIQCIQSVYTSKIISSDRDLLAVVFYGTEKDKNSVNFKNIYVLQDLDNPGAKRVLELD 118
```

-continued

```
Rat Ku70   DMSIQCIQSVYTSKIISSDRDLLAVVFYGTEKDKNSVNFKSIYVLQDLDNPGAKRVLELD 118

Human Ku70 QFKGQQGQKRFQDMMGHGSDYSLSEVLWVCANLFSDVQFKMSHKRIMLFTNEDNPHGNDS 180

Mouse Ku70 QFKGQQGKKHFRDTVGHGSDYSLSEVLWVCANLFSDVQLKMSHKRIMLFTNEDDPHGRDS 178

Rat Ku70   RFKGQQGKKHFRDTIGHGSDYSLSEVLWVCANLFSDVQFKMSHKRIMLFTNEDDPHGNDS 178

Human Ku70 AKASRARTKAGDLRDTGIFLDLMHLKKPGGFDISLFYRDIISIAEDEDLRVHFEESSKLE 240

Mouse Ku70 AKASRARTKASDLRDTGIFLDLMHLKKPGGFDVSVFYRDIITTAEDEDLGVHFEESSKLE 238

Rat Ku70   AKASRARTKASDLRDTGIFLDLMHLKKRGGFDVSLFYRDIISIAEDEDLGVHFEESSKLE 238

Human Ku70 DLLRKVRAKETRKRALSRLKLKLNKDIVISVGIYNLVQKALKPPPIKLYRETNEPVKTKT 300

Mouse Ku70 DLLRKVRAKETKKRVLSRLKFKLGEDVVLMVGIYNLVQKANKPFPVRLYRETNEPVKTKT 298

Rat Ku70   DLLRKVRAKETKKRVLSRLKFKLGKDVALMVGVYNLVQKANKPFPVRLYRETNEPVKTKT 298

Human Ku70 RTFNTSTGGLLLPSDTKRSQIYGSRQIILEKEETEELKRFDDPGLMLMGFKPLVLLKKHH 360

Mouse Ku70 RTFNVNTGSLLLPSDTKRSLTYGTRQIVLEKEETEELKRFDEPGLILMGFKPTVMLKKQH 358

Rat Ku70   RTFNVNTGSLLLPSDTKRSLTFGTRQIVLEKEETEELKRFDEPGLILMGFKPMVMLKNHH 358

Human Ku70 YLRPSLFVYPEESLVIGSSTLFSALLIKCLEKEVAALCRYTPRRNIPPYFVALVPQEEEL 420

Mouse Ku70 YLRPSLFVYPEESLVSGSSTLFSALLTKCVEKEVIAVCRYTPRKNVSPYFVALVPQEEEL 418

Rat Ku70   YLRPSLFLYPEESLVNGSSTLFSALLTKCVEKEVIAVCRYTARKNVSPYFVALVPQEEEL 418

Human Ku70 DDQKIQVTPPGFQLVFLPFADDKRKMPFTEKIMATPEQVGKMKAIVEKLRFTYRSDSFEN 480

Mouse Ku70 DDQNIQVTPGGFQLVFLPYADDKRKVPFTEKVTANQEQIDKMKAIVQKLRFTYRSDSFEN 478

Rat Ku70   DDQNIQVTPAGFQLVFLPYADDKRKVPFTEKVMANPEQIDKMKAIVQKLRFTYRSDSFEN 478

Human Ku70 PVLQQHFRNLEALALDLMEPEQAVDLTLPKVEAMNKRLGSLVDEFKELVYPPDYNPEGKV 540

Mouse Ku70 PVLQQHFRNLEALALDMMESEQVVDLTLPKVEAIKKRLGSLADEFKELVYPPGYNPEGKV 538

Rat Ku70   PVLQQHFRNLEALALDMMESEQVVDLTLPKVEAIKKRLGSLADEFKELVYPPGYNPEGKI 538

Human Ku70 TKRKHDNEGSGSKRPKVEYSEEELKTHISKGTLGKFTVPMLKEACRAYGLKSGLKKQELL 600

Mouse Ku70 AKRKQDDEGSTSKKPKVELSEEELKAHFRKGTLGKLTVPTLKDICKAHGLKSGPKKQELL 598

Rat Ku70   AKRKADNEGSASKKPKVELSEEELKDLFAKGTLGKLTVPALRDICKAYGLKSGPKKQELL 598

                                                             (SEQ ID NO: 86)
Human Ku70 EALTKHFQD-                                                  609

                                                             (SEQ ID NO: 87)
Mouse Ku70 DALIRHLEKN                                                  608

                                                             (SEQ ID NO: 88)
Rat Ku70 EALSRHLEKN                                                    608
```

In addition, VP1 protein sequences for AAV9, AAV.CPP.16 and AAV.CPP.21 are provided as below:

```
AAV9       MAADGYLPDWLEDNLSEGIREWWALKPGAPQPKANQQHQDNARGLVLPGYKYLGPGNGLD  60

AAV.CPP16  MAADGYLPDWLEDNLSEGIREWWALKPGAPQPKANQQHQDNARGLVLPGYKYLGPGNGLD  60

AAV.CPP21  MAADGYLPDWLEDNLSEGIREWWALKPGAPQPKANQQHQDNARGLVLPGYKYLGPGNGLD  60

AAV9       KGEPVNAADAAALEHDKAYDQQLKAGDNPYLKYNHADAEFQERLKEDTSFGGNLGRAVFQ 120

AAV.CPP16  KGEPVNAADAAALEHDKAYDQQLKAGDNPYLKYNHADAEFQERLKEDTSFGGNLGRAVFQ 120

AAV.CPP21  KGEPVNAADAAALEHDKAYDQQLKAGDNPYLKYNHADAEFQERLKEDTSFGGNLGRAVFQ 120

AAV9       AKKRLLEPLGLVEEAAKTAPGKKRPVEQSPQEPDSSAGIGKSGAQPAKKRLNFGQTGDTE 180

AAV.CPP16  AKKRLLEPLGLVEEAAKTAPGKKRPVEQSPQEPDSSAGIGKSGAQPAKKRLNFGQTGDTE 180
```

-continued

```
AAV.CPP21 AKKRLLEPLGLVEEAAKTAPGKKRPVEQSPQEPDSSAGIGKSGAQPAKKRLNFGQTGDTE 180

AAV9      SVPDPQPIGEPPAAPSGVGSLTMASGGGAPVADNNEGADGVGSSSGNWHCDSQWLGDRVI 240

AAV.CPP16 SVPDPQPIGEPPAAPSGVGSLTMASGGGAPVADNNEGADGVGSSSGNWHCDSQWLGDRVI 240

AAV.CPP21 SVPDPQPIGEPPAAPSGVGSLTMASGGGAPVADNNEGADGVGSSSGNWHCDSQWLGDRVI 240

AAV9      TTSTRTWALPTYNNHLYKQISNSTSGGSSNDNAYFGYSTPWGYFDFNRFHCHFSPRDWQR 300

AAV.CPP16 TTSTRTWALPTYNNHLYKQISNSTSGGSSNDNAYFGYSTPWGYFDFNRFHCHFSPRDWQR 300

AAV.CPP21 TTSTRTWALPTYNNHLYKQISNSTSGGSSNDNAYFGYSTPWGYFDFNRFHCHFSPRDWQR 300

AAV9      LINNNWGFRPKRLNFKLFNIQVKEVTDNNGVKTIANNLTSTVQVFTDSDYQLPYVLGSAH 360

AAV.CPP16 LINNNWGFRPKRLNFKLFNIQVKEVTDNNGVKTIANNLTSTVQVFTDSDYQLPYVLGSAH 360

AAV.CPP21 LINNNWGFRPKRLNFKLFNIQVKEVTDNNGVKTIANNLTSTVQVFTDSDYQLPYVLGSAH 360

AAV9      EGCLPPFPADVFMIPQYGYLTLNDGSQAVGRSSFYCLEYFPSQMLRTGNNFQFSYEFENV 420

AAV.CPP16 EGCLPPFPADVFMIPQYGYLTLNDGSQAVGRSSFYCLEYFPSQMLRTGNNFQFSYEFENV 420

AAV.CPP21 EGCLPPFPADVFMIPQYGYLTLNDGSOAVGRSSFYCLEYFPSOMLRTGNNFQPSYEFENV 420

AAV9      PFHSSYAHSQSLDRLMNPLIDQYLYYLSKTINGSGQNQQTLKFSVAGPSNMAVQGRNYIP 480

AAV.CPP16 PFHSSYAHSQSLDRLMNPLIDQYLYYLSKTINGSGQNQQTLKFSVAGPSNMAVQGRNYIP 480

AAV.CPP21 PFHSSYAHSQSLDRLMNPLIDQYLYYLSKTINGSGQNQQTLKFSVAGPSNMAVQGRNYIP 480

AAV9      GPSYRQQRVSTTVTQNNNSEFAWPGASSWALNGRNSLMNPGPAMASHKEGEDRFFPLSGS 540

AAV.CPP16 GPSYRQQRVSTTVTQNNNSEFAWPGASSWALNGRNSLMNPGPAMASHKEGEDRFFPLSGS 540

AAV.CPP21 GPSYRQQRVSTTVTONNNSEFAWPGASSWALNGRNSLMNPGPAMASHKEGEDRFFPLSGS 540

AAV9      LIFGKQGTGRDNVDADKVMITNEEEIKTTNPVATESYGQVATNHQSAQ-------AQAQT 593

AAV.CPP16 LIFGKQGTGRDNVDADKVMITNEEEIKTTNPVATESYGQVATNHQSAQTVSAL-KAQAQT 599

AAV.CPP21 LIFGKQGTGRDNVDADKVMITNEEEIKTTNPVATESYGQVATNHQSAQTVSALFKAQAQT 600

AAV9      GWVQNQGILPGMVWQDRDVYLQGPIWAKIPHTDGNFHPSPLMGGFGMKHPPPQILIKNTP 653

AAV.CPP16 GWVQNQGILPGMVWQDRDVYLQGPIWAKIPHTDGNFHPSPLMGGFGMKHPPPQILIKNTP 659

AAV.CPP21 GWVQNQGILPGMVWQDRDVYLQGPIWAKIPHTDGNFHPSPLMGGFGMKHPPPQILIKNTP 660

AAV9      VPADPPTAFNKDKLNSFITQYSTGQVSVEIEWELQKENSKRWNPEIQYTSNYYKSNNVEF 713

AAV.CPP16 VPADPPTAFNKDKLNSFITQYSTGQVSVEIEWELQKENSKRWNPEIQYTSNYYKSNNVEF 719

AAV.CPP21 VPADPPTAFNKDKLNSFITQYSTGQVSVEIEWELQKENSKRWNPEIQYTSNYYKSNNVEF 720

                                                                 (SEQ ID NO: 85)
AAV9 AVNTEGVYSEPRPIGTRYLTRNL                                          736
                                                                 (SEQ ID NO: 89)
AAV.CPP16 AVNTEGVYSEPRPIGTRYLTRNL                                     742
                                                                 (SEQ ID NO: 90)
AAV.CPP21 AVNTEGVYSEPRPIGTRYLTRNL                                     743
```

2. Recombinant AAV Production

Recombinant AAVs were packaged using standard three-plasmid co-transfection protocol (pRC plasmid, pHelper plasmid and pAAV plasmid). pRC9 (or its variant), pHelper and pAAV carrying a transgene (e.g. nucleus-directed RFP H2B-mCherry driven by an ubiquitous EF1a promoter) were co-transfected into HEK 293T cells using polyethylenimine (PEI, Polysciences). rAAVs vectors were collected from serum-free medium 72 h and 120 h post transfection and from cell at 120 h post transfection. AAV particles in the medium were concentrated using a PEG-precipitation method with 8% PEG-8000 (wt/vol). Cell pellets containing viral particles were resuspended and lysed through sonication. Combined viral vectors from PEG-precipitation and cell lysates were treated with DNase and RNase at 37° C. for 30 mins and then purified by iodixanol gradient (15%, 25%, 40% and 60%) with ultracentrifugation (VTi 50 rotor, 40,000 r.p.m, 18° C., 1 h). rAAVs were then concentrated using Millipore Amicon filter unit (UFC910008, 100K MWCO) and formulated in Dulbecco's phosphate buffered saline (PBS) containing 0.001% Pluronic F68 (Gibco).

3. AAV Titering

Virus titer was determined by measuring DNase-resistant genome copies using quantitative PCR. pAAV-CAG-GFP was digested with PVUII (NEB) to generate free ends for the plasmid ITRs, and was used for generating a standard curve. Virus samples were incubated with DNase I to eliminate contaminating DNA, followed by sodium hydroxide treatment to dissolve the viral capsid and to release the viral genome. Quantitative PCR was performed using an ITR Forward primer 5'-GGAACCCCTAGTGATGGAGTT (SEQ ID NO:91) and an ITR Reverse primer 5'-CGGCCTCAGTGAGCGA (SEQ ID NO:92). Vector titers were normalized to the rAAV-2 reference standard materials (RSMs, ATCC, cat No:VR-1616, Manassas, VA).

4. Administration of AAV in Mice

For intravenous administration, AAV diluted in sterile saline (0.2 ml) was administered through tail vein injection in adult mice (over 6 weeks of age). Animals then survived for three weeks before being euthanized for tissue harvesting. For intracerebral injection, AAV diluted in PBS (10 ul) was injected using a Hamilton syringe with coordinates from bregma: 1.0 mm right, 0.3 backward, 2.6 mm deep. All animal studies were performed in an AAALAC-accredited facility with IACUC approval.

5. Mouse Tissue Processing

Anesthetized animals were transcardially perfused with cold phosphate buffered saline (PBS) followed by 4% paraformaldehyde (PFA). Tissues were post-fixed in 4% PFA overnight, and then immersed in 30% sucrose solutions for two days prior to embedding and snap-freezing in OCT. Typically, 80 um thick brain sections were cut for imaging of native fluorescence, 40 um thick brain sections for IHC.

6. In Vitro Human BBB Spheroid Model

Hot 1% agarose (w/v, 50 ul) was added in a 96-well plate to cool/solidify. Primary human astrocytes (Lonza Bioscience), human brain microvascular pericytes (HBVP, ScienCell Research Laboratories) and human cerebral microvascular endothelial cells (hCMEC/D3; Cedarlane) were then seeded onto the agarose gel in a 1:1:1 ratio (1500 cells of each type). Cells were cultured at 37° C. in a 5% CO2 incubator for 48-72 hours to allow for spontaneous assembly of multicellular BBB spheroids. A multicellular barrier was reported to form at the periphery of the spheroid, mimicking the BBB. AAVs-H2B-mCherry were added to the culture medium, and 4 days later all spheroids were fixed using 4% PFA, transferred into a Nunc Lab-Tek II thin-glass 8-well chambered coverglass (Thermo Scientific), and imaged using a Zeiss LSM710 confocal microscope. The intensity of RFP signal inside the spheroids was examined and used as a "read-out".

7. AAV Administration in Non-Human Primate (NHP)

All NHP studies were performed by a CRO in an AAALAC-accredited facility with IACUC approval. Cynomolgus monkeys were pre-screened for little or no pre-existing neutralizing antibody against AAV9 (titer of <1:5). AAV diluted in PBS/0.001% F68 was injected intravenously (via cephalic vein or femoral vein) using a peristaltic pump. 3 weeks later, animals were subject to transcardial perfusion with PBS, followed by 4% PFA. Tissues were then collected and processed for paraffin embedding and sectioning.

8. Immunohistochemistry le;.3qFloating staining was performed for mouse tissue sections with primary antibodies diluted in PBS containing 10% donkey serum and 2% Triton X-100. Primary antibodies used include: chicken anti-GFP (1:1000); rabbit anti-RFP (1:1000); mouse anti-NeuN (1:500); rat anti-GFAP (1:500); Goat anti-GFAP (1:500); mouse anti-CD31 (1:500). Secondary antibodies conjugated to fluorophores of Alexa Fluor 488, Alexa Fluor 555 or Alexa Fluor 647 were applied against the primary antibody's host species at a dilution of 1:200.

For paraffin sections of NHP tissue, DAB staining was performed to visualize cells transduced by AAV-AADC. Rabbit anti-AADC antibody (1:500, Millipore) was used as primary antibody.

9. AAV Binding Assay

HEK293T cells were cultured at 37° C. in a 5% CO2 incubator. One day after seeding of HEK293T cells in a 24-well plate at a density of 250,000 cells per well, a cDNA plasmid of LY6A was transiently transfected into the cells using a transfection mixture of 200 ul DMEM (31053028; Gibco), 1 ug DNA plasmid and 3 ug of PEI. 48 hours post transfection, cells were placed on ice to chill down for 10 mins. The medium was then changed with 500 ul ice-cold serum-free DMEM medium containing rAAVs-mCherry at MOI of 10000. After incubating on ice for one hour, cells with presumably AAVs bound to their surface were washed with cold PBS for three times and were then subject to genomic DNA isolation. Cell-binding viral particles were quantified by using qPCR with primers specific to mCherry and normalized to HEK293T genomes using human GCG as reference.

10. Mouse Model of Glioblastoma

All experiments were performed in compliance with protocols approved by the Animal Care and Use Committees (IACUC) at the Brigham and Women's Hospital and Harvard Medical School. Syngeneic immuno-competent C57BL/6 female mice weighing 20+/−1 g (Envigo) were used. GL261-Luc (100,000 mouse glioblastoma cells) resuspended in 2 μL phosphate buffered saline (PBS) was injected intracranially using 10 μl syringe with a 26-gauge needle (80075; Hamilton). A stereotactic frame was used to locate the implantation site (coordinates from bregma in mm: 2 right, 0.5 forward, at a depth of 3.5 into cortex). 7 days later, 200 ul AAV-HSV-TK1 (1E+12 viral genomes, IV) was administered once and ganciclovir (50 mg/kg) was administered daily for 10 days.

Example 1. Modification of AAV9 Capsid

Figure 1B:
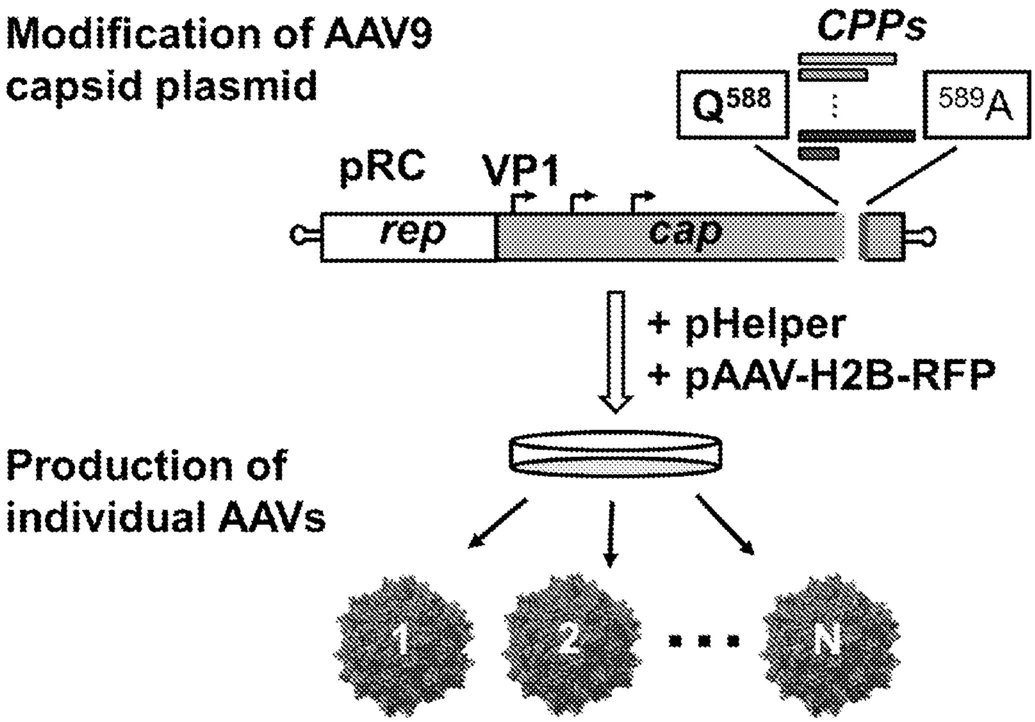

To identify peptide sequences that would enhance permeation of a biomolecule or virus across the blood brain barrier an AAV peptide display technique was used, individual cell-penetrating peptides, as listed in Table 3, were inserted into the AAV9 capsid between amino acids 588 and 589 (VP1 numbering) as illustrated in FIG. 1A. The insertion was carried out by modifying the RC plasmid, one of the three plasmids co-transfected for AAV packaging; FIG. 1B shows an exemplary schematic of the experiments. Individual AAV variants were produced and screened separately. See Materials and Methods #1-3 for more details.

TABLE 3

| | AAV | Name of CPP insert | Amino acid sequence of CPP | # | No. of CPP residues | Viral titer |
|---|---|---|---|---|---|---|
| Initial Screening | AAV9 | N/A | N/A | | N/A | Normal |
| | AAV.CPP.1 | SynB1 | RGGRLSYSRRRFSTSTGR | 93 | 18 | Low |
| | AAV.CPP.2 | L-2 | HARIKPTFRRLKWKY KGKFW | 94 | 20 | Low |

TABLE 3-continued

| | AAV | Name of CPP insert | Amino acid sequence of CPP | # | No. of CPP residues | Viral titer |
|---|---|---|---|---|---|---|
| | AAV.CPP.3 | PreS2-TLM | PLSSIFSRIGDP | 95 | 12 | Low |
| | AAV.CPP.4 | Transportan 10 | AGYLLGKINLKALAA LAKKIL | 96 | 21 | Low |
| | AAV.CPP.5 | SAP | VRLPPPVRLPPPVRLPPP | 97 | 18 | Normal |
| | AAV.CPP.6 | SAP(E) | VELPPPVELPPPVELPPP | 98 | 18 | Normal |
| | AAV.CPP.7 | SVM3 | KGTYKKKLMRIPLKGT | 99 | 16 | Low |
| | AAV.CPP.8 | (PPR)3 | PPRPPRPPR | 100 | 9 | Normal |
| | AAV.CPP.9 | (PPR)5 | PPRPPRPPRPPRPPR | 101 | 15 | Low |
| | AAV.CPP.10 | Poly-arginine | RRRRRRRR | 102 | 8 | Low |
| | AAV.CPP.11 | Bip1 | VPALR | 1 | 5 | Normal |
| | AAV.CPP.12 | Bip2 | VSALK | 2 | 5 | Normal |
| | AAV.CPP.13 | DPV15 | LRRERQSRLRRERQSR | 103 | 16 | NA |
| | AAV.CPP.14 | HIV-1 Tat | RKKRRQRRR | 104 | 9 | NA |
| Follow-up Screening | AAV.CPP.15 | Bip1.1 | TVPALR (Rat) | 3 | 6 | Normal |
| | AAV.CPP.16 | Bip2.1 | TVSALK (Syn) | 4 | 6 | Normal |
| | AAV.CPP.17 | Bip2.2 | FTVSALK (Syn) | 5 | 7 | Normal |
| | AAV.CPP.18 | Bip2.3 | LTVSALK (Syn) | 6 | 7 | Normal |
| | AAV.CPP.19 | Bip2.4 | KFTVSALK (Syn) | 72 | 8 | Normal |
| | AAV.CPP.20 | Bip2.5 | TFVSALK (Syn) | 7 | 7 | Normal |
| | AAV.CPP.21 | Bip2.6 | TVSALFK (Syn) | 8 | 7 | Normal |
| | AAV.CPP.22 | Bip2.6Rat | TVPALFR (Rat) | 9 | 7 | Normal |

SEQ ID NO:
Syn synthetic

Example 2. First Round of In Vivo Screening

Figure 2A:
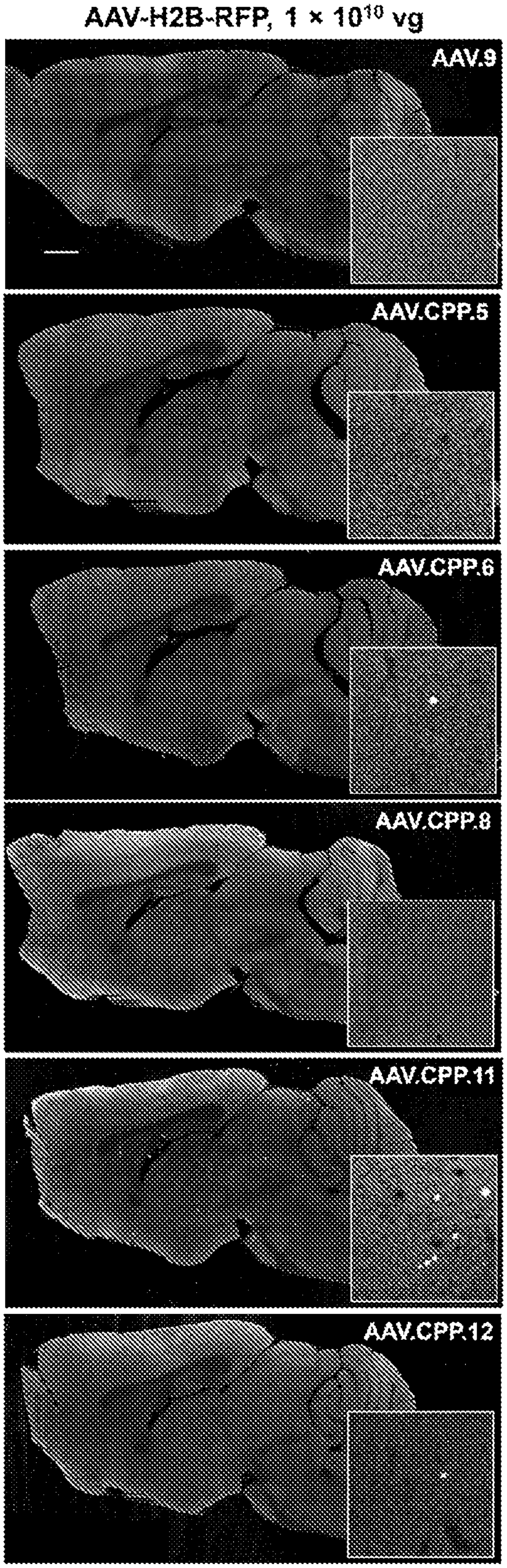
FIGS. 2A-2B depict representative images of mouse brain sections (FIG. 2A) and their quantitative analysis (FIG. 2B) after intravenous administration of low-dose candidate AAVs. Mice with mixed genetic background are used. Candidate AAVs differs in their inserted CPPs (see Table 3), but all express nuclear red fluorescent protein (RFP) as reporter. Candidate AAVs with low production yields are excluded for further screening. The dose of AAV is $1\times10^{10}$ vg (viral genome) per animal. Each white dot in FIG. 2A represents a RFP-labeled cell.
Figure 2B:
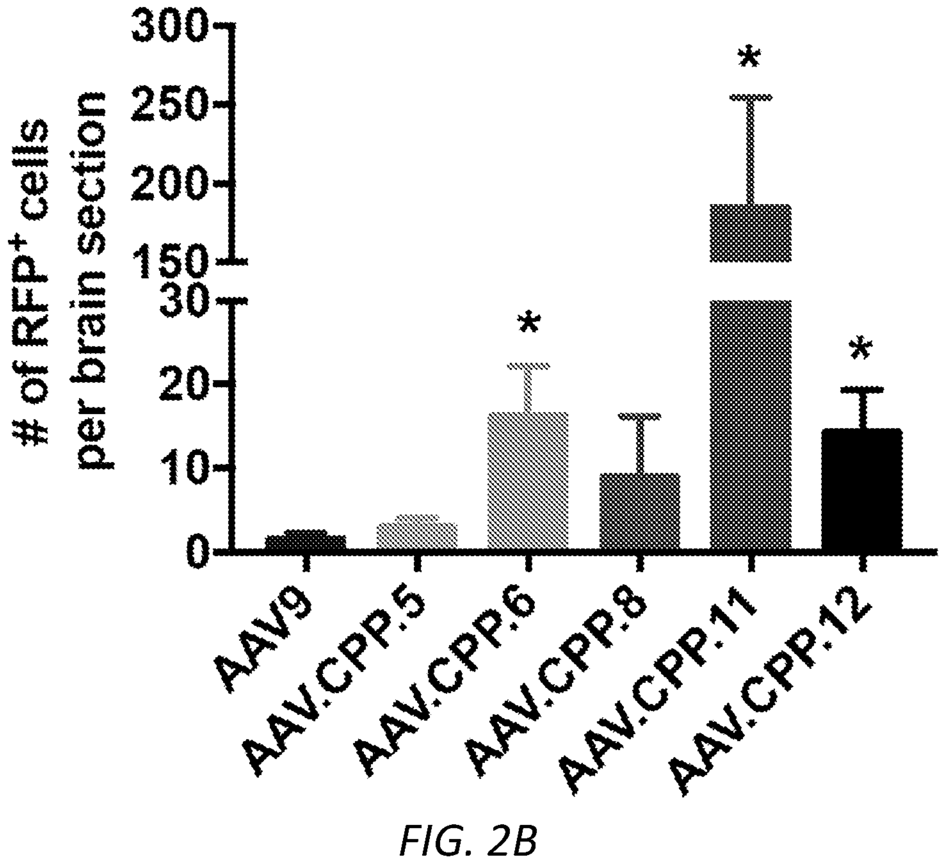
Figure 2C:
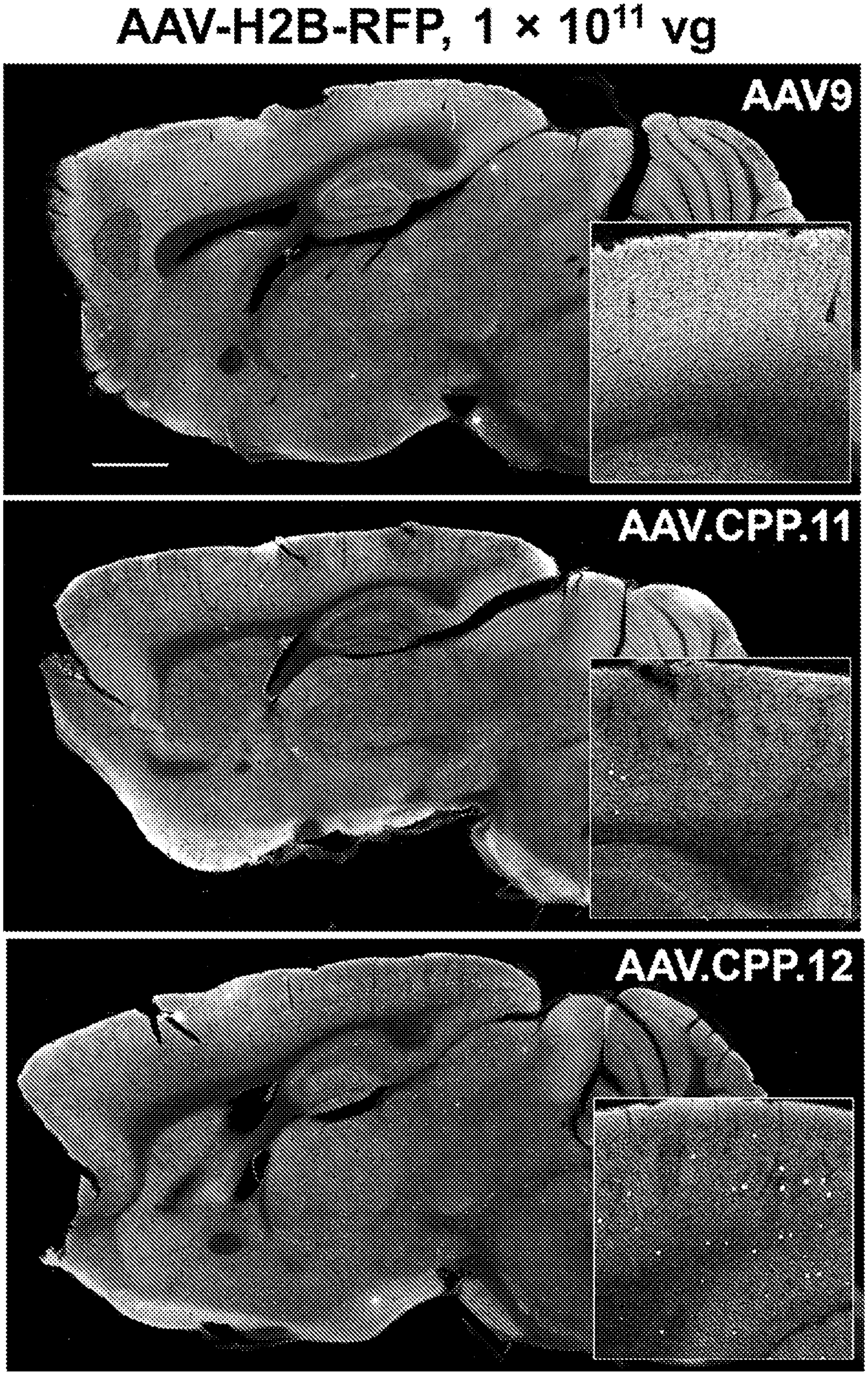
FIGS. 2C-2D depict representative images of mouse brain sections (FIG. 2C) and their quantitative analysis (FIG. 2D) after intravenous administration of AAV.CPP.11 and AAV.CPP.12 in a repeat experiment. AAV.CPP.11 and AAV.CPP.12 contain CPPs BIP1 and BIP2 respectively (see Table 3). The doses of the AAVs are increased to $1\times10^{11}$ vg per animal. Candidate AAVs express nuclear red fluorescent protein (RFP) as reporter. Each white dot in FIG. 2C represents a RFP-labeled cell.
Figure 2D:
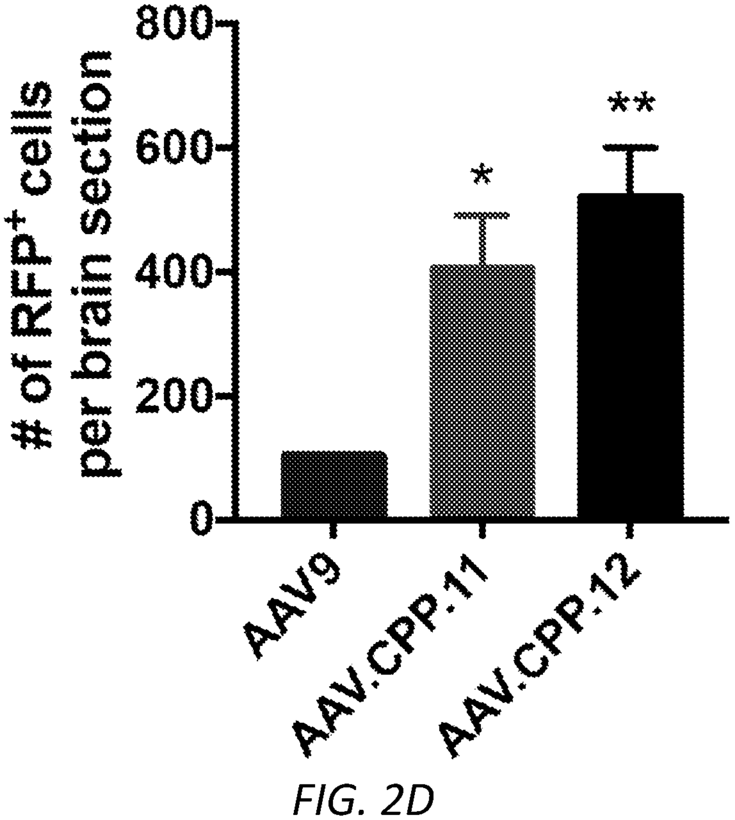

AAVs expressing nuclear RFP (H2B-RFP) were injected intravenously in adult mice with mixed C57BL/6 and BALB/c genetic background. 3 weeks later, brain tissues were harvested and sectioned to reveal RFP-labelled cells (white dots in FIGS. 2A and 2C, quantified in FIGS. 2B and 2D, respectively). CPPs BIP1 and BIP2 were inserted into the capsids of AAV.CPP.11 and AAV.CPP.12, respectively. See Materials and Methods #4-5 for more details.

Example 3. Optimization of Modified AAV9 Capsids

Figure 3A:
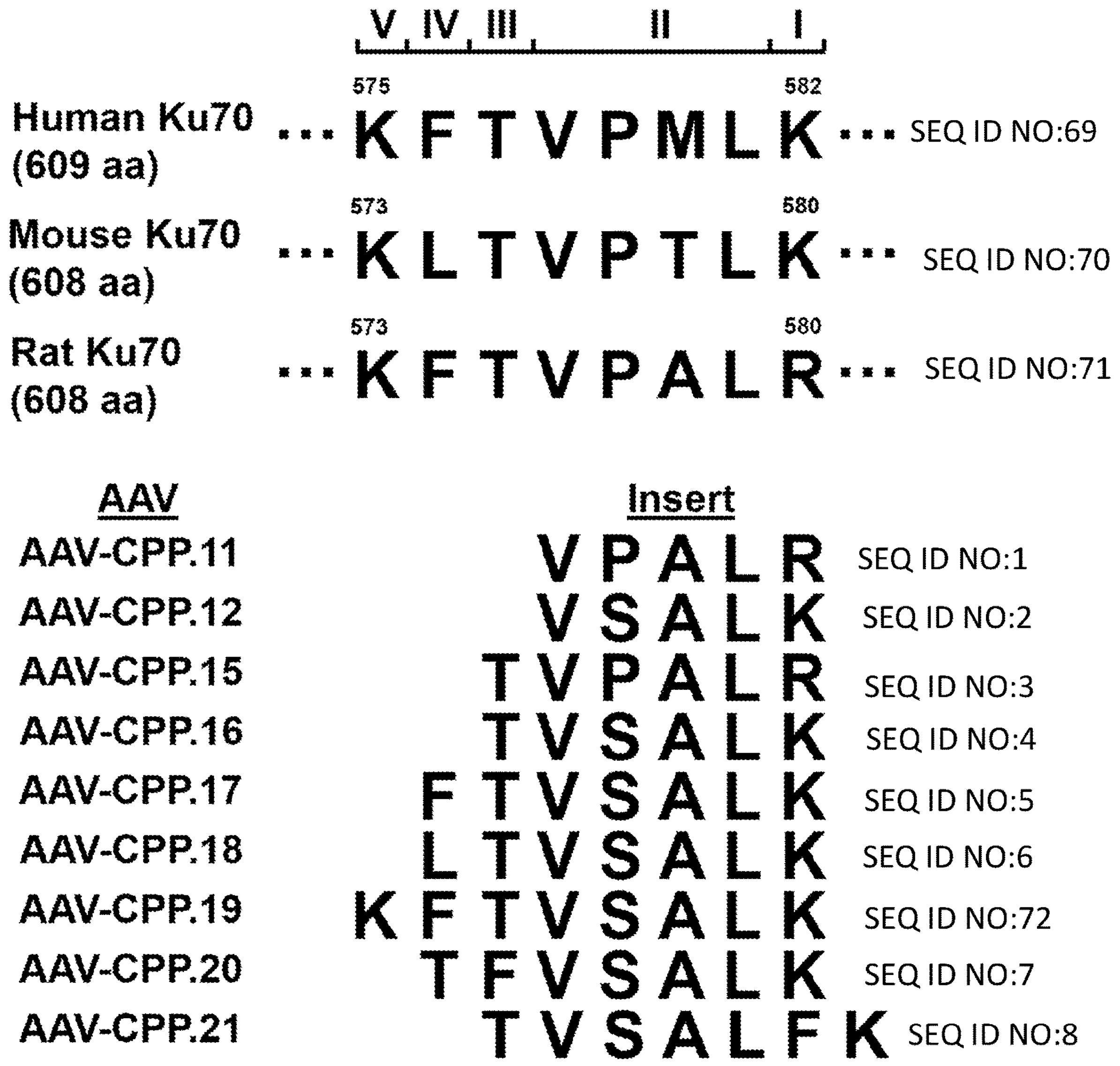
FIG. 3A depicts the optimization of the BIP targeting sequence in order to further engineer AAV9 towards better brain transduction. BIP1 (VPALR, SEQ ID NO:1), which enables AAV9 to transduce brain more efficiently (as in AAV.CPP.11), is derived from the protein Ku70 in rats. Human, mouse and rat Ku70 proteins differ in their exact amino acid sequences. BIP2 (VSALK, SEQ ID NO:2) as in AAV.CPP.12 is a "synthetic" peptide related to BIP1. Further engineering focuses on the VSALK sequence in the hope of minimizing species specificity of final engineered AAV. To generate new targeting sequence, amino acids of interest are added to the VSALK sequence, and in other cases positions of individual amino acids are switched. All new BIP2-derived sequences are again inserted into the AAV9 capsid to generate new candidate AAVs for screening. Sequences appearing in order are SEQ ID NOs: 69, 70, 71, 1-6, 72, 7, and 8.
Figure 3B:
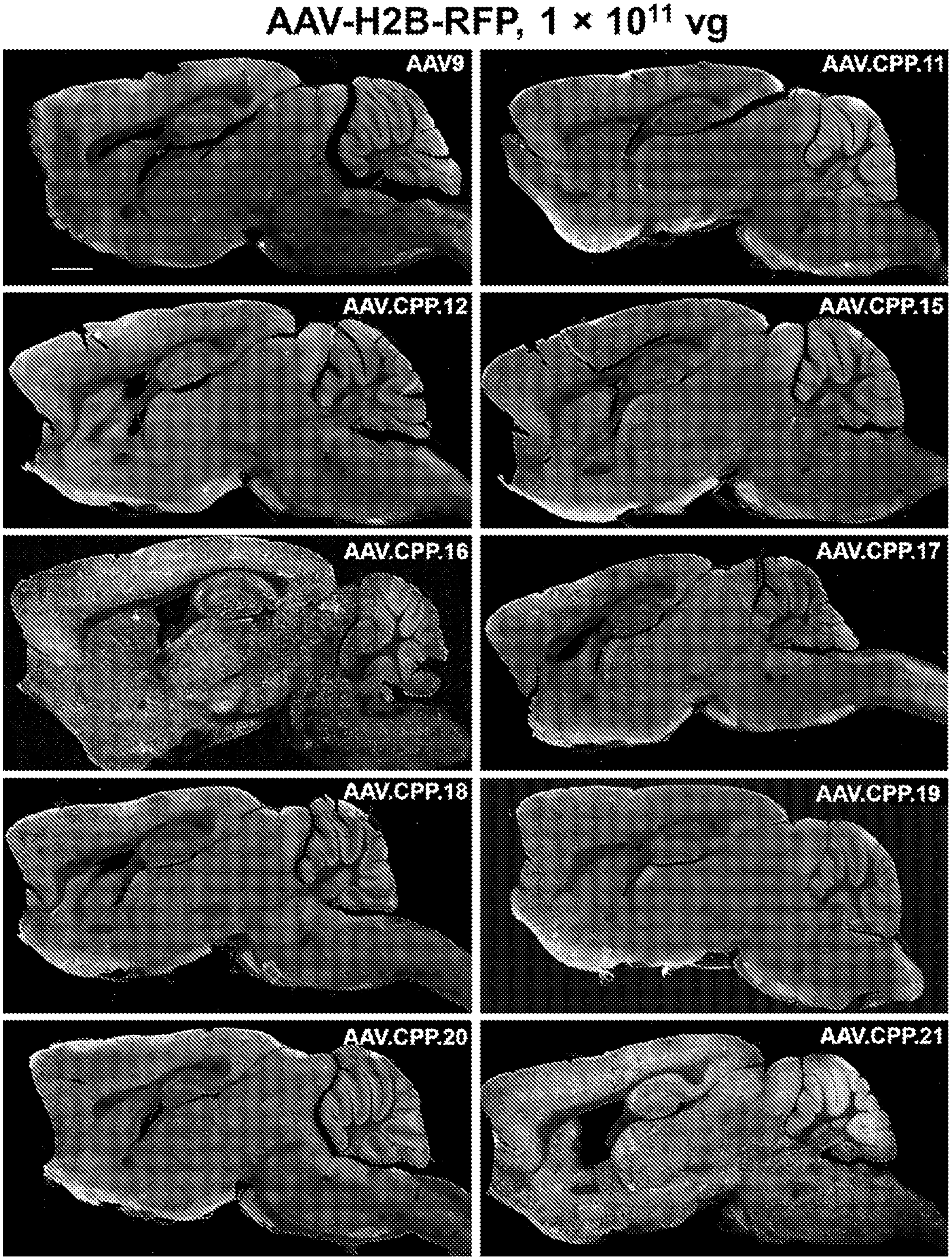
FIGS. 3B-3C depict representative images of mouse brain sections (FIG. 3B) and their quantitative analysis (FIG. 3C) after intravenous administration of more candidate AAVs. All candidate AAVs express nuclear red fluorescent protein (RFP) as reporter. The dose of AAV is $1\times10^{11}$ vg per animal. Each white dot in FIG. 3B represents a RFP-labeled cell. AAV.CPP.16 and AAV.CPP.21 were identified as top hits with their robust and widespread brain transduction.
Figure 3C:
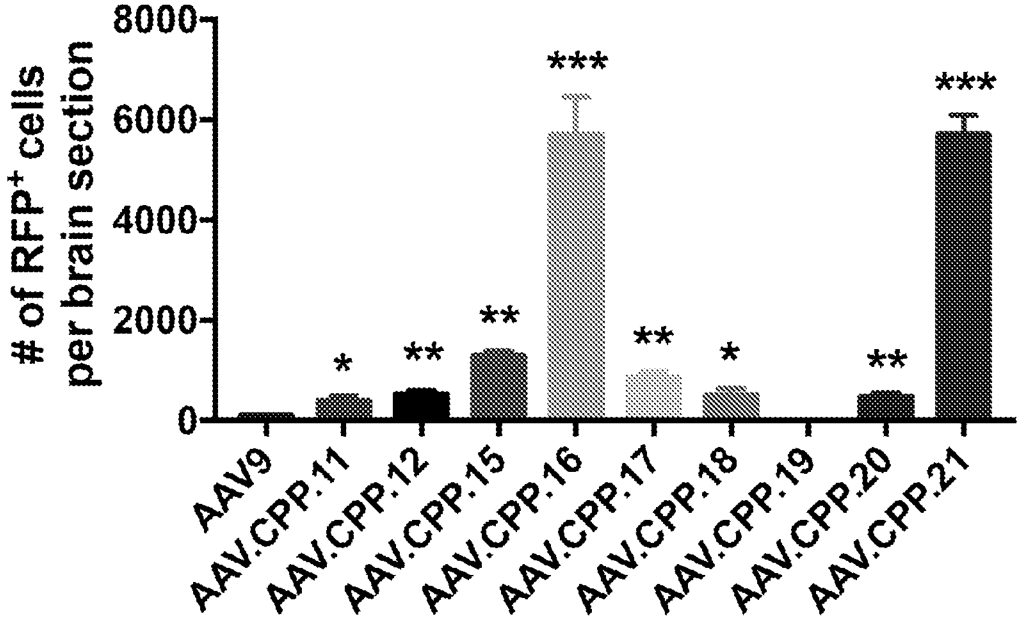
Figure 3D:
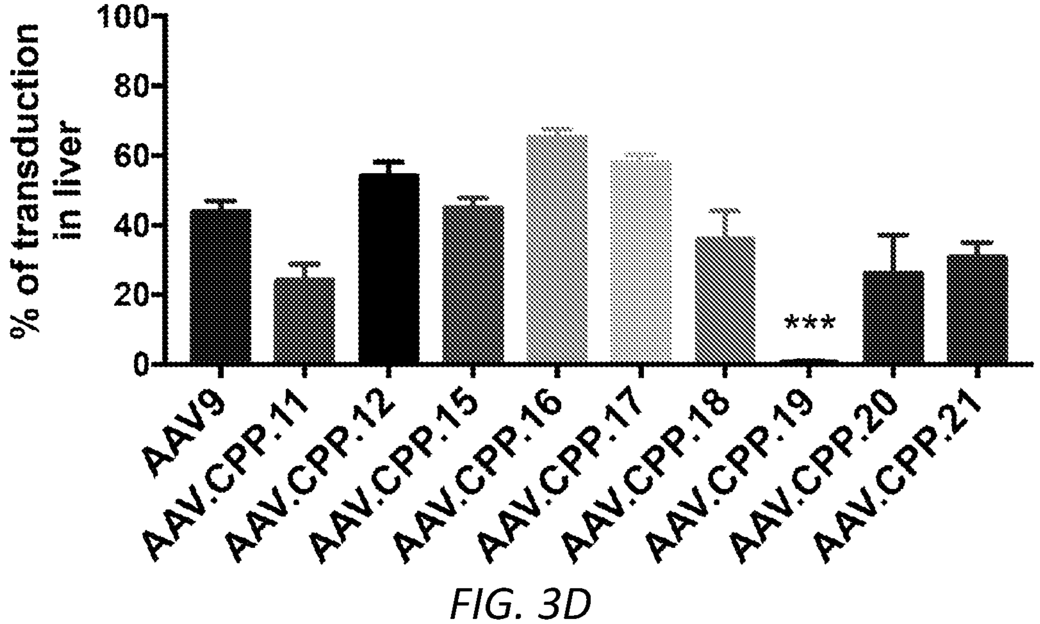
FIG. 3D depicts quantitative analysis of transduction efficiency in the liver after intravenous administration of candidate AAVs. Percentage of transduced liver cells is presented. The dose of AAV is $1\times10^{11}$ vg per animal. *** $P<0.001$, vs. AAV9, ANOVA.

AAV.CPP.11 and AAV.CPP.12 were further engineered by optimizing the BIP targeting sequences. BIP inserts were derived from the protein Ku70 (See FIG. 3A and Material/Methods #1 for full sequence). The BIP sequence VSALK, which is of "synthetic" origin, was chosen as a study focus to minimize potential species specificity of engineered AAV vectors. AAVs were produced and tested separately for brain transduction efficiency as compared with AAV9 (see FIGS. 3B-C). Percentages of cell transduction in the mouse liver 3 weeks after IV injection of some AAV variants delivering the reporter gene RFP are shown in FIG. 3D. See Materials and Methods #1-5 for more details.

Example 4. In Vitro Model—BBB Permeation Screening

Figure 4A:
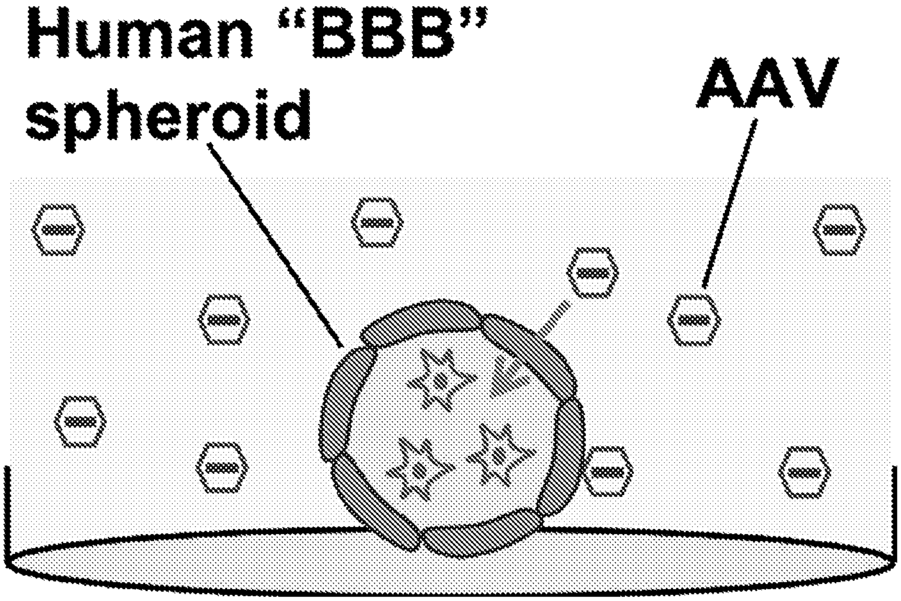
FIGS. 4A-4E depict screening of selected candidate AAVs in an in vitro spheroid model of human blood-brain barrier.
Figure 4B:
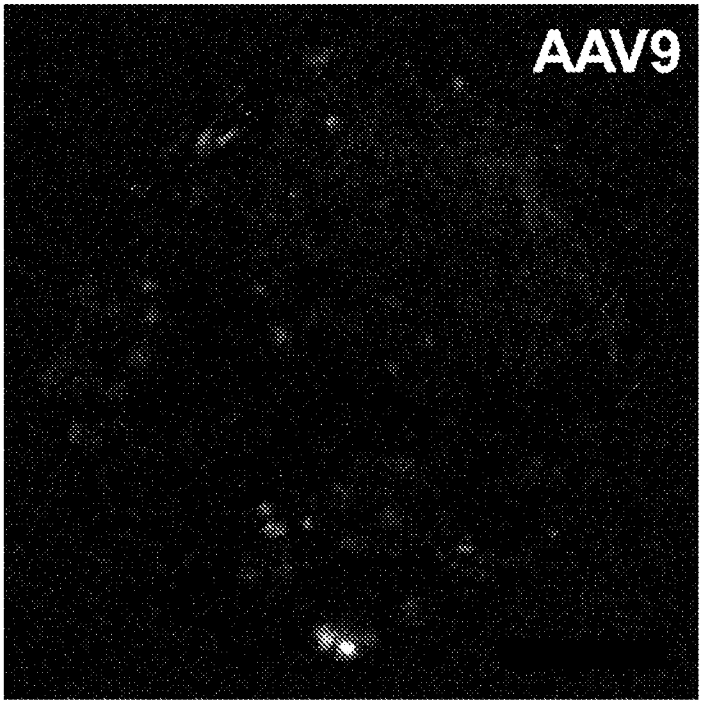
Figure 4C:
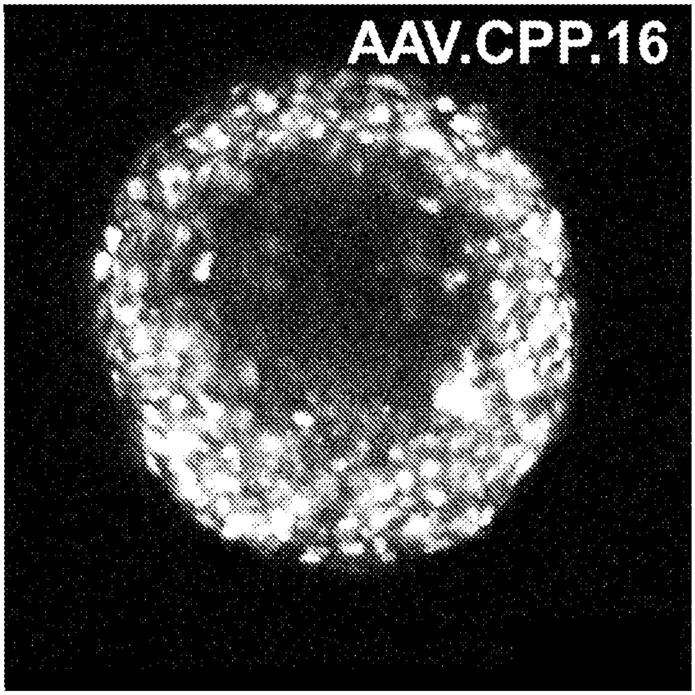
Figure 4D:
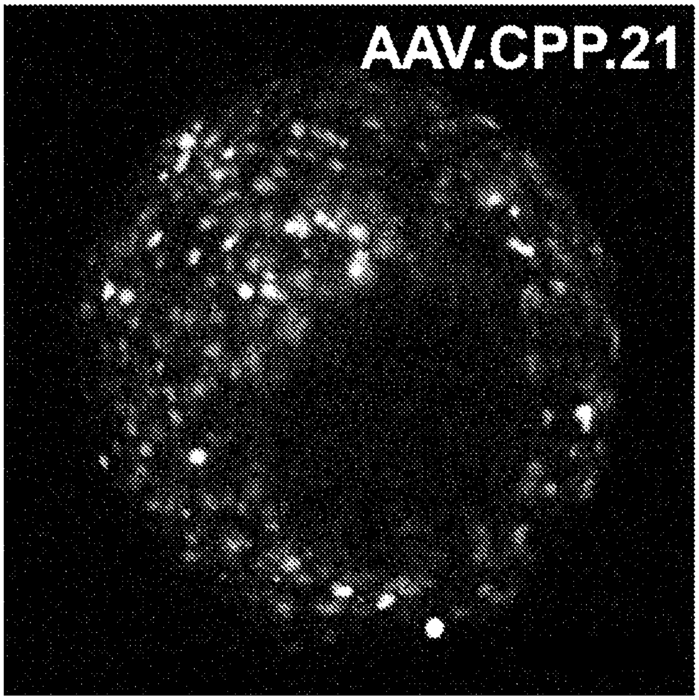
Figure 4E:
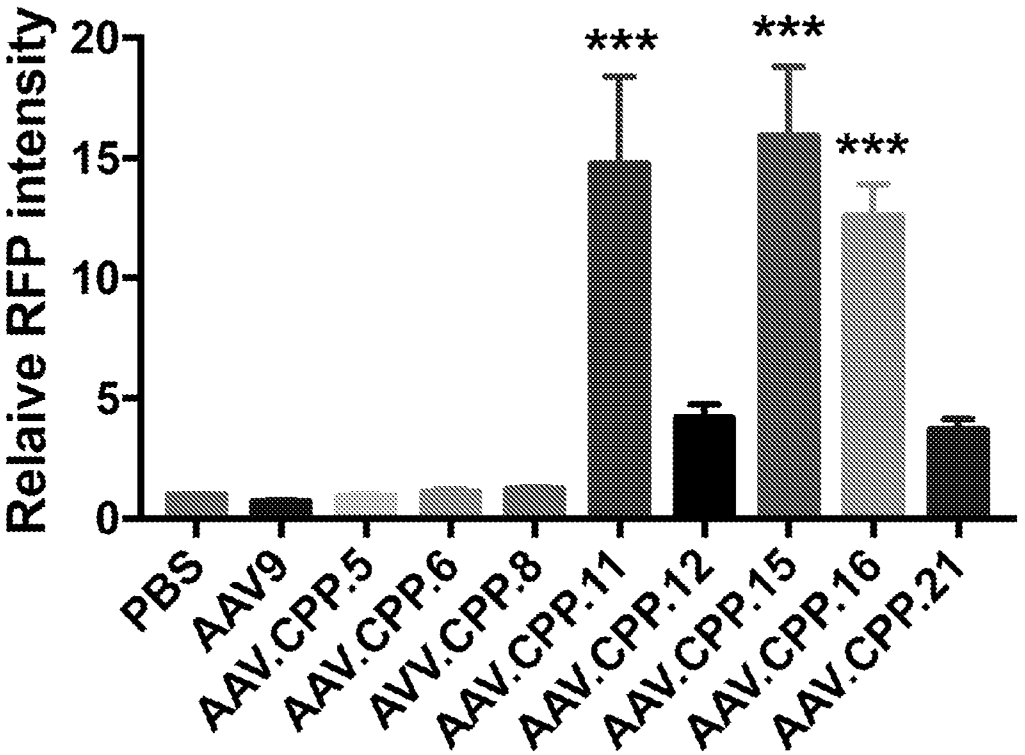

Some of the AAV variants were screened for the ability to cross the human BBB using an in vitro spheroid BBB model. The spheroid contains human microvascular endothelial cells, which form a barrier at the surface, and human pericytes and astrocytes. AAVs carrying nuclear RFP as reporter were assessed for their ability to penetrate from the surrounding medium into the inside of the spheroid and to transduce the cells inside. FIG. 4A shows an experimental schematic. FIGS. 4B-D show results for wt AAV9, AAV.CPP.16, and AAV.CPP.21, respectively, those and other peptides are quantified in FIG. 4E. In this model, peptides 11, 15, 16, and 21 produced the greatest permeation into the spheroids. See Materials and Methods #6 for more details.

Example 5. In Vivo BBB Permeation Screening

Figure 5A:
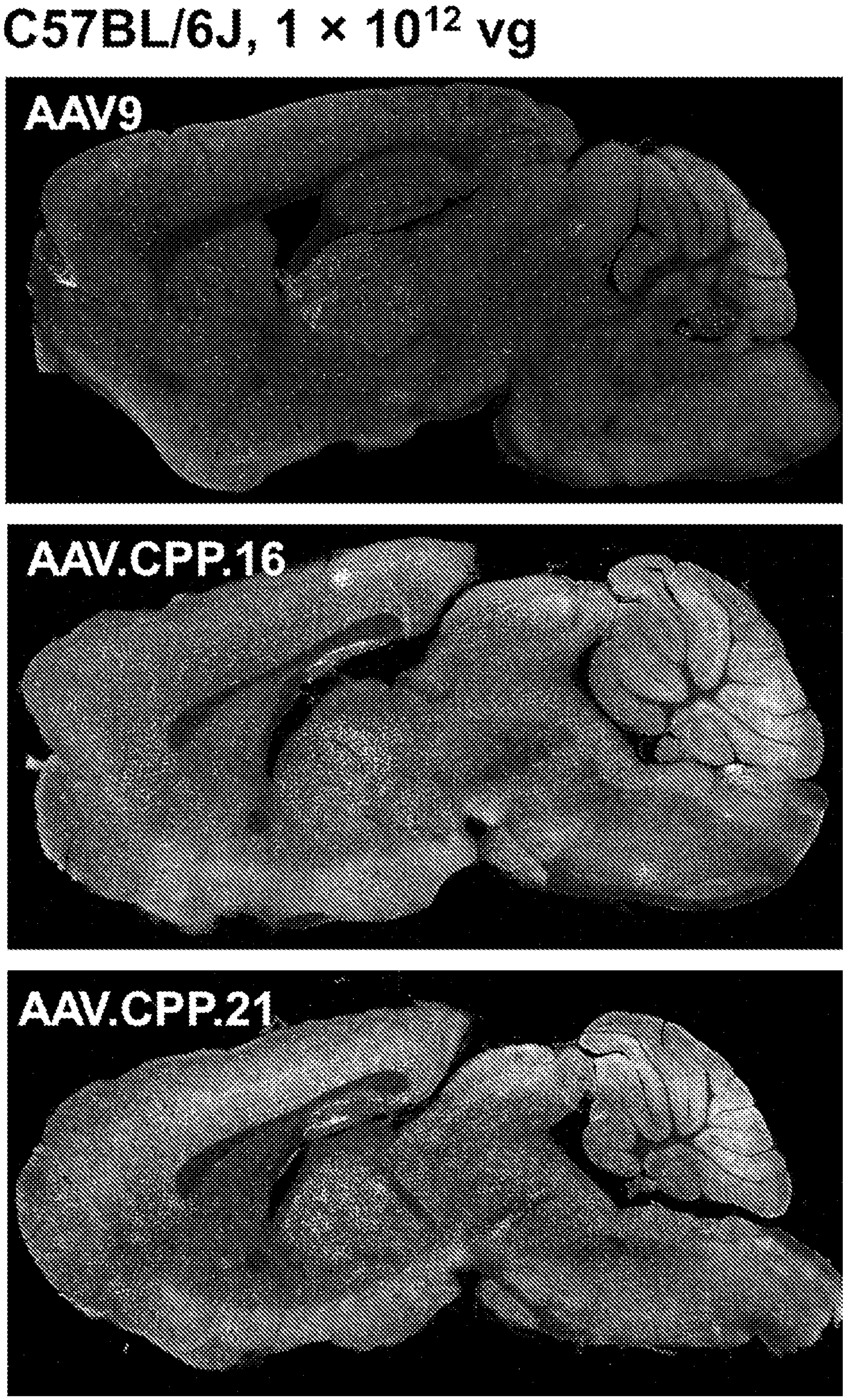
FIGS. 5A-5B depict representative images of brain sections (FIG. 5A) and their quantitative analysis (FIG. 5B) after intravenous administration of AAV9, AAV.CPP.16 and AAV.CPP.21 in C57BL/6J inbred mice. All candidate AAVs express nuclear red fluorescent protein (RFP) as reporter. The dose of AAV is $1\times10^{12}$ vg per animal. Each white dot in FIG. 5A represents a RFP-labeled cell.
Figure 5B:
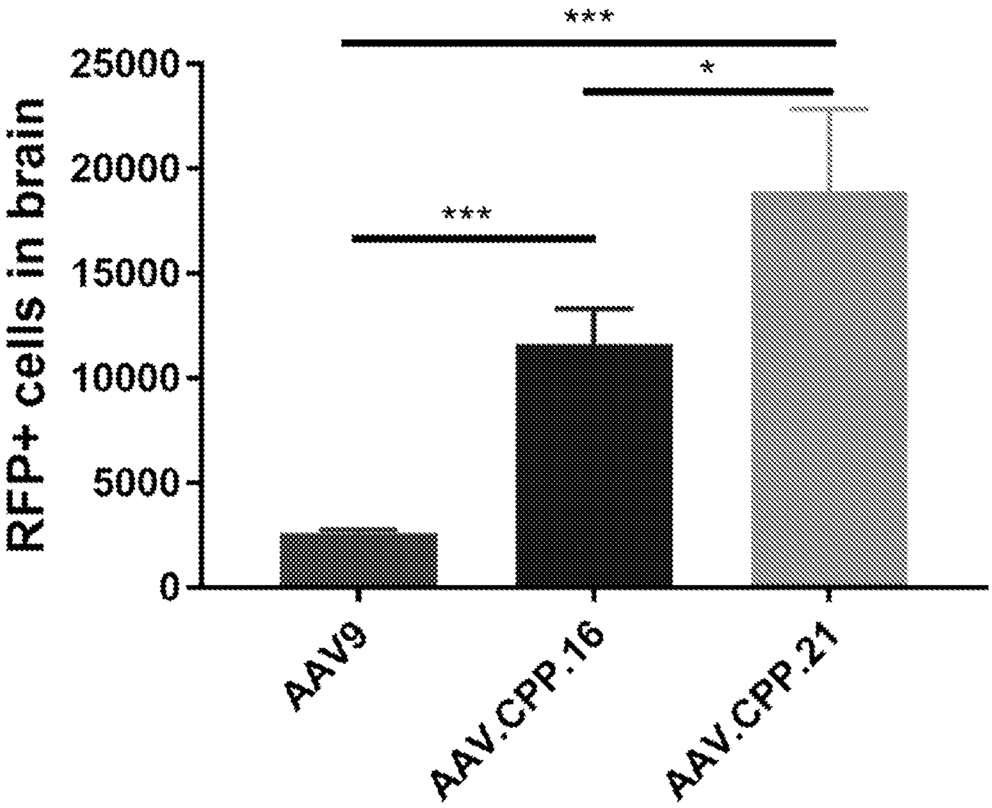
Figure 6A:
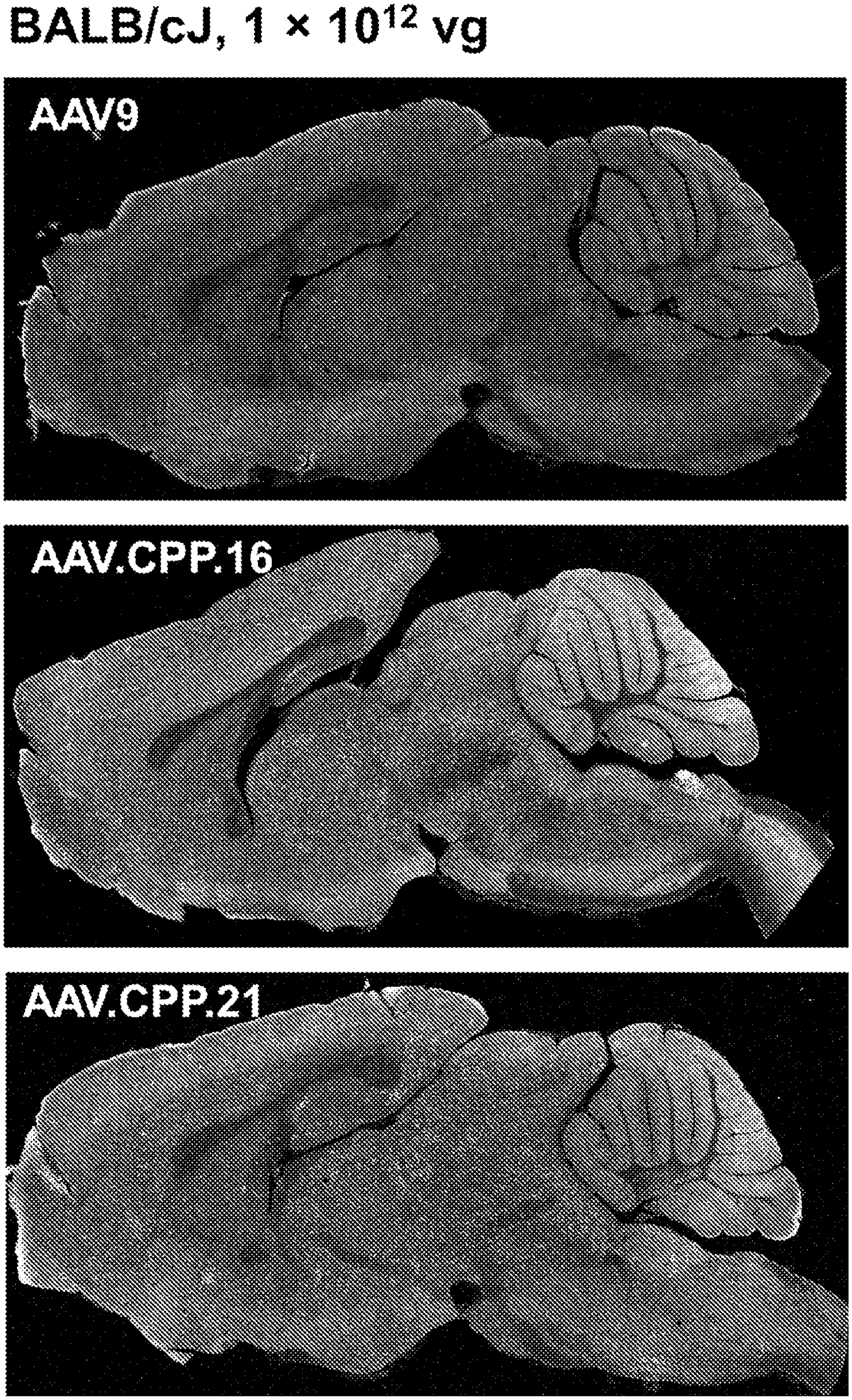
FIGS. 6A-6B depict representative images of brain sections (FIG. 6A) and their quantitative analysis (FIG. 6B) after intravenous administration of AAV9, AAV.CPP.16 and AAV.CPP.21 in BALB/cJ inbred mice. All candidate AAVs express nuclear red fluorescent protein (RFP) as reporter. The dose of AAV is $1\times10^{12}$ vg per animal. Each white dot in FIG. 6A represents a RFP-labeled cell.
Figure 6B:
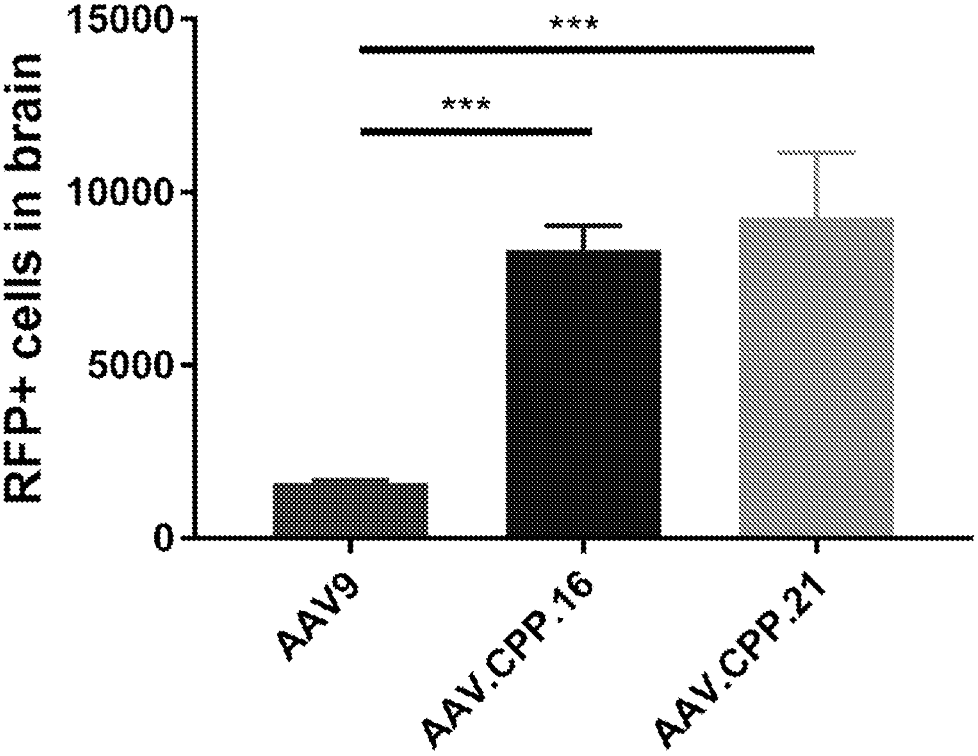

AAV.CPP.16 and AAV.CPP.21 were selected for further evaluation in an in vivo model, in experiments performed as described above for Example 2. All AAVs carried nuclear RFP as reporter. Both showed enhanced ability vs. AAV9 to transduce brain cells after intravenous administration in C57BL/6J adult mice (white dots in brain sections in FIG. 5A, quantified in FIG. 5B) and in BALB/c adult mice (white dots in brain sections in FIG. 6A, quantified in FIG. 6B).

Figure 7A:
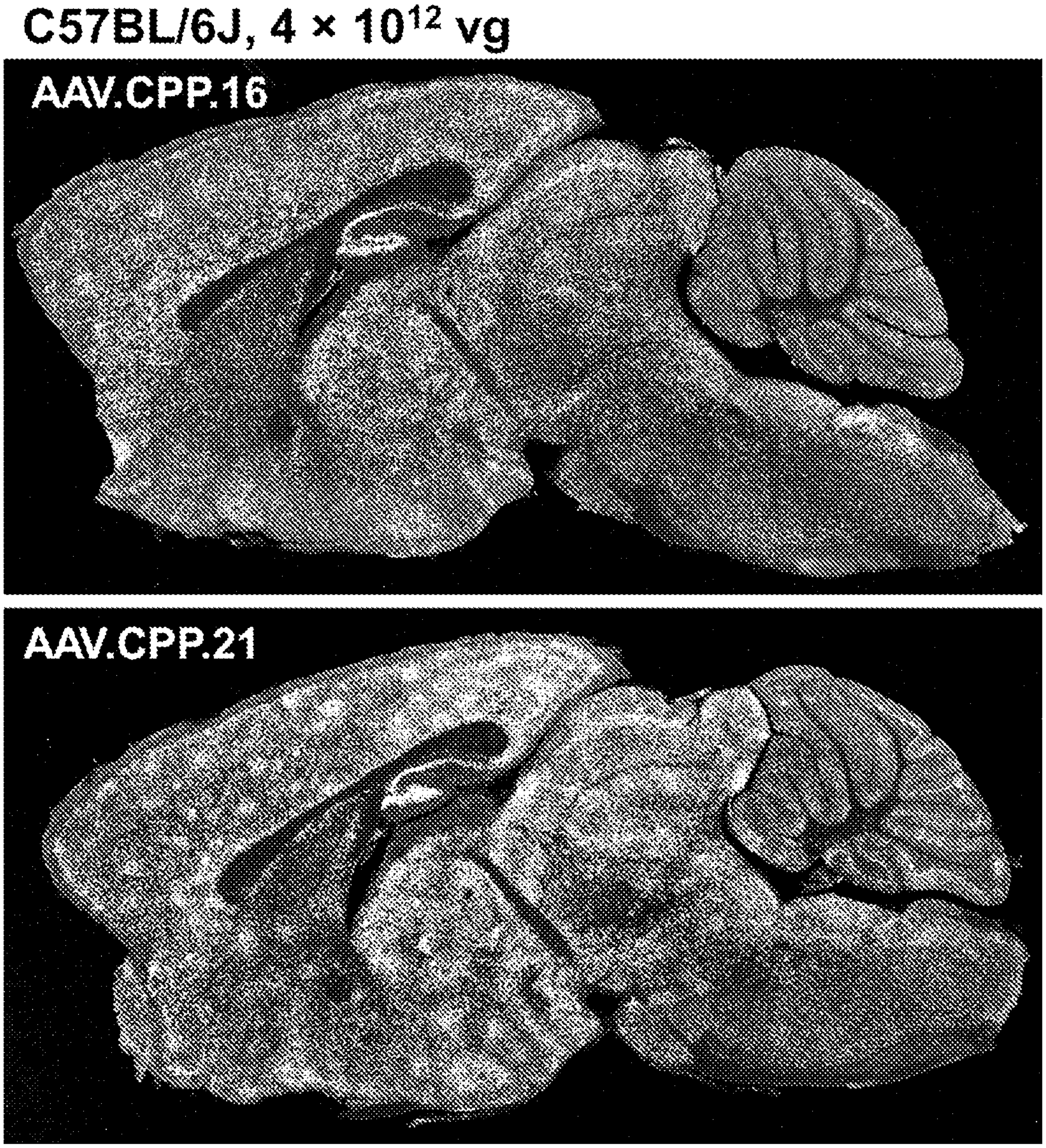
FIGS. 7A-7B depict representative images of brain sections (FIG. 7A) and their quantitative analysis (FIG. 7B) after intravenous administration of high-dose AAV.CPP.16 and AAV.CPP.21 in C57BL/6J inbred mice. Both candidate AAVs express nuclear red fluorescent protein (RFP) as reporter. The dose of AAV is $4\times10^{12}$ vg per animal. Each white dot in FIG. 7A represents a RFP-labeled cell.
Figure 7B:
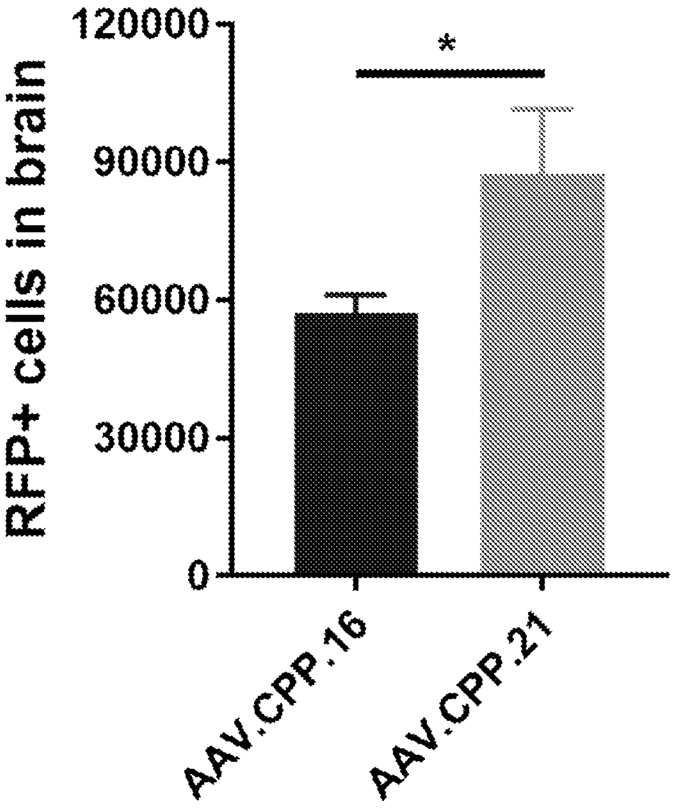

High doses of AAV.CPP.16 and AAV.CPP.21 ($4\times10^{12}$ vg per mouse, administered IV) resulted in widespread brain transduction in mice. Both AAVs carried nuclear RFP as reporter (white dots in brain sections in FIG. 7A, quantified in FIG. 7B).

Example 6. In Vivo Distribution of Modified AAVs

Figure 8A:
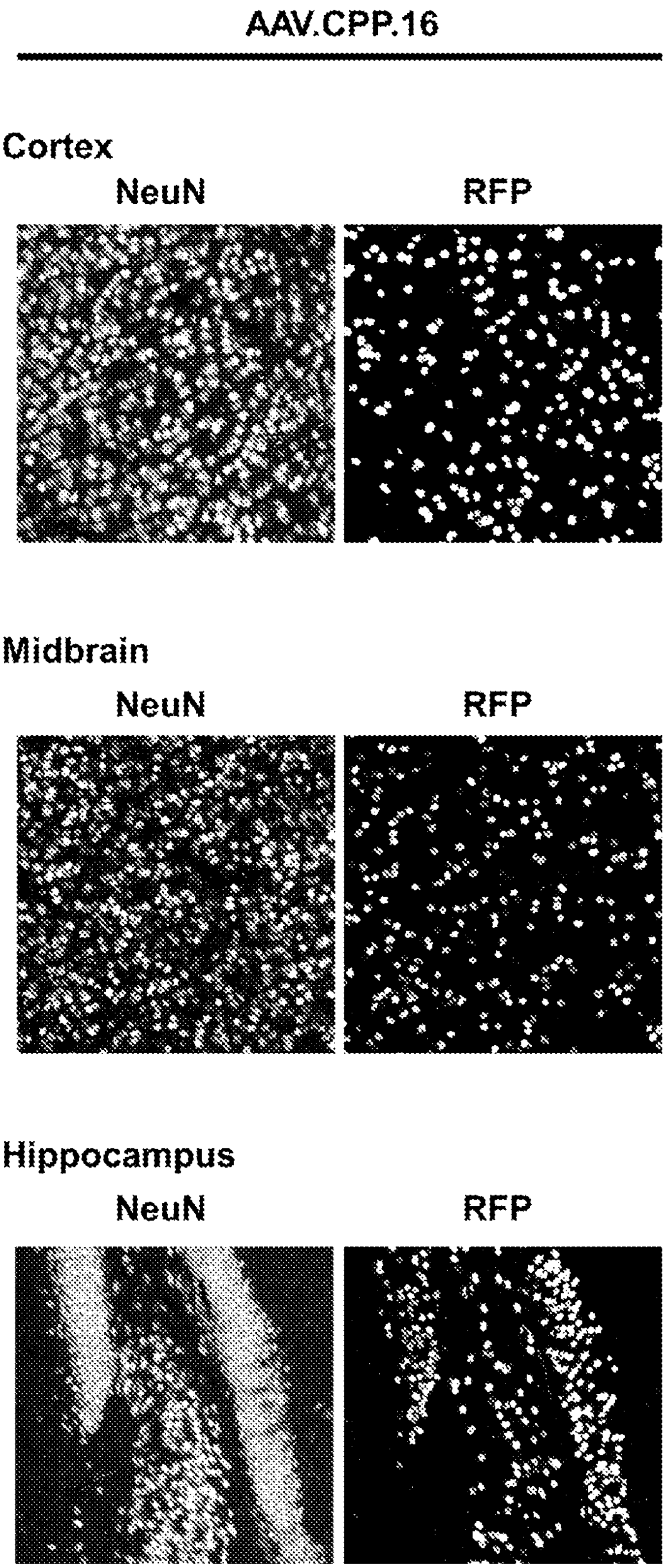
FIG. 8A shows AAV.CPP.16 and AAV.CPP.21 transduce adult neurons (labeled by a NeuN antibody) across multiple brain regions in mice including the cortex, midbrain and hippocampus. Transduced neurons are co-labeled by NeuN antibody and RFP. AAVs of $4\times10^{12}$ vg were administered intravenously in adult C57BL/6J mice (6 weeks old).

As shown in FIG. 8A, AAV.CPP.16 and AAV.CPP.21 preferentially targeted neurons (labeled by a NeuN antibody) across multiple brain regions in mice including the cortex, midbrain and hippocampus. Both AAVs carried nuclear RFP as a reporter.

Figure 8B:
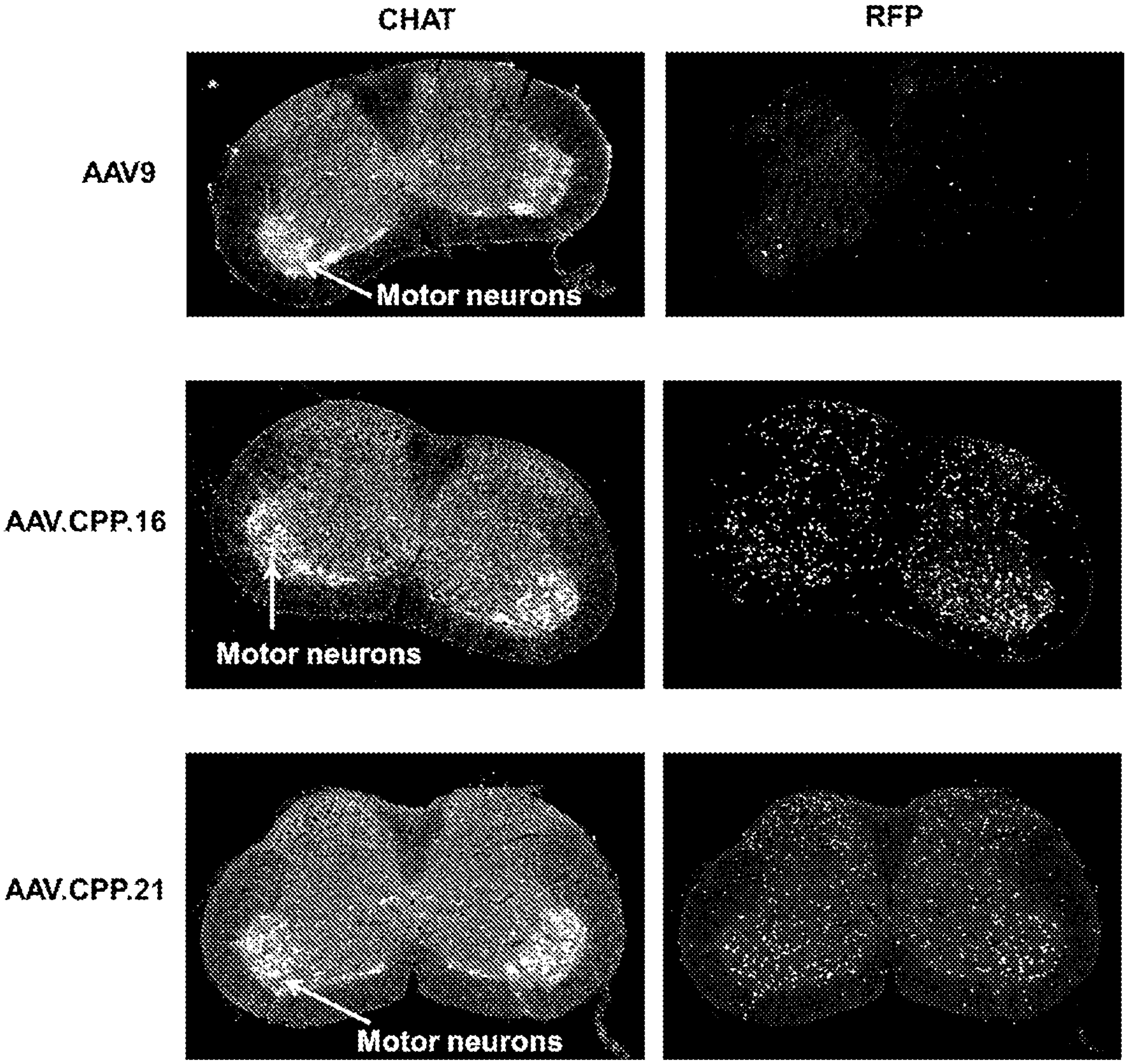
FIG. 8B depicts that AAV.CPP.16 and AAV.CPP.21 show enhanced ability vs. AAV9 in targeting the spinal cord and motor neurons in mice. AAVs of $4\times10^{10}$ vg were administered intravenously into neonate mice (1 day after birth). Motor neurons in the ventral horn of the spinal cord were visualized using CHAT antibody staining. Co-localization of RFP and CHAT signals suggests specific transduction of the motor neurons.

AAV.CPP.16 and AAV.CPP.21 also showed enhanced ability vs. AAV9 in targeting the spinal cord and motor neurons in mice. All AAVs carry nuclear RFP as reporter and were administered intravenously into neonate mice ($4\times10^{10}$ vg). Motor neurons were visualized using CHAT antibody staining. Co-localization of RFP and CHAT signals in FIG. 8B suggested specific transduction of the motor neurons.

Figure 9A:
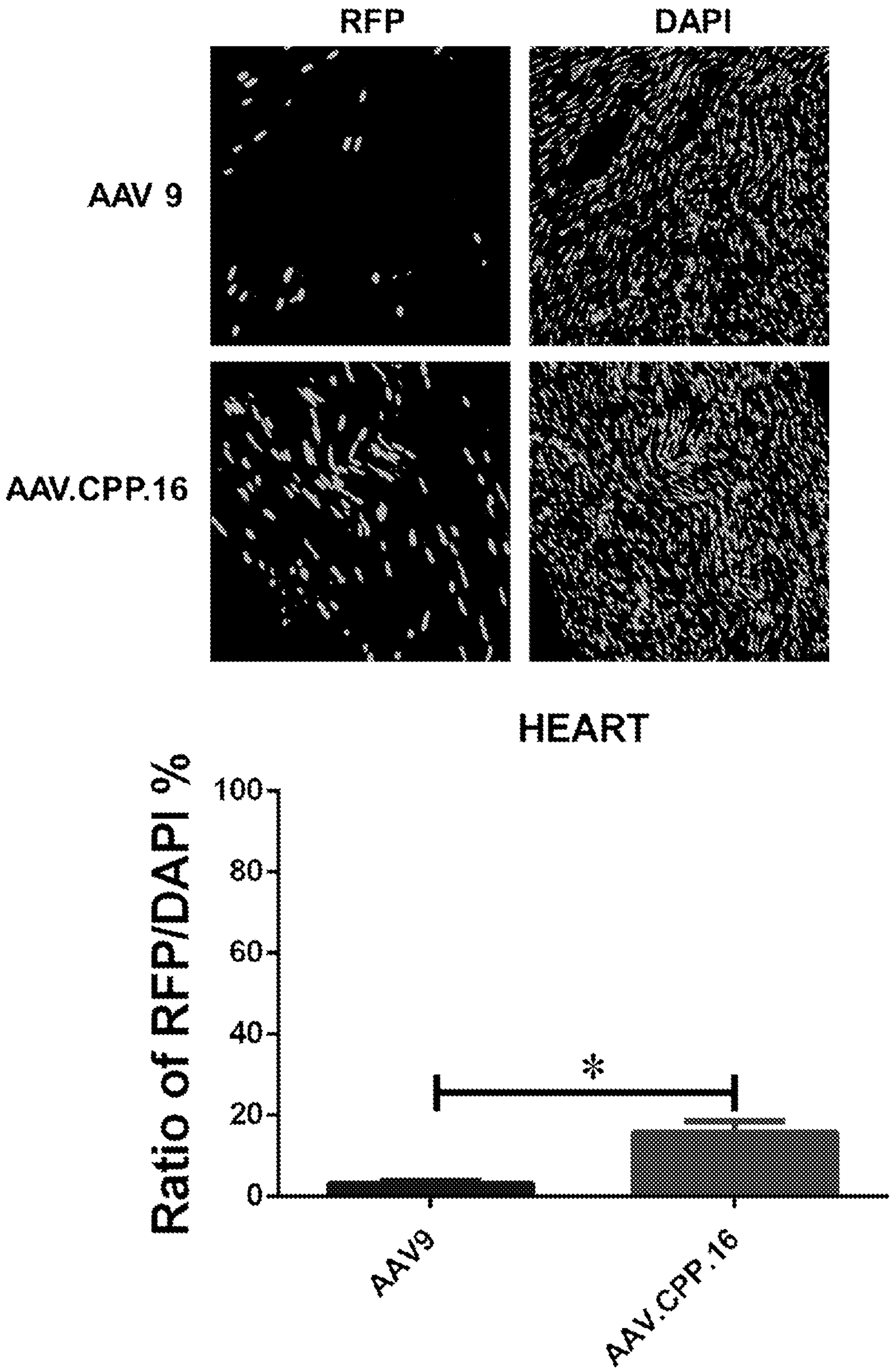
FIG. 9A depicts that AAV.CPP.16 shows enhanced ability vs. AAV9 in targeting the heart in adult mice. AAVs of $1\times10^{11}$ vg were administered intravenously in adult C57BL/6J mice (6 weeks old). Percentage of RFP-labeled cells relative to all DAPI-stained cells is presented. * $P<0.05$, Student test.
Figure 9B:
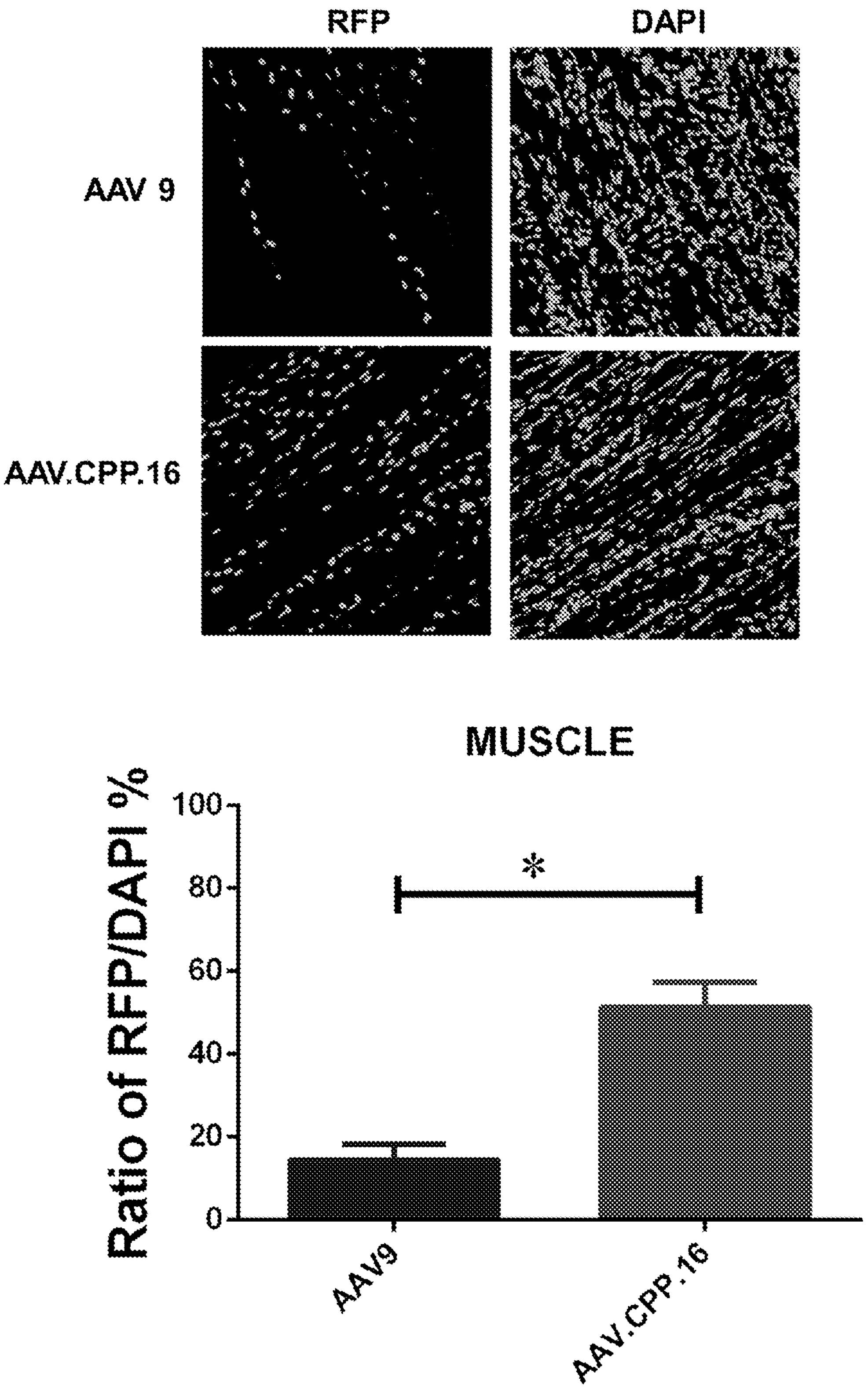
FIG. 9B depicts that AAV.CPP.16 shows enhanced ability vs. AAV9 in targeting the skeletal muscle in adult mice. AAVs of $1\times10^{11}$ vg were administered intravenously in adult C57BL/6J mice (6 weeks old). Percentage of RFP-labeled cells relative to all DAPI-stained cells is presented. * $P<0.05$, Student test.
Figure 9C:
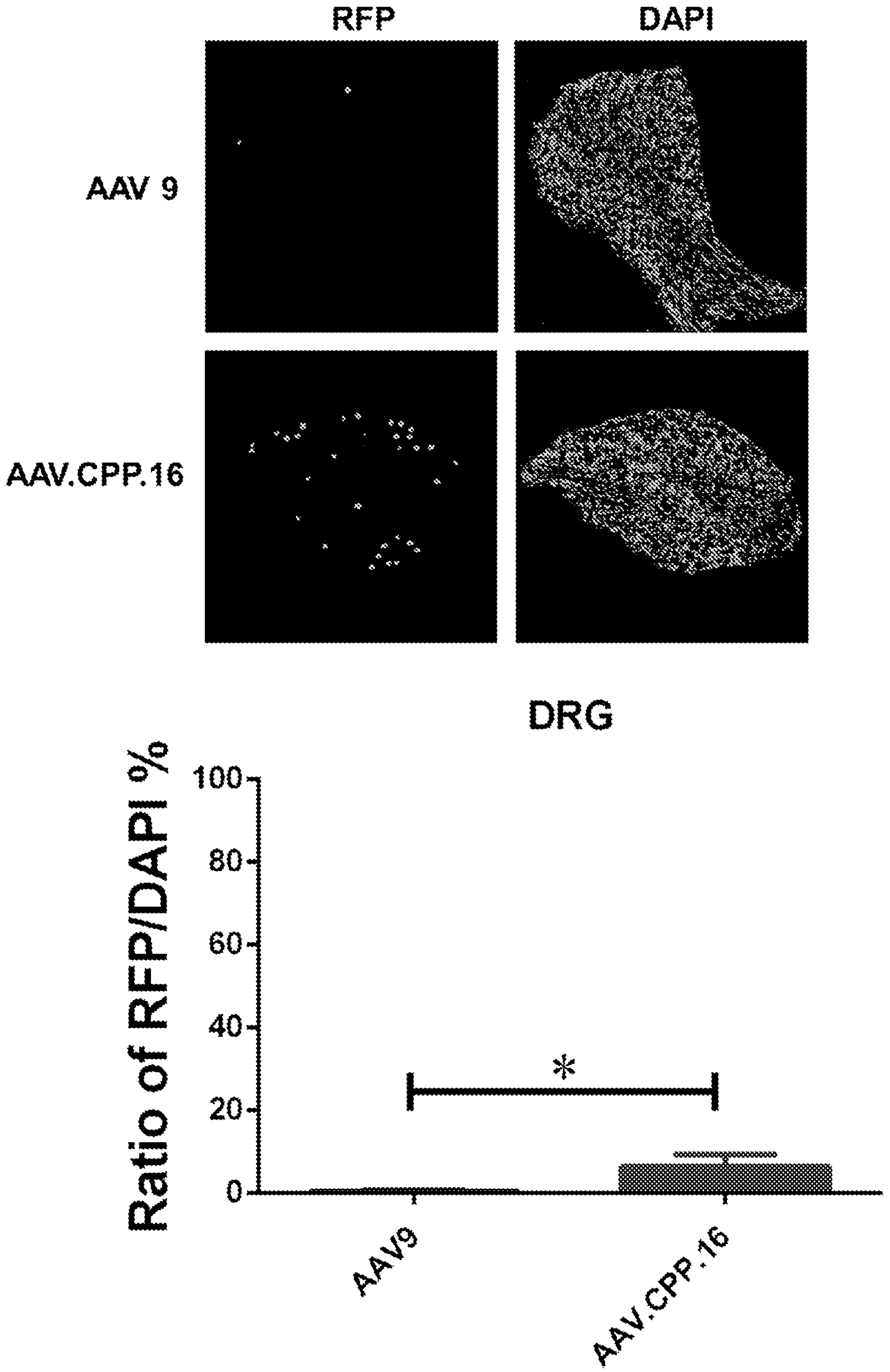
FIG. 9C depicts that AAV.CPP.16 shows enhanced ability vs. AAV9 in targeting the dorsal root ganglion (DRG) in adult mice. AAVs of $1\times10^{11}$ vg were administered intravenously in adult C57BL/6J mice (6 weeks old). Percentage of RFP-labeled cells relative to all DAPI-stained cells is presented. * P<0.05, Student test.

The relative abilities of AAV-CAG-H2B-RFP and AAV.CPP.16-CAG-H2B-RFP to transduce various tissues in mice was also evaluated. $1\times10^{11}$ vg was injected intravenously. The number of cells transduced was normalized to the number of total cells labeled by DAPI nuclear staining. The results showed that AAV.CPP.16 was more efficient than AAV9 in targeting heart (FIG. 9A); skeletal muscle (FIG. 9B), and dorsal root ganglion (FIG. 9C) tissue in mice.

Figure 10A:
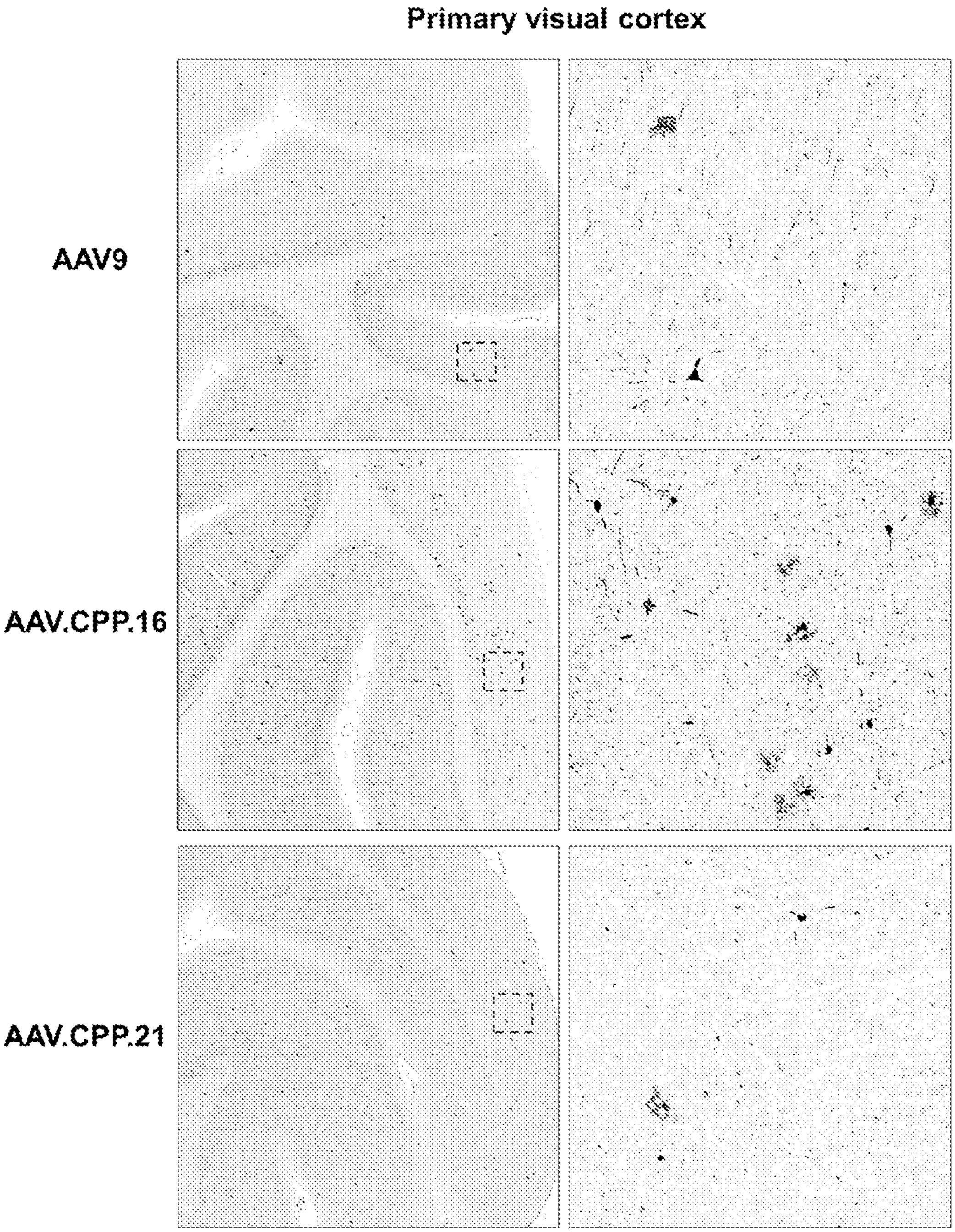
FIG. 10A depicts that AAV.CPP.16 and AAV.CPP.21 show enhanced ability vs. AAV9 to transduce brain cells in primary visual cortex after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.
Figure 10B:
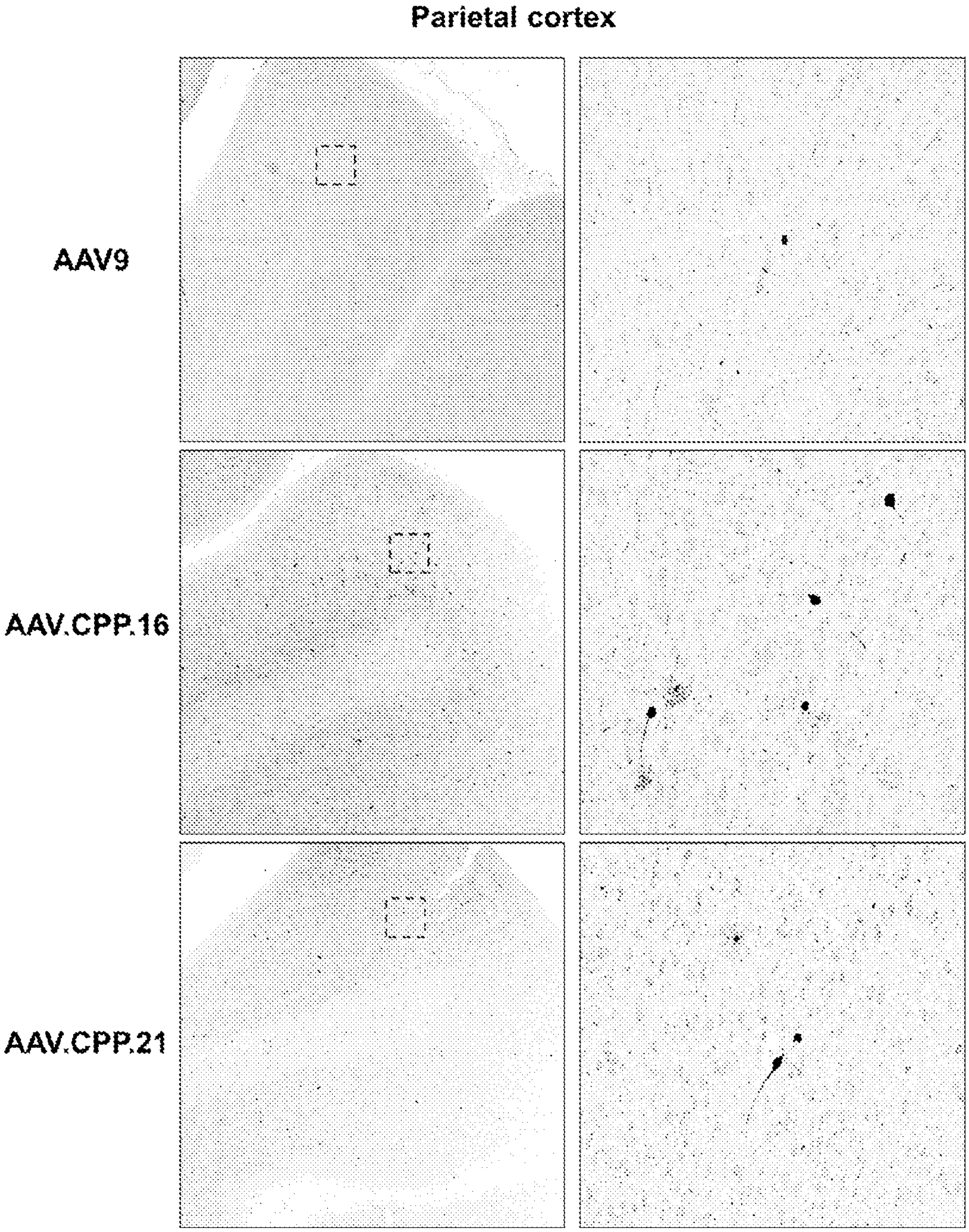
FIG. 10B depicts that AAV.CPP.16 and AAV.CPP.21 show enhanced ability vs. AAV9 to transduce brain cells in parietal cortex after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.
Figure 10C:
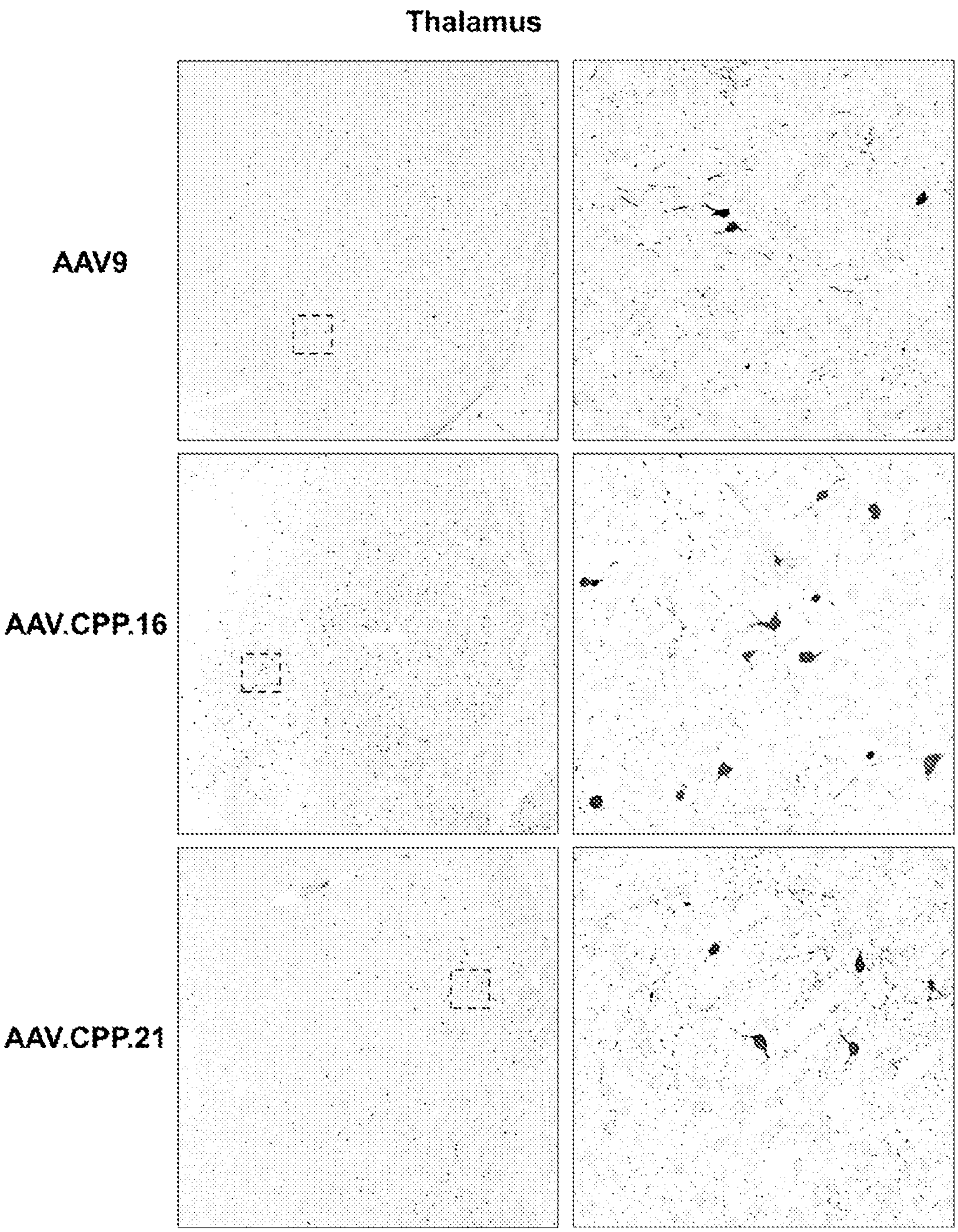
FIG. 10C depicts that AAV.CPP.16 and AAV.CPP.21 show enhanced ability vs. AAV9 to transduce brain cells in thalamus after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. AAV.CPP.16 transduced significantly more cells vs. AAV9. AAV.CPP.21 also transduced more cell vs. AAV9 although its effect was less evident in comparison with AAV.CPP.16.
Figure 10D:
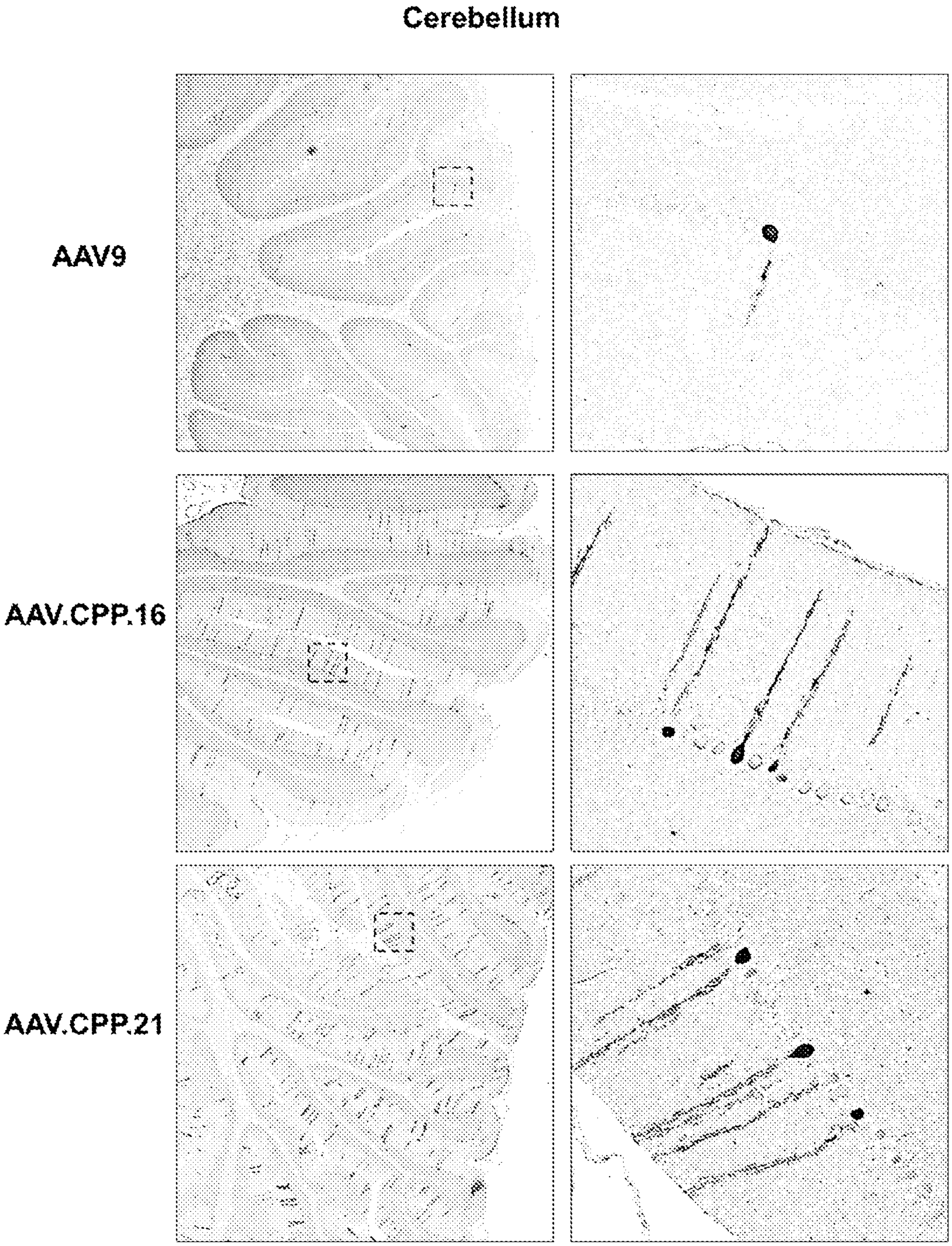
FIG. 10D depicts that AAV.CPP.16 and AAV.CPP.21 show enhanced ability vs. AAV9 to transduce brain cells in cerebellum after intravenous administration in non-human primates. $2\times10^{13}$ vg/kg AAVs-CAG-AADC (as reporter gene) were injected intravenously into 3 months old cynomolgus monkeys with low pre-existing neutralizing antibody. AAV-transduced cells (shown in black) were visualized using antibody staining against AADC. Squared areas in the left panels are enlarged as in the right panels. Both AAV.CPP.16 and AAV.CPP.21 transduced significantly more cells vs. AAV9.

Example 7. BBB Permeation in a Non-Human Primate Model $2\times10^{13}$ vg/kg AAVs-CAG-AADC (as reporter gene) were injected intravenously into 3-month-old cynomolgus monkeys. AAV-transduced cells (shown in black) were visualized using antibody staining against AADC. As shown in FIGS. 10A-D, AAV.CPP.16 and AAV.CPP.21 showed enhanced ability vs. AAV9 to transduce brain cells after intravenous administration in non-human primates. AAV.CPP.16 transduced significantly more cells then wt AAV9 in the primary visual cortex (FIG. 10A), parietal cortex (FIG. 10B), thalamus (FIG. 10C), and cerebellum (FIG. 10D). See Materials and Methods #7-8 for more details.

Example 8. AAV.CPP.16 and AAV.CPP.21 do not Bind to LY6A

Figure 11A:
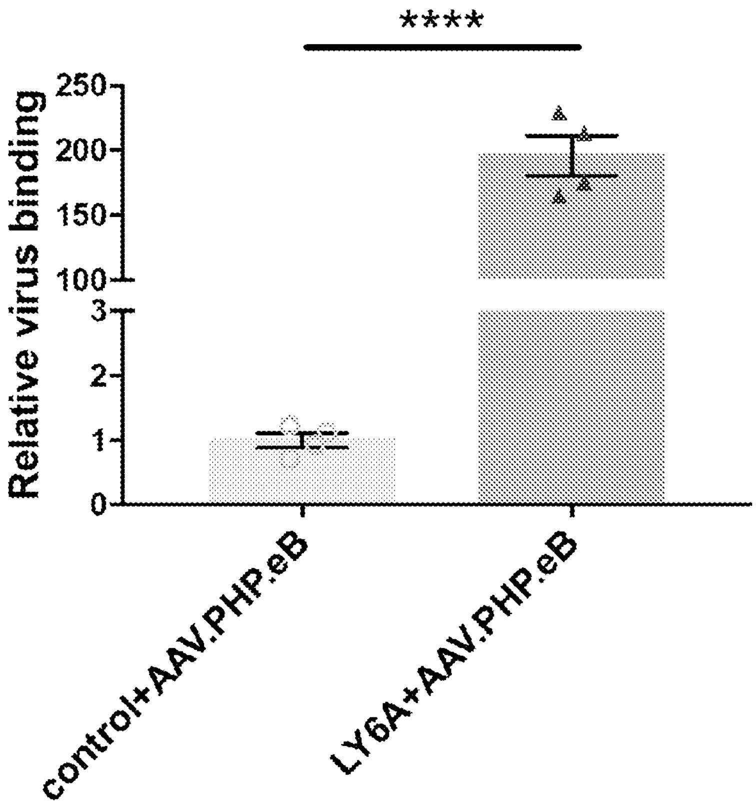
FIGS. 11A-11B depict that AAV.CPP.16 and AAV.CPP.21 do not bind to LY6A. LY6A serves as a receptor for AAVPHP.B and its variants including AAV.PHP.eB (as in U.S. Pat. No. 9,102,949, US20170166926) and mediates AAVPHP.eB's robust effect in crossing the BBB in certain mouse strains (Hordeaux et al. Mol Ther 2019 27(5):912-921; Huang et al. 2019, dx.doi.org/10.1101/538421). Over-expressing mouse LY6A in cultured 293 cells significantly increases binding of AAV.PHP.eB to the cell surface (FIG. 11A). On the contrary, over-expressing LY6A does not increase viral binding for AAV9, AAV.CPP.16 or AAV.CPP.21 (FIG. 11B). This suggests AAV.CPP.16 or AAV.CPP.21 does not share LY6A with AAV.PHP.eB as a receptor.
Figure 11B:
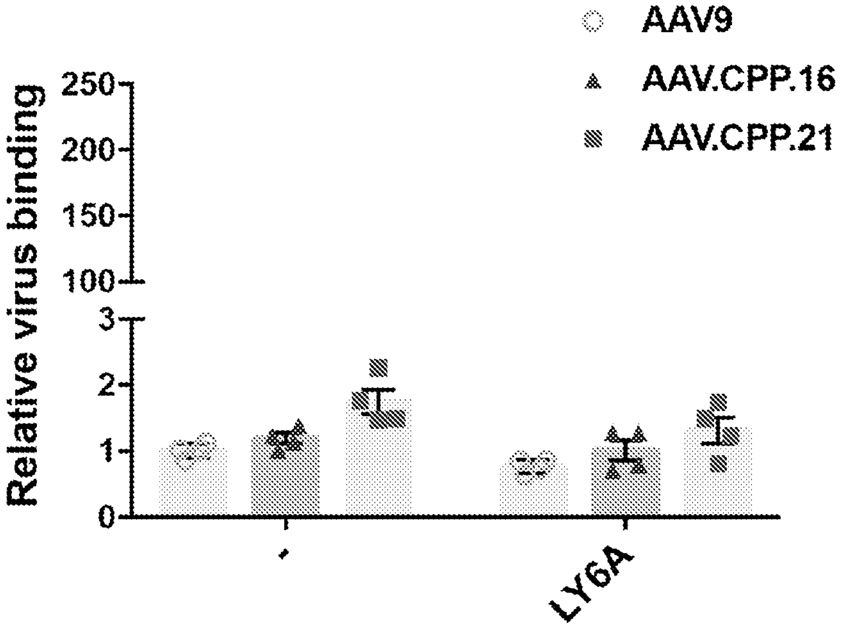

LY6A serves as a receptor for AAV.PHP.eB and mediates AAV.PHP.eB's robust effect in crossing the BBB in certain mouse strains. Over-expressing mouse LY6A in cultured 293 cells significantly increased binding of AAV.PHP.eB to the cell surface (see FIG. 11A). On the contrary, over-expressing LY6A does not increase viral binding for AAV9, AAV.CPP.16 or AAV.CPP.21 (see FIG. 11B). This suggests AAV.CPP.16 or AAV.CPP.21 does not share LY6A with AAV.PHP.eB as a receptor. See Materials and Methods #9 for more details.

Example 9. Delivering Therapeutic Proteins to the Brain Using AAV.CPP.21

Figure 12A:
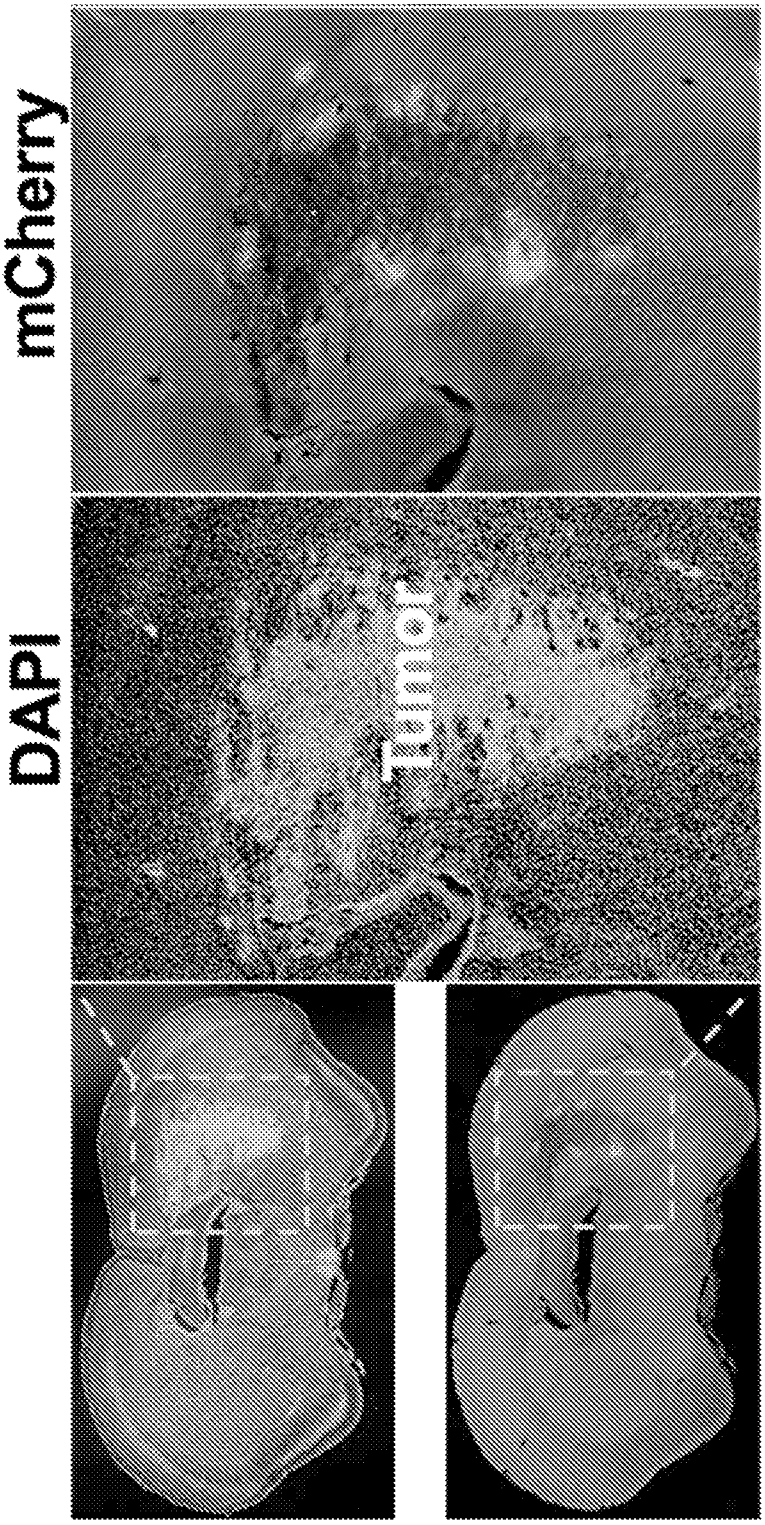
FIGS. 12A-12C depict that AAV.CPP.21 can be used to systemically deliver a therapeutic gene into brain tumor in a mouse mode of glioblastoma (GBM). As in FIG. 11A, intravenously administered AAV.CPP.21-H2BmCherry was shown to target tumor mass, especially the tumor expanding frontier (FIG. 12A).
Figure 12B:
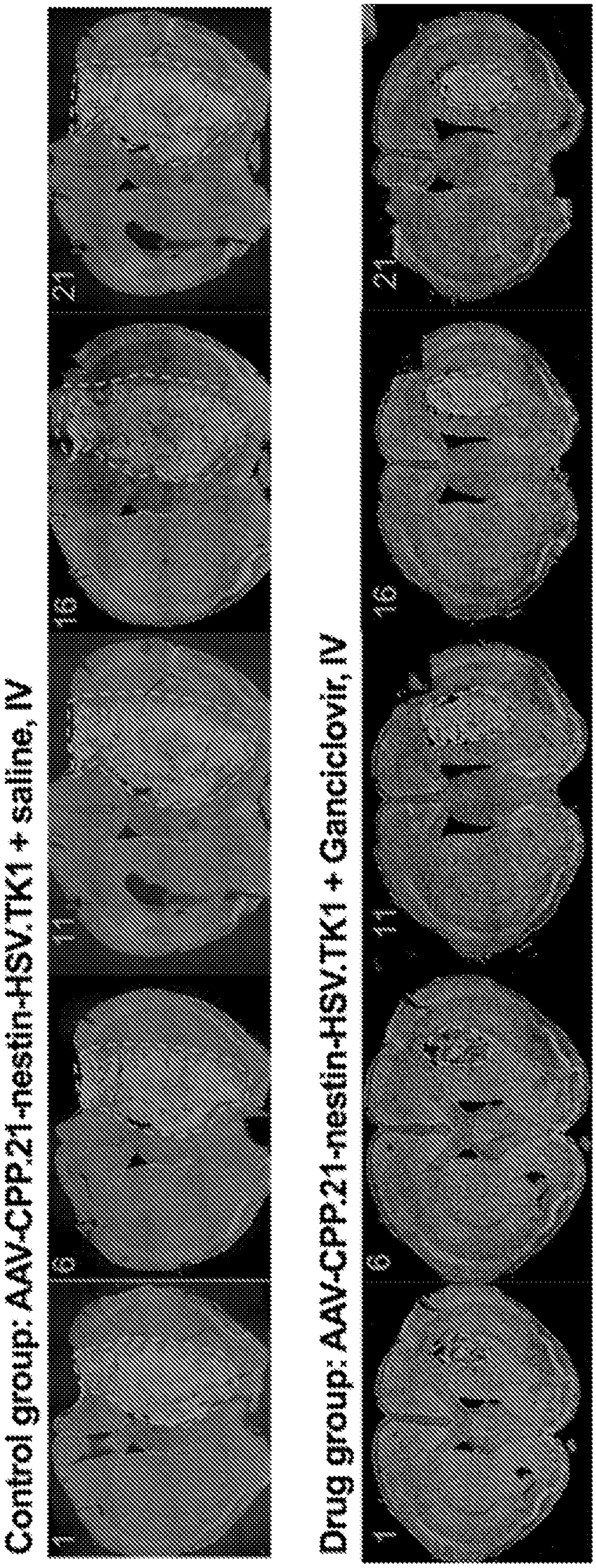
Figure 12C:
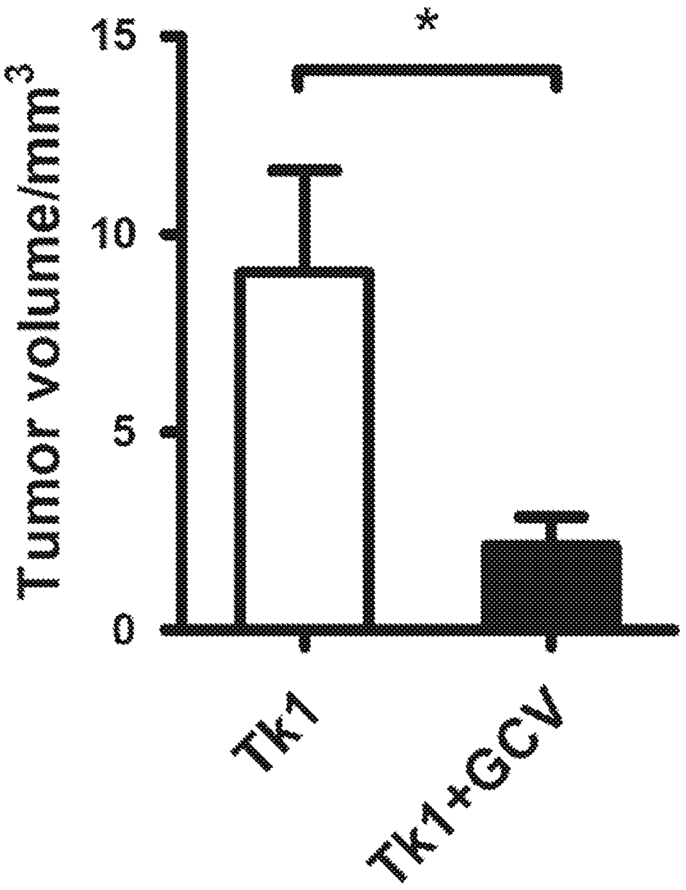

AAV.CPP.21 was used to systemically deliver the "suicide gene" HSV.TK1 in a mouse model of brain tumor (Materials and Methods #10). HSV.TK1 turns the otherwise "dormant" ganciclovir into a tumor-killing drug. Intravenously administered AAV.CPP.21-H2BmCherry (FIG. 12A, bottom left and middle right panel) was shown to target tumor mass, especially the tumor expanding frontier. As shown in FIGS. 12B-C, using AAV.CPP.21 to systemically deliver the "suicide gene" HSV.TK1 resulted in shrinkage of brain tumor mass, when combined with the pro-drug ganciclovir. These results show that AAV.CPP.21 can be used to systemically deliver a therapeutic gene into brain tumor. See Materials and Methods #10 for more details.

Example 10. Intracerebral Administration of AAV.CPP.21

Figure 13:
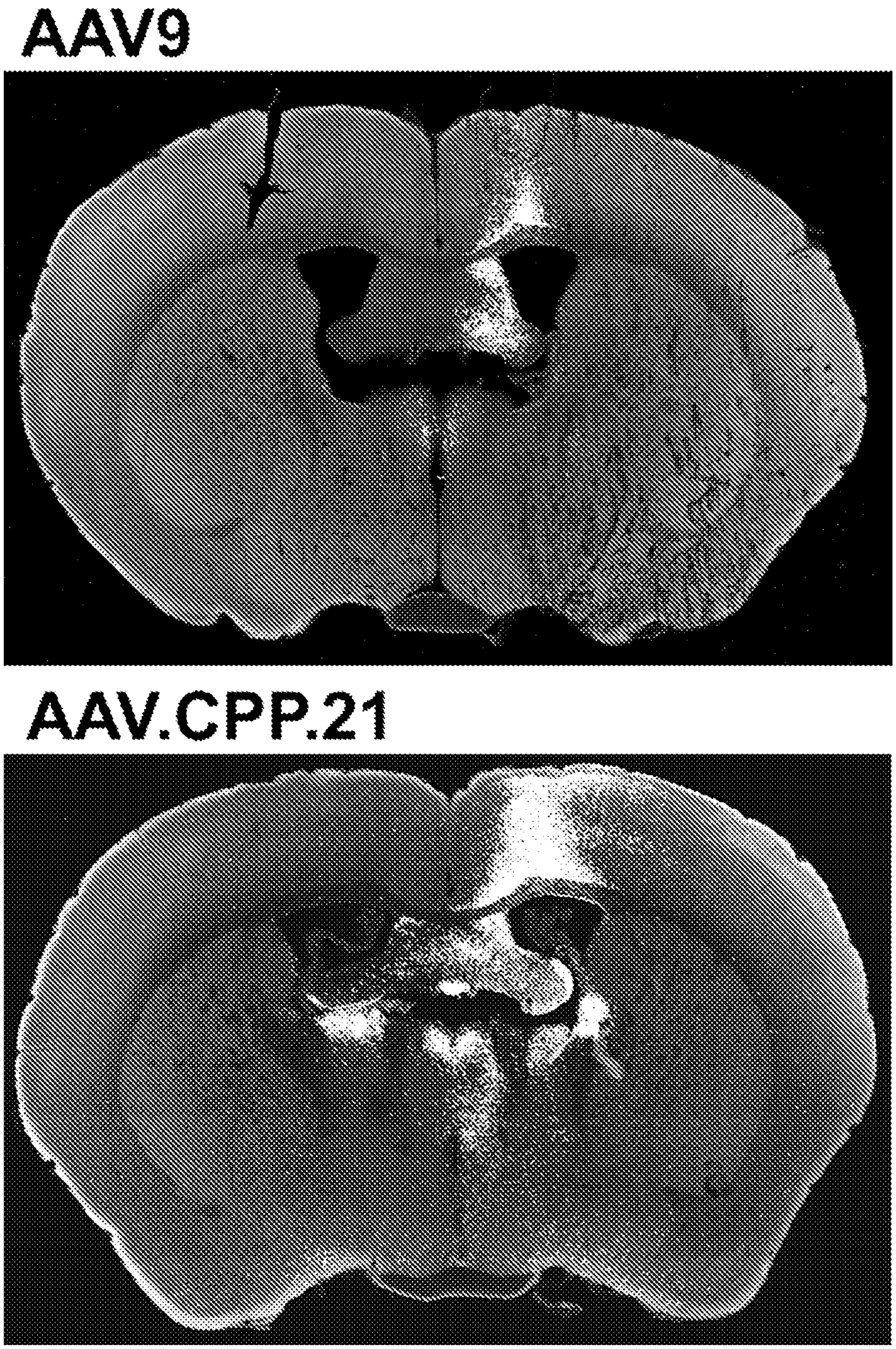
FIG. 13 depicts that when injected locally into adult mouse brain, AAV.CPP.21 resulted in more widespread and robust transduction of brain tissue in comparison with AAV9. Intracerebral injection of AAVs ($1\times10^{11}$ vg) was performed in adult mice (>6 weeks old) and brain tissues were harvested and examined 3 weeks after AAV injection. ** P<0.01, Student test.

In addition to systemic administration (such as in Example 2), an AAV as described herein was administered locally into the mouse brain. Intracerebral injection of AAV9-H2B-RFP and AAV.CPP.21-H2B-RFP (FIG. 13) resulted in more widespread and higher-intensity RFP signal in AAV.CPP.21-treated brain sections vs. AAV9-treated ones. See Materials and Methods #4 for more details.

Figure 14:
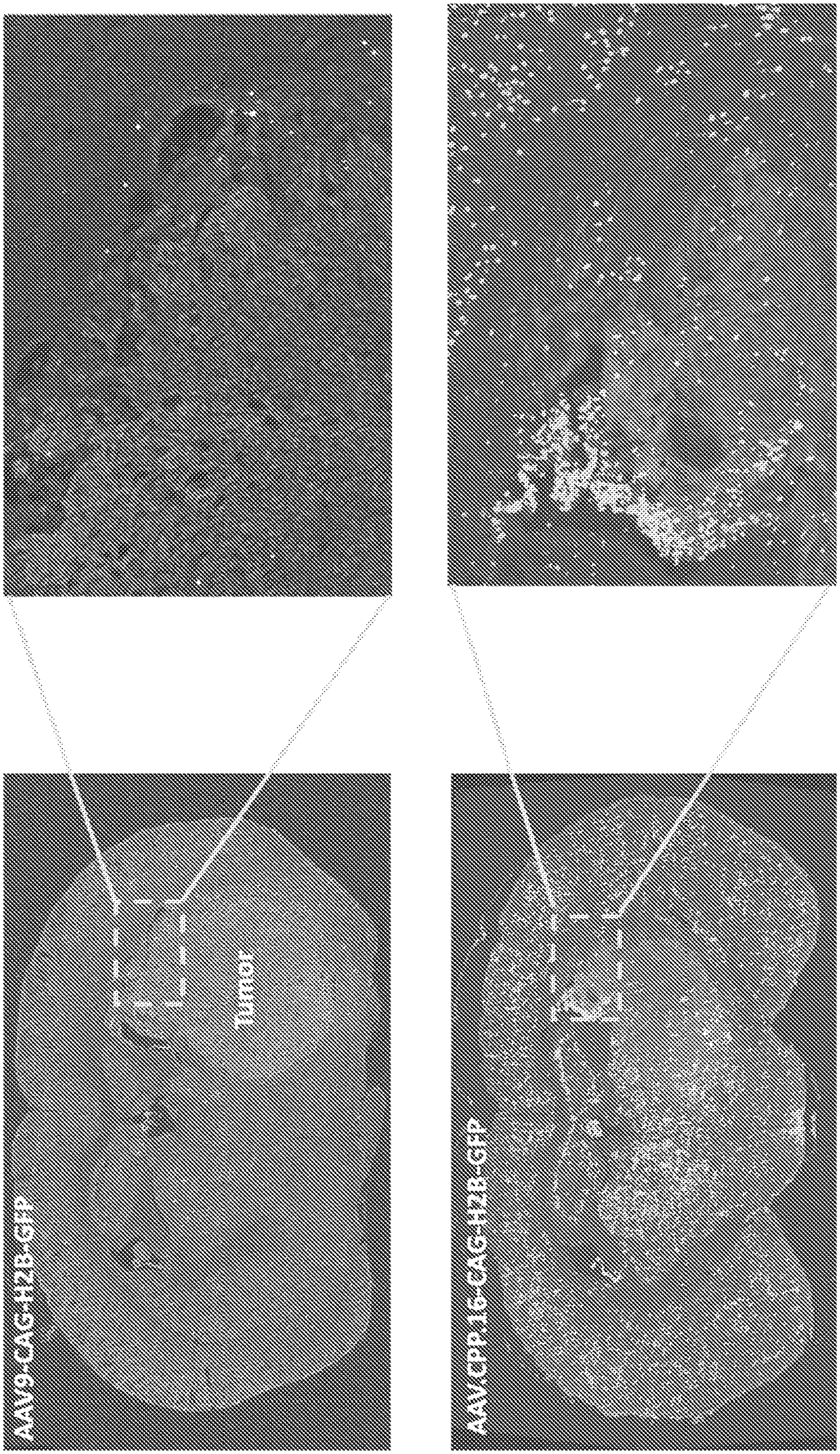
FIG. 14 is a set of images comparing delivery efficiency to the GBM tumor microenvironment in a mouse model using AAV9 (top) and AAV.CPP16 (bottom). As can be seen in the insets (right), AAV.CPP16 provided greater delivery efficacy.

Example 11. Systemic Delivery of AAV.CPP.16 to the Glioblastoma Tumor Microenvironment Using systemic administration (such as in Example 2), delivery of an AAV as described herein into the brains of an orthotopic, immunocompetent mouse glioblastoma model (GL261 model). (as described in Materials and Methods #10). As shown in FIG. 14, AAV.CPP16 far outperformed AAV9, with significant delivery both to tumors and to the surrounding microenvironment.

Figure 1C:
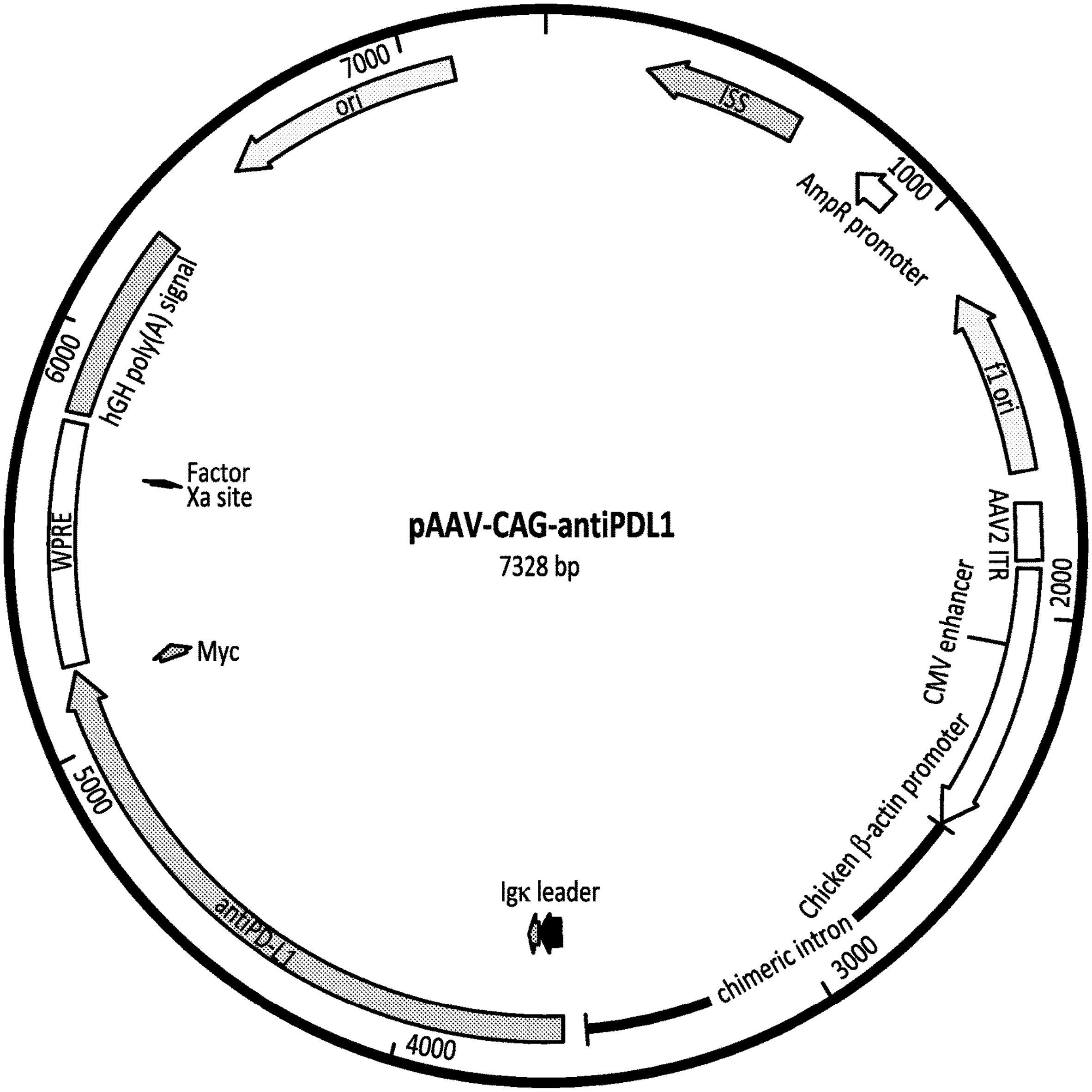
Figure 15A:
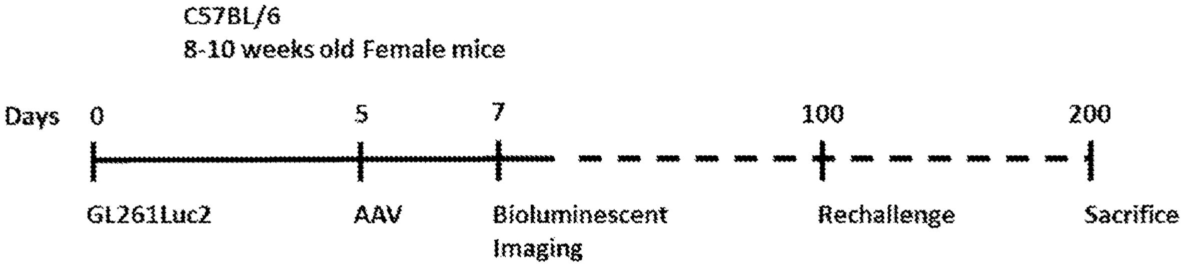
FIGS. 15A-C show that AAV.CPP.16-antiPD-L1 mediated immunotherapy prolonged survival in a murine GBM model.
Figure 15B:
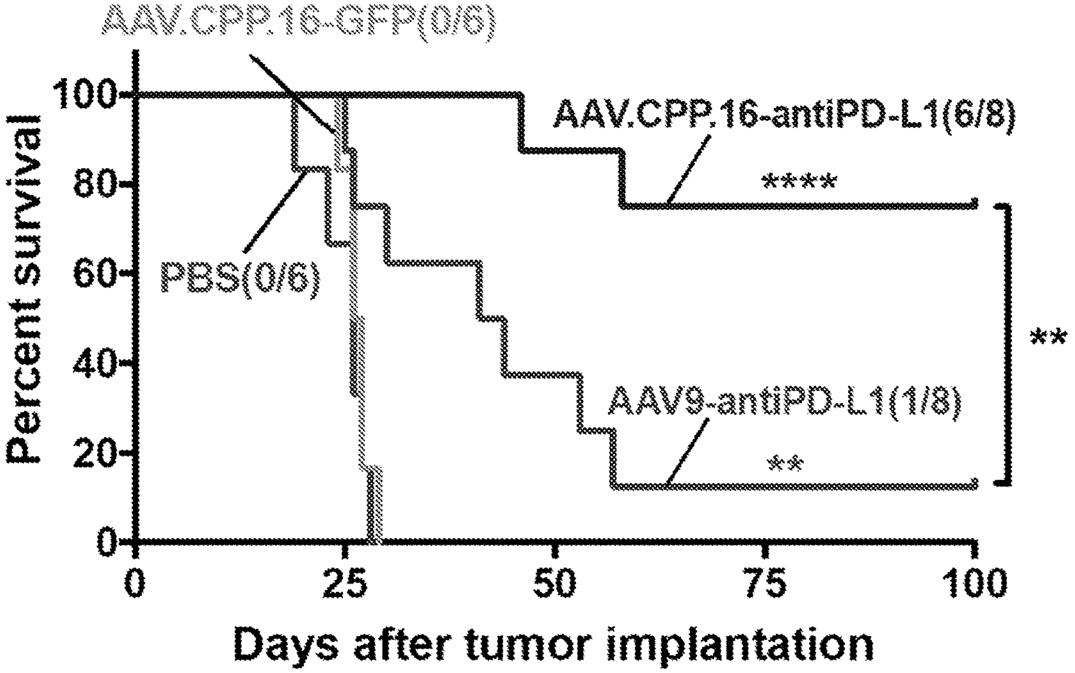
Figure 15C:
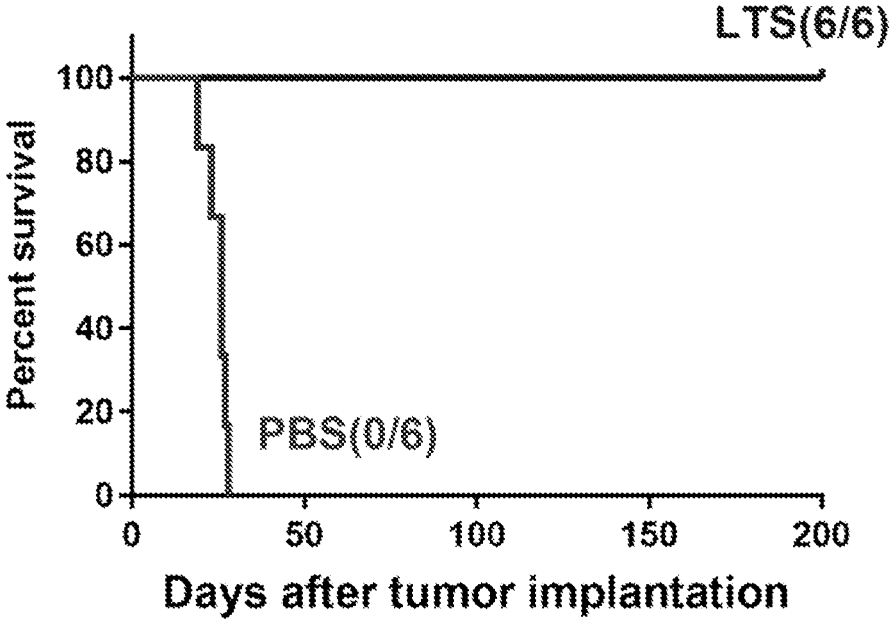

To determine whether this increased efficiency of delivery would translate to improved therapeutic efficacy, various treatments were administered to the mouse GBM model; FIG. 15A provides a schematic of the experimental protocol. The results, shown in FIGS. 15B-C, demonstrated that AAV.CPP.16-antiPD-L1 mediated immunotherapy significantly prolonged survival in the murine GBM model. As shown in FIG. 15B, 1 of 8 mice treated with AAV9-antiPD-L1 survived long term, while 6/8 mice treated with the AAV.CPP.16-antiPD-L1 survived long term (longer than 100 days). FIG. 15C shows that all 6 of the long-term survivors (five treated with AAV.CPP.16-antiPD-L1 plus one treated with AAV9-antiPD-L1; one of the long-term survivors treated with AAV.CPP.16-antiPD-L1 died during re-challenging surgery due to technical reasons) were still alive 200 days after tumor implantation. Thus, intravenous injection of AAV.CPP.16 expressing an antibody targeting the mouse PD-L1 eradicated GBM tumors in 75% of the mice, whereas untreated mice died within a month of tumor implantation.

Figure 16A:
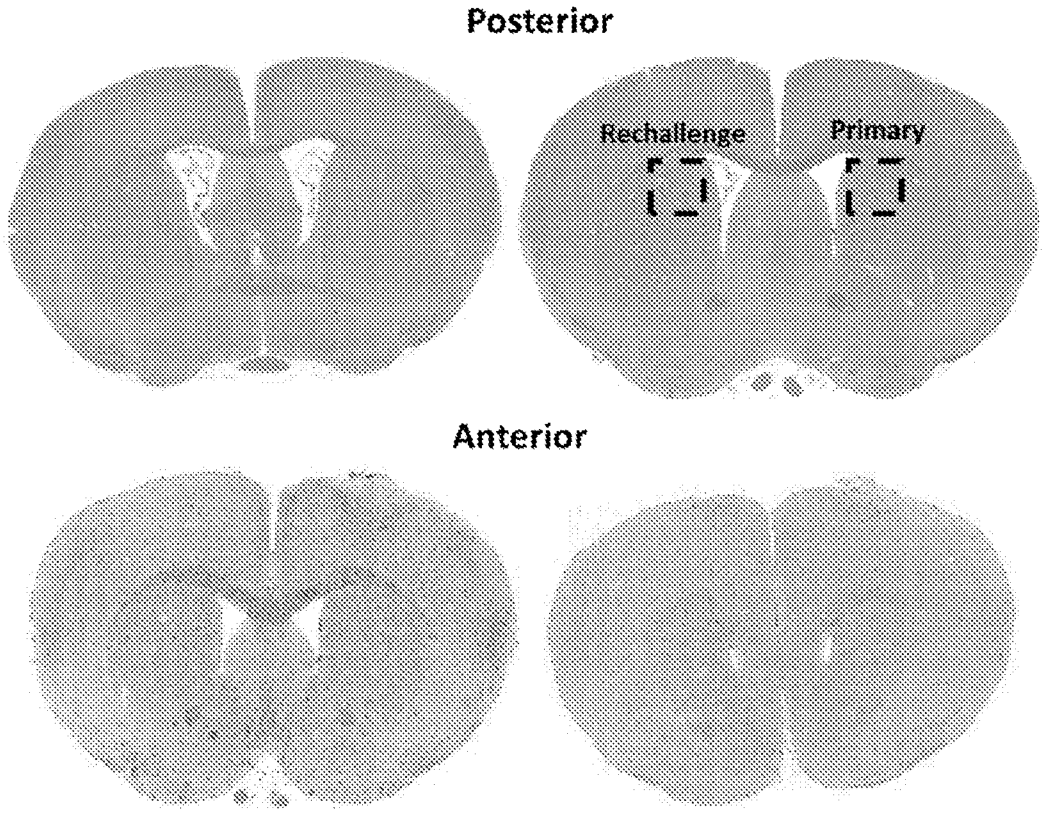
FIGS. 16A-C show that GBM tumors were eradicated in all of the long-term surviving mice.
Figure 16B:
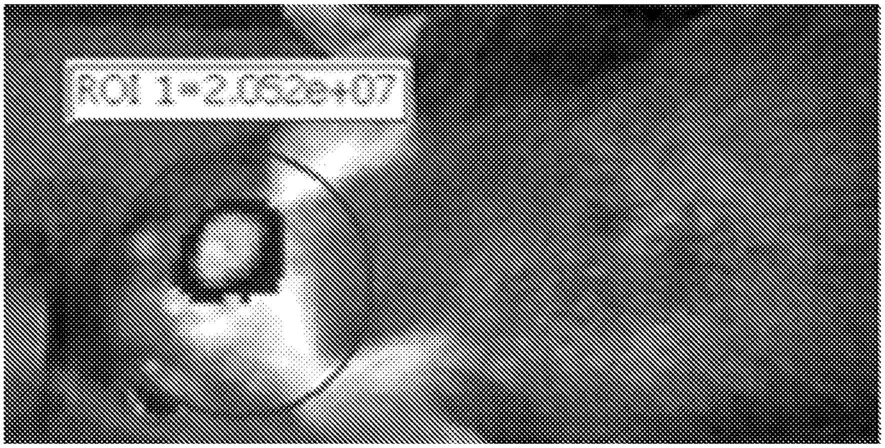
Figure 16C:
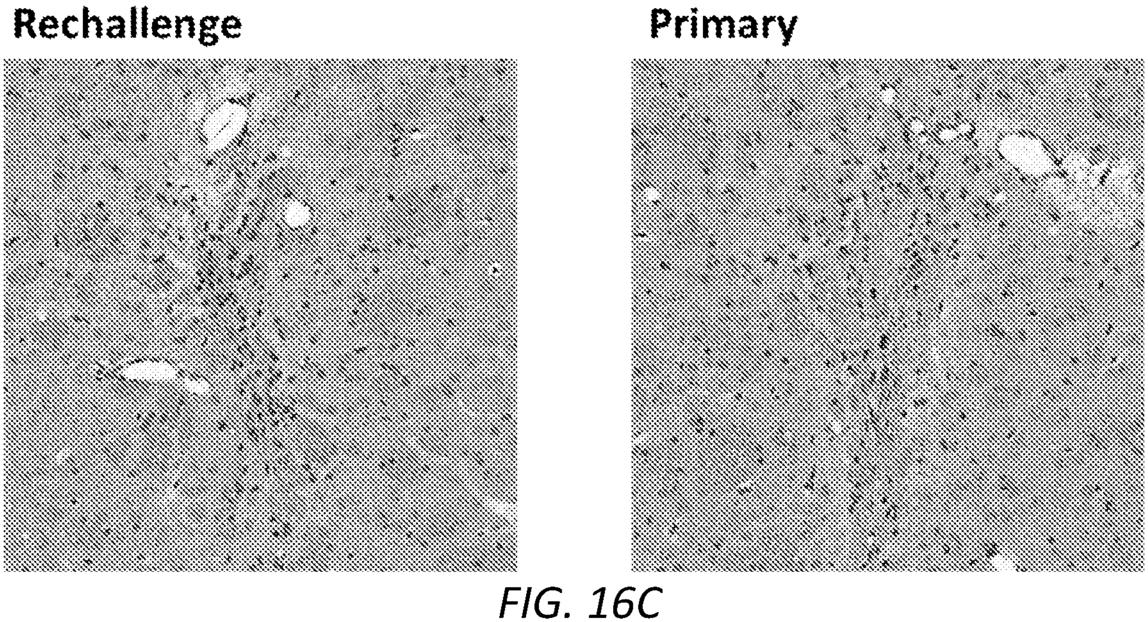

The long-term surviving mice were sacrificed at 200 days, and their brains examined. As shown in FIG. 16A, no evidence of tumors remained. FIG. 16B shows a bioluminescent image taken of one of the mice that had extended survival, showing that at 7 days post implant the tumor cells were present. FIG. 16C shows that the initial tumor implantation is devoid of residual tumor and only gliotic scar tissue remains, indicating complete tumor eradication.

Furthermore, immunohistochemistry showed that CB8+ cytotoxic T cells were also present in the GBM tumor site, further evidence for an immune reaction.

Example 12. Expression of HA-Tagged antiPD-L1 Antibody in GBM Tumor

Figure 17A:
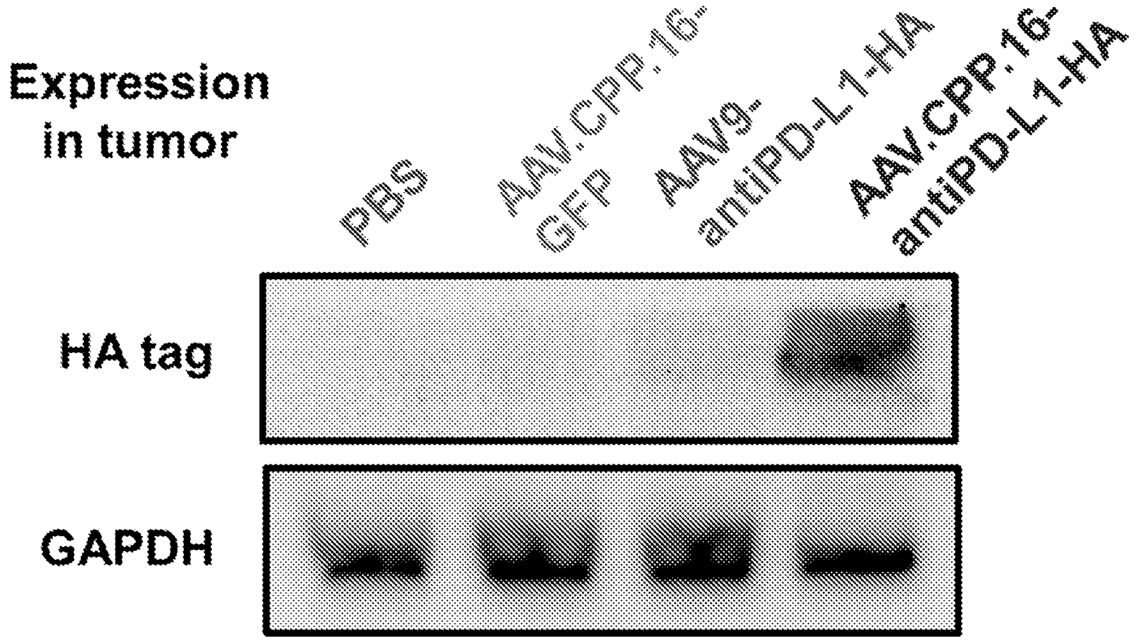
FIGS. 17A-17B show expression of HA-tagged antiPD-L1 antibody in GBM tumor as measured by Western blotting. AAVs of 1e12 vg or PBS were injected intravenously 5 days after tumor implantation in mice. Tumor tissues were harvested 14 days after IV injection. The intensities of HA tag staining (FIG. 17A) were quantified as measurement of antiPD-L1 antibody expression (FIG. 17B).
Figure 17B:
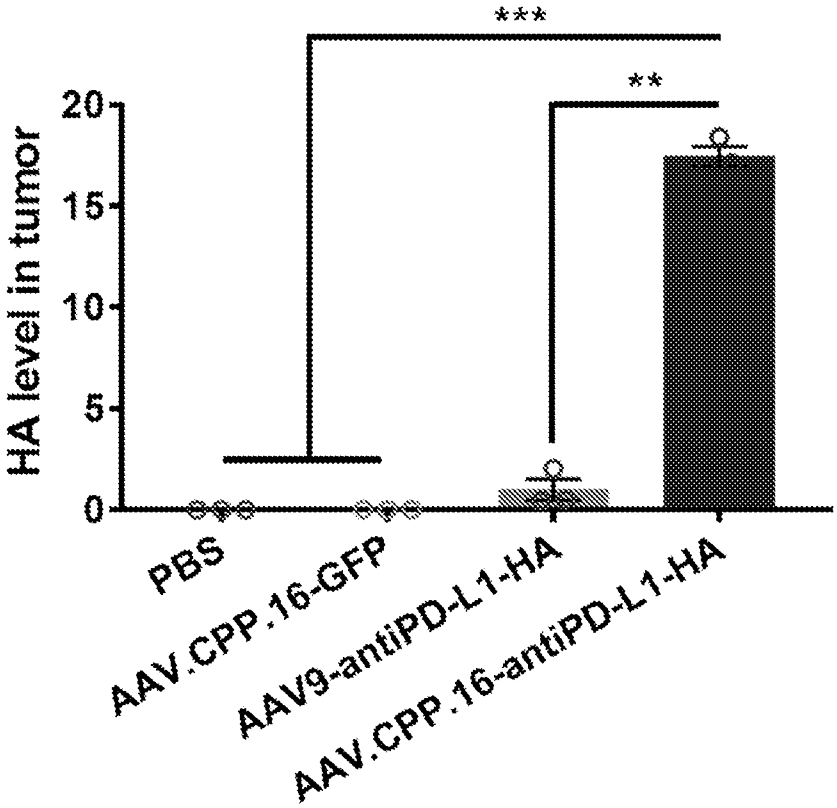

Expression of HA-tagged antiPD-L1 antibody in GBM tumor as measured by Western blotting is shown in FIGS. 17A-17B. AAVs of 1e12 vg or PBS were injected intravenously 5 days after tumor implantation in mice. Tumor tissues were harvested 14 days after IV injection. The intensities of HA tag staining (FIG. 17A) were quantified as measurement of antiPD-L1 antibody expression (FIG. 17B).

REFERENCES

1. Stupp, R. et al. Radiotherapy plus concomitant and adjuvant temozolomide for glioblastoma. The New England journal of medicine 352, 987-996 (2005).
2 Ostrom, Q. T. et al. CBTRUS Statistical Report: Primary brain and other central nervous system tumors diagnosed in the United States in 2010-2014. Neuro-oncology 19, v1-v88 (2017).
3 Brennan, C. W. et al. The somatic genomic landscape of glioblastoma. Cell 155, 462-477 (2013).
4 Lim, M., Xia, Y., Bettegowda, C. & Weller, M. Current state of immunotherapy for glioblastoma. Nature reviews. Clinical oncology 15, 422-442 (2018).
5 Perry, A. & Wesseling, P. Histologic classification of gliomas. Handbook of clinical neurology 134, 71-95 (2016).
6 Wen, P. Y. & Kesari, S. Malignant gliomas in adults. The New England journal of medicine 359, 492-507 (2008).
7 Jain, R. K. et al. Angiogenesis in brain tumours. Nature reviews. Neuroscience 8, 610-622 (2007).
8 Deverman, B. E., Ravina, B. M., Bankiewicz, K. S., Paul, S. M. & Sah, D. W. Y. Gene therapy for neurological disorders: progress and prospects. Nature reviews. Drug discovery (2018).
9 Hudry, E. & Vandenberghe, L. H. Therapeutic AAV Gene Transfer to the Nervous System: A Clinical Reality. Neuron 101, 839-862 (2019).
10 Batista, A. R. et al. Ly6a differential expression in BBB is responsible for strain specific CNS transduction profile of AAV-PHP.B. Human gene therapy (2019).
11 Hordeaux, J. et al. The GPI-Linked Protein LY6A Drives AAV-PHP.B Transport across the Blood-Brain Barrier. Molecular therapy: the journal of the American Society of Gene Therapy 27, 912-921 (2019).
12 Huang, Q. et al. Delivering genes across the blood-brain barrier: LY6A, a novel cellular receptor for AAV-PHP.B capsids. PloS one 14, e0225206 (2019).
13 Hordeaux, J. et al. The Neurotropic Properties of AAV-PHP.B Are Limited to C57BL/6J Mice. Molecular therapy: the journal of the American Society of Gene Therapy 26, 664-668 (2018).
14 Matsuzaki, Y. et al. Intravenous administration of the adeno-associated virus-PHP.B capsid fails to upregulate transduction efficiency in the marmoset brain. Neuroscience letters 665, 182-188 (2018).
15 Nakashima, H. et al. Modeling tumor immunity of mouse glioblastoma by exhausted CD8(+) T cells. Scientific reports 8, 208 (2018).
16 Reul et al., Tumor-Specific Delivery of Immune Checkpoint Inhibitors by Engineered AAV Vectors. Front Oncol. 2019 Feb. 14; 9:52.
17 Engeland et al., CTLA-4 and PD-L1 Checkpoint Blockade Enhances Oncolytic Measles Virus Therapy. Molecular Therapy 22(11):1949-1959 November 2014.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of delivering an antibody or antigen binding fragment thereof that binds PD-L1 to treat a glioblastoma in a subject, the method comprising systemically administering to the subject an adeno-associated virus (AAV) vector comprising (i) an AAV capsid, wherein the AAV capsid comprises a peptide insert of TVSALFK (SEQ ID NO: 8) or TVSALK (SEQ ID NO: 4), and (ii) a transgene encoding an antibody or antigen binding fragment thereof that binds PD-L1.

2. The method of claim 1, wherein the AAV vector is AAV9.

3. The method of claim 2, wherein the AAV9 comprises AAV9 VP1.

4. The method of claim 3, wherein the peptide insert is located in a position corresponding to amino acids 588 and 589 of AAV9 VP1 comprising SEQ ID NO:85.

5. The method of claim 1, wherein the AAV vector is delivered to a cell in the brain of the subject.

6. The method of claim 1, further comprising administering chemotherapy, radiation, and/or surgical resection to the subject.

7. The method of claim 6, wherein the chemotherapy comprises temozolamide, lomustine, or a combination thereof.

8. The method of claim 6, wherein the method comprises administering radiation to the subject.

9. The method of claim 6, wherein the method comprises administering surgical resection to the subject.

10. The method of claim 6, wherein the method comprises administering chemotherapy to the subject.

11. The method of claim 10, wherein the chemotherapy comprises temozolamide.

12. The method of claim 10, wherein the chemotherapy comprises lomustine.

13. The method of claim 10, wherein the chemotherapy comprises a combination of temozolamide and lomustine.

14. The method of claim 1, wherein the peptide insert is TVSALFK (SEQ ID NO: 8).

15. The method of claim 1, wherein the peptide insert is TVSALK (SEQ ID NO: 4).

16. The method of claim 1, wherein the administration is intravenous.

17. The method of claim 1, wherein the administration is intraarterial.

18. The method of claim 1, wherein the administration is intraperitoneal.

* * * * *

SEQUENCE LISTING

```
<160> NUMBER OF SEQ ID NOS: 117

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Pro Ala Leu Arg
1               5


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

-continued

```
Val Ser Ala Leu Lys
1               5


<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Val Pro Ala Leu Arg
1               5


<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Val Ser Ala Leu Lys
1               5


<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Thr Val Ser Ala Leu Lys
1               5


<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Thr Val Ser Ala Leu Lys
1               5


<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Val Ser Ala Leu Lys
1               5


<210> SEQ ID NO 8
<211> LENGTH: 7
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 8

Thr Val Ser Ala Leu Phe Lys
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Thr Val Pro Ala Leu Phe Arg
1 5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Thr Val Pro Met Leu Phe Lys
1 5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Thr Val Pro Thr Leu Phe Lys
1 5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Thr Val Pro Met Leu Lys
1 5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Thr Val Pro Thr Leu Lys
1 5

-continued

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Val Pro Met Leu Lys
1 5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Val Pro Thr Leu Lys
1 5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Val Pro Met Leu Lys Glu
1 5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Val Pro Thr Leu Lys Asp
1 5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Val Pro Ala Leu Arg Asp
1 5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

-continued

Val Ser Ala Leu Lys Glu
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Val Ser Ala Leu Lys Asp
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Thr Ala Val Ser Leu Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Thr Ala Leu Val Ser Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Thr Val Leu Ser Ala Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Thr Leu Val Ser Ala Lys
1               5

<210> SEQ ID NO 25
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 25

Thr Met Val Pro Leu Lys
1               5


<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Met Leu Val Pro Lys
1               5


<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Val Leu Pro Met Lys
1               5


<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Leu Val Pro Met Lys
1               5


<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Thr Val Pro Leu Lys
1               5


<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Thr Leu Val Pro Lys
1               5
```

-continued

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Thr Val Leu Pro Thr Lys
1 5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Thr Leu Val Pro Thr Lys
1 5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Thr Ala Val Pro Leu Arg
1 5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Thr Ala Leu Val Pro Arg
1 5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Thr Val Leu Pro Ala Arg
1 5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Thr Leu Val Pro Ala Arg
1 5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Thr Ala Val Ser Leu Lys Glu
1 5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Thr Ala Leu Val Ser Lys Glu
1 5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Thr Val Leu Ser Ala Lys Glu
1 5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Thr Leu Val Ser Ala Lys Glu
1 5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Thr Met Val Pro Leu Lys Glu
1 5

<210> SEQ ID NO 42
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 42

Thr Met Leu Val Pro Lys Glu
1 5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Thr Val Leu Pro Met Lys Glu
1 5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Thr Leu Val Pro Met Lys Glu
1 5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Thr Thr Val Pro Leu Lys Asp
1 5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Thr Thr Leu Val Pro Lys Asp
1 5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Thr Val Leu Pro Thr Lys Asp
1 5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Thr Leu Val Pro Thr Lys Asp
1 5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Thr Ala Val Pro Leu Arg Asp
1 5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Thr Ala Leu Val Pro Arg Asp
1 5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Thr Val Leu Pro Ala Arg Asp
1 5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Thr Leu Val Pro Ala Arg Asp
1 5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Thr Ala Val Ser Leu Phe Lys
1 5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Thr Ala Leu Val Ser Phe Lys
1 5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Thr Val Leu Ser Ala Phe Lys
1 5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Thr Leu Val Ser Ala Phe Lys
1 5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Thr Met Val Pro Leu Phe Lys
1 5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Thr Met Leu Val Pro Phe Lys
1 5

<210> SEQ ID NO 59
<211> LENGTH: 7

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Thr Val Leu Pro Met Phe Lys
1 5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Thr Leu Val Pro Met Phe Lys
1 5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Thr Thr Val Pro Leu Phe Lys
1 5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Thr Thr Leu Val Pro Phe Lys
1 5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Thr Val Leu Pro Thr Phe Lys
1 5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Thr Leu Val Pro Thr Phe Lys 1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Ala Val Pro Leu Phe Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Ala Leu Val Pro Phe Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Val Leu Pro Ala Phe Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Leu Val Pro Ala Phe Arg
1               5

<210> SEQ ID NO 69
<211> LENGTH: 8
<212> TYPE: PRT
<213> ORGANISM: Homo sapiens

<400> SEQUENCE: 69

Lys Phe Thr Val Pro Met Leu Lys
1               5

<210> SEQ ID NO 70
<211> LENGTH: 8
<212> TYPE: PRT
<213> ORGANISM: Mus sp.

<400> SEQUENCE: 70

Lys Leu Thr Val Pro Thr Leu Lys
1               5

<210> SEQ ID NO 71
<211> LENGTH: 8
<212> TYPE: PRT
<213> ORGANISM: Rattus sp.

<400> SEQUENCE: 71

Lys Phe Thr Val Pro Ala Leu Arg
1 5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Lys Phe Thr Val Ser Ala Leu Lys
1 5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(4)
<223> OTHER INFORMATION: V, A, L, I, G, P, S, T, or M
<220> FEATURE:
<221> NAME/KEY: MOD_RES
<222> LOCATION: (5)..(5)
<223> OTHER INFORMATION: K, R, H, D, or E
<220> FEATURE:
<223> OTHER INFORMATION: See specification as filed for detailed description of substitutions and preferred embodiments

<400> SEQUENCE: 73

Xaa Xaa Xaa Xaa Xaa
1 5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(5)
<223> OTHER INFORMATION: V, A, L, I, G, P, S, T, or M
<220> FEATURE:
<221> NAME/KEY: MOD_RES
<222> LOCATION: (6)..(6)
<223> OTHER INFORMATION: K, R, H, D, or E
<220> FEATURE:
<223> OTHER INFORMATION: See specification as filed for detailed description of substitutions and preferred embodiments

<400> SEQUENCE: 74

Thr Xaa Xaa Xaa Xaa Xaa
1 5

<210> SEQ ID NO 75
<211> LENGTH: 6

<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(4)
<223> OTHER INFORMATION: V, A, L, I, G, P, S, T, or M
<220> FEATURE:
<221> NAME/KEY: MOD_RES
<222> LOCATION: (5)..(5)
<223> OTHER INFORMATION: K, R, H, D, or E
<220> FEATURE:
<221> NAME/KEY: MOD_RES
<222> LOCATION: (6)..(6)
<223> OTHER INFORMATION: E or D
<220> FEATURE:
<223> OTHER INFORMATION: See specification as filed for detailed description of substitutions and preferred embodiments

<400> SEQUENCE: 75

```
Xaa Xaa Xaa Xaa Xaa Xaa
1               5
```

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: F, L, W, or Y
<220> FEATURE:
<221> NAME/KEY: MOD_RES
<222> LOCATION: (3)..(6)
<223> OTHER INFORMATION: V, A, L, I, G, P, S, T, or M
<220> FEATURE:
<221> NAME/KEY: MOD_RES
<222> LOCATION: (7)..(7)
<223> OTHER INFORMATION: K, R, H, D, or E
<220> FEATURE:
<223> OTHER INFORMATION: See specification as filed for detailed description of substitutions and preferred embodiments

<400> SEQUENCE: 76

```
Xaa Thr Xaa Xaa Xaa Xaa Xaa
1               5
```

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(5)
<223> OTHER INFORMATION: V, A, L, I, G, P, S, T, or M
<220> FEATURE:
<221> NAME/KEY: MOD_RES
<222> LOCATION: (6)..(6)
<223> OTHER INFORMATION: K, R, H, D, or E
<220> FEATURE:
<221> NAME/KEY: MOD_RES
<222> LOCATION: (7)..(7)
<223> OTHER INFORMATION: E or D
<220> FEATURE:
<223> OTHER INFORMATION: See specification as filed for detailed description of substitutions and preferred embodiments

<400> SEQUENCE: 77

Thr Xaa Xaa Xaa Xaa Xaa Xaa
1 5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(4)
<223> OTHER INFORMATION: V, A, L, I, G, P, S, T, or M
<220> FEATURE:
<221> NAME/KEY: MOD_RES
<222> LOCATION: (5)..(5)
<223> OTHER INFORMATION: K, R, H, D, or E
<220> FEATURE:
<221> NAME/KEY: MOD_RES
<222> LOCATION: (6)..(6)
<223> OTHER INFORMATION: E or D
<220> FEATURE:
<221> NAME/KEY: MOD_RES
<222> LOCATION: (7)..(7)
<223> OTHER INFORMATION: A or I
<220> FEATURE:
<223> OTHER INFORMATION: See specification as filed for detailed description of substitutions and preferred embodiments

<400> SEQUENCE: 78

Xaa Xaa Xaa Xaa Xaa Xaa Xaa
1 5

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: S or P
<220> FEATURE:
<221> NAME/KEY: MOD_RES
<222> LOCATION: (3)..(3)
<223> OTHER INFORMATION: A, M, or T
<220> FEATURE:
<223> OTHER INFORMATION: See specification as filed for detailed description of substitutions and preferred embodiments

<400> SEQUENCE: 79

Val Xaa Xaa Leu
1

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: S or P
<220> FEATURE:
<221> NAME/KEY: MOD_RES
<222> LOCATION: (4)..(4)
<223> OTHER INFORMATION: A, M, or T

```
<220> FEATURE:
<223> OTHER INFORMATION: See specification as filed for detailed
      description of substitutions and preferred embodiments

<400> SEQUENCE: 80

Thr Val Xaa Xaa Leu
1               5


<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or P
<220> FEATURE:
<221> NAME/KEY: MOD_RES
<222> LOCATION: (4)..(4)
<223> OTHER INFORMATION: A, M, or T
<220> FEATURE:
<223> OTHER INFORMATION: See specification as filed for detailed
      description of substitutions and preferred embodiments

<400> SEQUENCE: 81

Thr Val Xaa Xaa Leu Lys
1               5


<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or P
<220> FEATURE:
<221> NAME/KEY: MOD_RES
<222> LOCATION: (4)..(4)
<223> OTHER INFORMATION: A, M, or T
<220> FEATURE:
<223> OTHER INFORMATION: See specification as filed for detailed
      description of substitutions and preferred embodiments

<400> SEQUENCE: 82

Thr Val Xaa Xaa Leu Phe Lys
1               5


<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Leu Ala Ser Val Thr
1               5


<210> SEQ ID NO 84
<211> LENGTH: 7
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 84

```
Lys Phe Leu Ala Ser Val Thr
1               5
```

<210> SEQ ID NO 85
<211> LENGTH: 736
<212> TYPE: PRT
<213> ORGANISM: Adeno-associated virus 9

<400> SEQUENCE: 85

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

-continued

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 86
<211> LENGTH: 609
<212> TYPE: PRT

<213> ORGANISM: Homo sapiens

<400> SEQUENCE: 86

```
Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

Ser Gly Arg Asp Ser Leu Ile Phe Leu Val Asp Ala Ser Lys Ala Met
        35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Ser Asp Arg
65                  70                  75                  80

Asp Leu Leu Ala Val Val Phe Tyr Gly Thr Glu Lys Asp Lys Asn Ser
                85                  90                  95

Val Asn Phe Lys Asn Ile Tyr Val Leu Gln Glu Leu Asp Asn Pro Gly
            100                 105                 110

Ala Lys Arg Ile Leu Glu Leu Asp Gln Phe Lys Gly Gln Gln Gly Gln
        115                 120                 125

Lys Arg Phe Gln Asp Met Met Gly His Gly Ser Asp Tyr Ser Leu Ser
    130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Ala Lys Ala Ser Arg Ala Arg Thr Lys Ala Gly Asp
            180                 185                 190

Leu Arg Asp Thr Gly Ile Phe Leu Asp Leu Met His Leu Lys Lys Pro
        195                 200                 205

Gly Gly Phe Asp Ile Ser Leu Phe Tyr Arg Asp Ile Ile Ser Ile Ala
    210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
            260                 265                 270

Ile Tyr Asn Leu Val Gln Lys Ala Leu Lys Pro Pro Pro Ile Lys Leu
        275                 280                 285

Tyr Arg Glu Thr Asn Glu Pro Val Lys Thr Lys Thr Arg Thr Phe Asn
    290                 295                 300

Thr Ser Thr Gly Gly Leu Leu Leu Pro Ser Asp Thr Lys Arg Ser Gln
305                 310                 315                 320

Ile Tyr Gly Ser Arg Gln Ile Ile Leu Glu Lys Glu Glu Thr Glu Glu
                325                 330                 335

Leu Lys Arg Phe Asp Asp Pro Gly Leu Met Leu Met Gly Phe Lys Pro
            340                 345                 350

Leu Val Leu Leu Lys Lys His His Tyr Leu Arg Pro Ser Leu Phe Val
        355                 360                 365

Tyr Pro Glu Glu Ser Leu Val Ile Gly Ser Ser Thr Leu Phe Ser Ala
    370                 375                 380

Leu Leu Ile Lys Cys Leu Glu Lys Glu Val Ala Ala Leu Cys Arg Tyr
385                 390                 395                 400
```

-continued

```
Thr Pro Arg Arg Asn Ile Pro Pro Tyr Phe Val Ala Leu Val Pro Gln
                405                 410                 415

Glu Glu Glu Leu Asp Asp Gln Lys Ile Gln Val Thr Pro Pro Gly Phe
            420                 425                 430

Gln Leu Val Phe Leu Pro Phe Ala Asp Asp Lys Arg Lys Met Pro Phe
        435                 440                 445

Thr Glu Lys Ile Met Ala Thr Pro Glu Gln Val Gly Lys Met Lys Ala
    450                 455                 460

Ile Val Glu Lys Leu Arg Phe Thr Tyr Arg Ser Asp Ser Phe Glu Asn
465                 470                 475                 480

Pro Val Leu Gln Gln His Phe Arg Asn Leu Glu Ala Leu Ala Leu Asp
                485                 490                 495

Leu Met Glu Pro Glu Gln Ala Val Asp Leu Thr Leu Pro Lys Val Glu
            500                 505                 510

Ala Met Asn Lys Arg Leu Gly Ser Leu Val Asp Glu Phe Lys Glu Leu
        515                 520                 525

Val Tyr Pro Pro Asp Tyr Asn Pro Glu Gly Lys Val Thr Lys Arg Lys
    530                 535                 540

His Asp Asn Glu Gly Ser Gly Ser Lys Arg Pro Lys Val Glu Tyr Ser
545                 550                 555                 560

Glu Glu Glu Leu Lys Thr His Ile Ser Lys Gly Thr Leu Gly Lys Phe
                565                 570                 575

Thr Val Pro Met Leu Lys Glu Ala Cys Arg Ala Tyr Gly Leu Lys Ser
            580                 585                 590

Gly Leu Lys Lys Gln Glu Leu Leu Glu Ala Leu Thr Lys His Phe Gln
        595                 600                 605

Asp


<210> SEQ ID NO 87
<211> LENGTH: 608
<212> TYPE: PRT
<213> ORGANISM: Mus sp.

<400> SEQUENCE: 87

Met Ser Glu Trp Glu Ser Tyr Tyr Lys Thr Glu Gly Glu Glu Glu Glu
1               5                   10                  15

Glu Glu Glu Glu Ser Pro Asp Thr Gly Gly Glu Tyr Lys Tyr Ser Gly
            20                  25                  30

Arg Asp Ser Leu Ile Phe Leu Val Asp Ala Ser Arg Ala Met Phe Glu
        35                  40                  45

Ser Gln Gly Glu Asp Glu Leu Thr Pro Phe Asp Met Ser Ile Gln Cys
    50                  55                  60

Ile Gln Ser Val Tyr Thr Ser Lys Ile Ile Ser Ser Asp Arg Asp Leu
65                  70                  75                  80

Leu Ala Val Val Phe Tyr Gly Thr Glu Lys Asp Lys Asn Ser Val Asn
                85                  90                  95

Phe Lys Asn Ile Tyr Val Leu Gln Asp Leu Asp Asn Pro Gly Ala Lys
            100                 105                 110

Arg Val Leu Glu Leu Asp Gln Phe Lys Gly Gln Gln Gly Lys Lys His
        115                 120                 125

Phe Arg Asp Thr Val Gly His Gly Ser Asp Tyr Ser Leu Ser Glu Val
    130                 135                 140

Leu Trp Val Cys Ala Asn Leu Phe Ser Asp Val Gln Leu Lys Met Ser
145                 150                 155                 160
```

-continued

```
His Lys Arg Ile Met Leu Phe Thr Asn Glu Asp Asp Pro His Gly Arg
                165                 170                 175

Asp Ser Ala Lys Ala Ser Arg Ala Arg Thr Lys Ala Ser Asp Leu Arg
            180                 185                 190

Asp Thr Gly Ile Phe Leu Asp Leu Met His Leu Lys Lys Pro Gly Gly
        195                 200                 205

Phe Asp Val Ser Val Phe Tyr Arg Asp Ile Ile Thr Thr Ala Glu Asp
    210                 215                 220

Glu Asp Leu Gly Val His Phe Glu Glu Ser Ser Lys Leu Glu Asp Leu
225                 230                 235                 240

Leu Arg Lys Val Arg Ala Lys Glu Thr Lys Lys Arg Val Leu Ser Arg
                245                 250                 255

Leu Lys Phe Lys Leu Gly Glu Asp Val Val Leu Met Val Gly Ile Tyr
            260                 265                 270

Asn Leu Val Gln Lys Ala Asn Lys Pro Phe Pro Val Arg Leu Tyr Arg
        275                 280                 285

Glu Thr Asn Glu Pro Val Lys Thr Lys Thr Arg Thr Phe Asn Val Asn
    290                 295                 300

Thr Gly Ser Leu Leu Leu Pro Ser Asp Thr Lys Arg Ser Leu Thr Tyr
305                 310                 315                 320

Gly Thr Arg Gln Ile Val Leu Glu Lys Glu Glu Thr Glu Glu Leu Lys
                325                 330                 335

Arg Phe Asp Glu Pro Gly Leu Ile Leu Met Gly Phe Lys Pro Thr Val
            340                 345                 350

Met Leu Lys Lys Gln His Tyr Leu Arg Pro Ser Leu Phe Val Tyr Pro
        355                 360                 365

Glu Glu Ser Leu Val Ser Gly Ser Ser Thr Leu Phe Ser Ala Leu Leu
    370                 375                 380

Thr Lys Cys Val Glu Lys Glu Val Ile Ala Val Cys Arg Tyr Thr Pro
385                 390                 395                 400

Arg Lys Asn Val Ser Pro Tyr Phe Val Ala Leu Val Pro Gln Glu Glu
                405                 410                 415

Glu Leu Asp Asp Gln Asn Ile Gln Val Thr Pro Gly Gly Phe Gln Leu
            420                 425                 430

Val Phe Leu Pro Tyr Ala Asp Asp Lys Arg Lys Val Pro Phe Thr Glu
        435                 440                 445

Lys Val Thr Ala Asn Gln Glu Gln Ile Asp Lys Met Lys Ala Ile Val
    450                 455                 460

Gln Lys Leu Arg Phe Thr Tyr Arg Ser Asp Ser Phe Glu Asn Pro Val
465                 470                 475                 480

Leu Gln Gln His Phe Arg Asn Leu Glu Ala Leu Ala Leu Asp Met Met
                485                 490                 495

Glu Ser Glu Gln Val Val Asp Leu Thr Leu Pro Lys Val Glu Ala Ile
            500                 505                 510

Lys Lys Arg Leu Gly Ser Leu Ala Asp Glu Phe Lys Glu Leu Val Tyr
        515                 520                 525

Pro Pro Gly Tyr Asn Pro Glu Gly Lys Val Ala Lys Arg Lys Gln Asp
    530                 535                 540

Asp Glu Gly Ser Thr Ser Lys Lys Pro Lys Val Glu Leu Ser Glu Glu
545                 550                 555                 560

Glu Leu Lys Ala His Phe Arg Lys Gly Thr Leu Gly Lys Leu Thr Val
                565                 570                 575

Pro Thr Leu Lys Asp Ile Cys Lys Ala His Gly Leu Lys Ser Gly Pro
```

```
            580                 585                 590

Lys Lys Gln Glu Leu Leu Asp Ala Leu Ile Arg His Leu Glu Lys Asn
        595                 600                 605


<210> SEQ ID NO 88
<211> LENGTH: 608
<212> TYPE: PRT
<213> ORGANISM: Rattus sp.

<400> SEQUENCE: 88

Met Ser Glu Trp Glu Ser Tyr Tyr Lys Thr Glu Gly Glu Glu Glu Glu
1               5                   10                  15

Glu Glu Glu Gln Ser Pro Asp Thr Asn Gly Glu Tyr Lys Tyr Ser Gly
            20                  25                  30

Arg Asp Ser Leu Ile Phe Leu Val Asp Ala Ser Arg Ala Met Phe Glu
        35                  40                  45

Ser Gln Gly Glu Asp Glu Leu Thr Pro Phe Asp Met Ser Ile Gln Cys
    50                  55                  60

Ile Gln Ser Val Tyr Thr Ser Lys Ile Ile Ser Ser Asp Arg Asp Leu
65                  70                  75                  80

Leu Ala Val Val Phe Tyr Gly Thr Glu Lys Asp Lys Asn Ser Val Asn
                85                  90                  95

Phe Lys Ser Ile Tyr Val Leu Gln Asp Leu Asp Asn Pro Gly Ala Lys
            100                 105                 110

Arg Val Leu Glu Leu Asp Arg Phe Lys Gly Gln Gln Gly Lys Lys His
        115                 120                 125

Phe Arg Asp Thr Ile Gly His Gly Ser Asp Tyr Ser Leu Ser Glu Val
    130                 135                 140

Leu Trp Val Cys Ala Asn Leu Phe Ser Asp Val Gln Phe Lys Met Ser
145                 150                 155                 160

His Lys Arg Ile Met Leu Phe Thr Asn Glu Asp Asp Pro His Gly Asn
                165                 170                 175

Asp Ser Ala Lys Ala Ser Arg Ala Arg Thr Lys Ala Ser Asp Leu Arg
            180                 185                 190

Asp Thr Gly Ile Phe Leu Asp Leu Met His Leu Lys Lys Arg Gly Gly
        195                 200                 205

Phe Asp Val Ser Leu Phe Tyr Arg Asp Ile Ile Ser Ile Ala Glu Asp
    210                 215                 220

Glu Asp Leu Gly Val His Phe Glu Glu Ser Ser Lys Leu Glu Asp Leu
225                 230                 235                 240

Leu Arg Lys Val Arg Ala Lys Glu Thr Lys Lys Arg Val Leu Ser Arg
                245                 250                 255

Leu Lys Phe Lys Leu Gly Lys Asp Val Ala Leu Met Val Gly Val Tyr
            260                 265                 270

Asn Leu Val Gln Lys Ala Asn Lys Pro Phe Pro Val Arg Leu Tyr Arg
        275                 280                 285

Glu Thr Asn Glu Pro Val Lys Thr Lys Thr Arg Thr Phe Asn Val Asn
    290                 295                 300

Thr Gly Ser Leu Leu Leu Pro Ser Asp Thr Lys Arg Ser Leu Thr Phe
305                 310                 315                 320

Gly Thr Arg Gln Ile Val Leu Glu Lys Glu Glu Thr Glu Glu Leu Lys
                325                 330                 335

Arg Phe Asp Glu Pro Gly Leu Ile Leu Met Gly Phe Lys Pro Met Val
            340                 345                 350
```

```
Met Leu Lys Asn His His Tyr Leu Arg Pro Ser Leu Phe Leu Tyr Pro
        355                 360                 365

Glu Glu Ser Leu Val Asn Gly Ser Ser Thr Leu Phe Ser Ala Leu Leu
    370                 375                 380

Thr Lys Cys Val Glu Lys Glu Val Ile Ala Val Cys Arg Tyr Thr Ala
385                 390                 395                 400

Arg Lys Asn Val Ser Pro Tyr Phe Val Ala Leu Val Pro Gln Glu Glu
                405                 410                 415

Glu Leu Asp Asp Gln Asn Ile Gln Val Thr Pro Ala Gly Phe Gln Leu
            420                 425                 430

Val Phe Leu Pro Tyr Ala Asp Asp Lys Arg Lys Val Pro Phe Thr Glu
        435                 440                 445

Lys Val Met Ala Asn Pro Glu Gln Ile Asp Lys Met Lys Ala Ile Val
    450                 455                 460

Gln Lys Leu Arg Phe Thr Tyr Arg Ser Asp Ser Phe Glu Asn Pro Val
465                 470                 475                 480

Leu Gln Gln His Phe Arg Asn Leu Glu Ala Leu Ala Leu Asp Met Met
                485                 490                 495

Glu Ser Glu Gln Val Val Asp Leu Thr Leu Pro Lys Val Glu Ala Ile
            500                 505                 510

Lys Lys Arg Leu Gly Ser Leu Ala Asp Glu Phe Lys Glu Leu Val Tyr
        515                 520                 525

Pro Pro Gly Tyr Asn Pro Glu Gly Lys Ile Ala Lys Arg Lys Ala Asp
    530                 535                 540

Asn Glu Gly Ser Ala Ser Lys Lys Pro Lys Val Glu Leu Ser Glu Glu
545                 550                 555                 560

Glu Leu Lys Asp Leu Phe Ala Lys Gly Thr Leu Gly Lys Leu Thr Val
                565                 570                 575

Pro Ala Leu Arg Asp Ile Cys Lys Ala Tyr Gly Leu Lys Ser Gly Pro
            580                 585                 590

Lys Lys Gln Glu Leu Leu Glu Ala Leu Ser Arg His Leu Glu Lys Asn
        595                 600                 605


<210> SEQ ID NO 89
<211> LENGTH: 742
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110
```

```
Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525
```

```
Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Val Ser Ala
            580                 585                 590

Leu Lys Ala Gln Ala Gln Thr Gly Trp Val Gln Asn Gln Gly Ile Leu
        595                 600                 605

Pro Gly Met Val Trp Gln Asp Arg Asp Val Tyr Leu Gln Gly Pro Ile
    610                 615                 620

Trp Ala Lys Ile Pro His Thr Asp Gly Asn Phe His Pro Ser Pro Leu
625                 630                 635                 640

Met Gly Gly Phe Gly Met Lys His Pro Pro Pro Gln Ile Leu Ile Lys
                645                 650                 655

Asn Thr Pro Val Pro Ala Asp Pro Pro Thr Ala Phe Asn Lys Asp Lys
            660                 665                 670

Leu Asn Ser Phe Ile Thr Gln Tyr Ser Thr Gly Gln Val Ser Val Glu
        675                 680                 685

Ile Glu Trp Glu Leu Gln Lys Glu Asn Ser Lys Arg Trp Asn Pro Glu
    690                 695                 700

Ile Gln Tyr Thr Ser Asn Tyr Tyr Lys Ser Asn Asn Val Glu Phe Ala
705                 710                 715                 720

Val Asn Thr Glu Gly Val Tyr Ser Glu Pro Arg Pro Ile Gly Thr Arg
                725                 730                 735

Tyr Leu Thr Arg Asn Leu
            740


<210> SEQ ID NO 90
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

-continued

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560
```

```
Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Val Ser Ala
            580                 585                 590

Leu Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740


<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

ggaaccccta gtgatggagt t                                              21


<210> SEQ ID NO 92
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

cggcctcagt gagcga                                                    16


<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Gly Gly Arg Leu Ser Tyr Ser Arg Arg Arg Phe Ser Thr Ser Thr
1               5                   10                  15

Gly Arg
```

```
<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

His Ala Arg Ile Lys Pro Thr Phe Arg Arg Leu Lys Trp Lys Tyr Lys
1               5                   10                  15

Gly Lys Phe Trp
            20


<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Leu Ser Ser Ile Phe Ser Arg Ile Gly Asp Pro
1               5                   10


<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Gly Tyr Leu Leu Gly Lys Ile Asn Leu Lys Ala Leu Ala Ala Leu
1               5                   10                  15

Ala Lys Lys Ile Leu
            20


<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Arg Leu Pro Pro Pro Val Arg Leu Pro Pro Pro Val Arg Leu Pro
1               5                   10                  15

Pro Pro


<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Val Glu Leu Pro Pro Pro Val Glu Leu Pro Pro Pro Val Glu Leu Pro
1               5                   10                  15

Pro Pro
```

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Lys Gly Thr Tyr Lys Lys Lys Leu Met Arg Ile Pro Leu Lys Gly Thr
1               5                   10                  15

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Pro Pro Arg Pro Pro Arg Pro Pro Arg
1               5

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Pro Pro Arg Pro Pro Arg Pro Pro Arg Pro Pro Arg Pro Pro Arg
1               5                   10                  15

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Arg Arg Arg Arg Arg Arg Arg Arg
1               5

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Leu Arg Arg Glu Arg Gln Ser Arg Leu Arg Arg Glu Arg Gln Ser Arg
1               5                   10                  15

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Arg Lys Lys Arg Arg Gln Arg Arg Arg
1 5

<210> SEQ ID NO 105
<211> LENGTH: 524
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Met Glu Thr Asp Thr Leu Leu Leu Trp Val Leu Leu Leu Trp Val Pro
1 5 10 15

Gly Ser Thr Gly Asp Tyr Pro Tyr Asp Val Pro Asp Tyr Ala Gly Ala
20 25 30

Gln Pro Ala Asp Asp Ile Gln Met Thr Gln Ser Pro Ser Ser Leu Ser
35 40 45

Ala Ser Val Gly Asp Arg Val Thr Ile Thr Cys Arg Ala Ser Gln Asp
50 55 60

Val Ser Thr Ala Val Ala Trp Tyr Gln Gln Lys Pro Gly Lys Ala Pro
65 70 75 80

Lys Leu Leu Ile Tyr Ser Ala Ser Phe Leu Tyr Ser Gly Val Pro Ser
85 90 95

Arg Phe Ser Gly Ser Gly Ser Gly Thr Asp Phe Thr Leu Thr Ile Ser
100 105 110

Ser Leu Gln Pro Glu Asp Phe Ala Thr Tyr Tyr Cys Gln Gln Tyr Leu
115 120 125

Tyr His Pro Ala Thr Phe Gly Gln Gly Thr Lys Val Glu Ile Lys Arg
130 135 140

Gly Gly Gly Gly Ser Gly Gly Gly Gly Ser Gly Gly Gly Gly Ser Glu
145 150 155 160

Val Gln Leu Val Glu Ser Gly Gly Gly Leu Val Gln Pro Gly Gly Ser
165 170 175

Leu Arg Leu Ser Cys Ala Ala Ser Gly Phe Thr Phe Ser Asp Ser Trp
180 185 190

Ile His Trp Val Arg Gln Ala Pro Gly Lys Gly Leu Glu Trp Val Ala
195 200 205

Trp Ile Ser Pro Tyr Gly Gly Ser Thr Tyr Tyr Ala Asp Ser Val Lys
210 215 220

Gly Arg Phe Thr Ile Ser Ala Asp Thr Ser Lys Asn Thr Ala Tyr Leu
225 230 235 240

Gln Met Asn Ser Leu Arg Ala Glu Asp Thr Ala Val Tyr Tyr Cys Ala
245 250 255

Arg Arg His Trp Pro Gly Gly Phe Asp Tyr Trp Gly Gln Gly Thr Leu
260 265 270

Val Thr Val Ser Ala Val Asp Glu Ala Lys Ser Cys Asp Lys Thr His
275 280 285

Thr Cys Pro Pro Cys Pro Ala Pro Glu Leu Leu Gly Gly Pro Ser Val
290 295 300

Phe Leu Phe Pro Pro Lys Pro Lys Asp Thr Leu Met Ile Ser Arg Thr
305 310 315 320

Pro Glu Val Thr Cys Val Val Val Asp Val Ser His Glu Asp Pro Glu
325 330 335

```
Val Lys Phe Asn Trp Tyr Val Asp Gly Val Glu Val His Asn Ala Lys
            340                 345                 350

Thr Lys Pro Arg Glu Glu Gln Tyr Asn Ser Thr Tyr Arg Val Val Ser
        355                 360                 365

Val Leu Thr Val Leu His Gln Asp Trp Leu Asn Gly Lys Glu Tyr Lys
    370                 375                 380

Cys Lys Val Ser Asn Lys Ala Leu Pro Ala Pro Ile Glu Lys Thr Ile
385                 390                 395                 400

Ser Lys Ala Lys Gly Gln Pro Arg Glu Pro Gln Val Tyr Thr Leu Pro
                405                 410                 415

Pro Ser Arg Asp Glu Leu Thr Lys Asn Gln Val Ser Leu Thr Cys Leu
            420                 425                 430

Val Lys Gly Phe Tyr Pro Ser Asp Ile Ala Val Glu Trp Glu Ser Asn
        435                 440                 445

Gly Gln Pro Glu Asn Asn Tyr Lys Thr Thr Pro Pro Val Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys Val
            500                 505                 510

Asp Glu Gln Lys Leu Ile Ser Glu Glu Asp Leu Asn
        515                 520
```

<210> SEQ ID NO 106
<211> LENGTH: 1575
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106

```
atggagacag acacactcct gctatgggta ctgctgctct gggttccagg ttccactggt     60

gactatccat atgatgttcc agattatgct ggggcccagc cggccgacga catccaaatg    120

acccagagtc catctagtct gtctgcttcg gtaggtgata gggtcactat tacttgcagg    180

gcctcccagg acgtgtcaac tgcagtggct tggtaccaac agaagcccgg gaaagctccc    240

aaactgctga tctactccgc cagctttctg tattccggag ttccgtctag attttccgga    300

tcaggaagcg gcacggattt cacactcaca ataagcagcc tacaaccaga ggacttcgca    360

acctactatt gtcaacagta cctgtaccat ccagccacct ttgggcaggg caccaaggtg    420

gaaatcaagc gcggtggtgg tggatcaggt ggaggcggaa gtggaggtgg cggatccgaa    480

gttcagcttg tcgagtccgg tggcggcctg gttcagcctg gtgggtcttt gcgtctgtca    540

tgcgccgcct ctggtttcac cttttcagac tcttggatcc actgggtgag acaggcccca    600

ggaaagggtc ttgagtgggt tgcatggatt agcccctacg gcggcagtac atattacgcg    660

gatagcgtga aagggaggtt taccatcagc gcagacacgt cgaagaacac cgcatacctc    720

cagatgaatt ccctccgagc cgaagatacc gccgtgtact attgtgctcg ccggcattgg    780

cctggcggct tcgattattg gggacaggga actctagtaa cagtgtcggc tgtcgacgag    840

gccaaatctt gtgacaaaac tcacacatgc ccaccgtgcc cagcacccga actcctgggg    900

ggaccgtcag tcttcctctt ccccccaaaa cccaaggaca ccctcatgat ctcccggacc    960
```

-continued

```
cctgaggtca catgcgtggt ggtggacgtg agccacgaag accctgaggt caagttcaac   1020

tggtacgtgg acggcgtgga ggtgcataat gccaagacaa agccgcggga ggagcagtac   1080

aacagcacgt accgtgtggt cagcgtcctc accgtcctgc accaggactg gctgaatggc   1140

aaggagtaca agtgcaaggt ctccaacaaa gccctcccag cccccatcga gaaaaccatc   1200

tccaaagcca aggggcagcc ccgagaacca caggtgtaca ccctgccccc atcccgggat   1260

gagctgacca agaaccaggt cagcctgacc tgcctggtca aaggcttcta tcccagcgac   1320

atcgccgtgg agtgggagag caatgggcag ccggagaaca actacaagac cacgcctccc   1380

gtgctggact ccgacggctc cttcttcctc tacagcaagc tcaccgtgga caagagcagg   1440

tggcagcagg ggaacgtctt ctcatgctcc gtgatgcatg aggctctgca caaccactac   1500

acgcagaaga gcctctccct gtctccgggt aaagtcgacg aacaaaaact catctcagaa   1560

gaagatctga attga                                                    1575
```

```
<210> SEQ ID NO 107
<211> LENGTH: 25
<212> TYPE: PRT
<213> ORGANISM: Homo sapiens

<400> SEQUENCE: 107

Met Gly Val Leu Leu Thr Gln Arg Thr Leu Leu Ser Leu Val Leu Ala
1               5                   10                  15

Leu Leu Phe Pro Ser Met Ala Ser Met
            20                  25


<210> SEQ ID NO 108
<211> LENGTH: 19
<212> TYPE: PRT
<213> ORGANISM: Homo sapiens

<400> SEQUENCE: 108

Met Gly Trp Ser Cys Ile Ile Leu Phe Leu Val Ala Thr Ala Thr Gly
1               5                   10                  15

Val His Ser


<210> SEQ ID NO 109
<211> LENGTH: 21
<212> TYPE: PRT
<213> ORGANISM: Homo sapiens

<400> SEQUENCE: 109

Met Trp Trp Arg Leu Trp Trp Leu Leu Leu Leu Leu Leu Leu Leu Trp
1               5                   10                  15

Pro Met Val Trp Ala
            20


<210> SEQ ID NO 110
<211> LENGTH: 22
<212> TYPE: PRT
<213> ORGANISM: Homo sapiens

<400> SEQUENCE: 110

Met Asp Met Arg Val Pro Ala Gln Leu Leu Gly Leu Leu Leu Leu Trp
1               5                   10                  15

Leu Arg Gly Ala Arg Cys
            20


<210> SEQ ID NO 111
```

<211> LENGTH: 16
<212> TYPE: PRT
<213> ORGANISM: Homo sapiens

<400> SEQUENCE: 111

Met Pro Leu Leu Leu Leu Leu Pro Leu Leu Trp Ala Gly Ala Leu Ala
1 5 10 15

<210> SEQ ID NO 112
<211> LENGTH: 23
<212> TYPE: PRT
<213> ORGANISM: Homo sapiens

<400> SEQUENCE: 112

Met Asp Ala Met Lys Arg Gly Leu Cys Cys Val Leu Leu Leu Cys Gly
1 5 10 15

Ala Val Phe Val Ser Pro Ser
20

<210> SEQ ID NO 113
<211> LENGTH: 18
<212> TYPE: PRT
<213> ORGANISM: Homo sapiens

<400> SEQUENCE: 113

Met Ala Phe Leu Trp Leu Leu Ser Cys Trp Ala Leu Leu Gly Thr Thr
1 5 10 15

Phe Gly

<210> SEQ ID NO 114
<211> LENGTH: 15
<212> TYPE: PRT
<213> ORGANISM: Homo sapiens

<400> SEQUENCE: 114

Met Asn Leu Leu Leu Ile Leu Thr Phe Val Ala Ala Ala Val Ala
1 5 10 15

<210> SEQ ID NO 115
<211> LENGTH: 20
<212> TYPE: PRT
<213> ORGANISM: Homo sapiens

<400> SEQUENCE: 115

Met Tyr Arg Met Gln Leu Leu Ser Cys Ile Ala Leu Ser Leu Ala Leu
1 5 10 15

Val Thr Asn Ser
20

<210> SEQ ID NO 116
<211> LENGTH: 16
<212> TYPE: PRT
<213> ORGANISM: Homo sapiens

<400> SEQUENCE: 116

Met Lys Trp Val Thr Phe Ile Ser Leu Leu Phe Ser Ser Ala Tyr Ser
1 5 10 15

<210> SEQ ID NO 117
<211> LENGTH: 24
<212> TYPE: PRT
<213> ORGANISM: Homo sapiens

<400> SEQUENCE: 117

-continued

```
Met Ala Leu Trp Met Arg Leu Leu Pro Leu Leu Ala Leu Leu Ala Leu
1               5                   10                  15

Trp Gly Pro Asp Pro Ala Ala Ala
            20
```